United States Patent [19]

Bernauer et al.

[11] Patent Number: 5,236,952
[45] Date of Patent: Aug. 17, 1993

[54] CATECHOL DERIVATIVES

[75] Inventors: Karl Bernauer, Oberwil; Janos Borgulya, Basel; Hans Bruderer, Biel-Benken; Mosé DaPrada, Riehen; Gerhard Zürcher, Basel, all of Switzerland

[73] Assignee: Hoffmann-La Roche Inc., Nutley, N.J.

[21] Appl. No.: 686,210

[22] Filed: Apr. 16, 1991

Related U.S. Application Data

[63] Continuation of Ser. No. 395,110, Aug. 16, 1989, abandoned, which is a continuation of Ser. No. 22,891, Mar. 6, 1987, abandoned.

[30] Foreign Application Priority Data

Mar. 11, 1986 [CH]  Switzerland ............................ 980/86
Jan. 9, 1987 [CH]  Switzerland ............................ 62/87

[51] Int. Cl.$^5$ ............................................. A61K 31/275
[52] U.S. Cl. ................................... 514/520; 514/523; 514/525; 514/676; 568/306; 558/415
[58] Field of Search ............... 568/306; 558/415, 520, 558/525; 514/676, 523

[56] References Cited

U.S. PATENT DOCUMENTS

| | | | |
|---|---|---|---|
| 2,199,389 | 5/1940 | Britton et al. | 568/306 |
| 3,985,783 | 10/1976 | Johnson et al. | 568/342 |
| 4,124,726 | 11/1982 | Hamazaki et al. | 514/678 |
| 4,332,820 | 6/1982 | Markley | 558/415 |
| 4,622,066 | 11/1986 | Kitahara et al. | 71/98 |
| 4,801,616 | 1/1989 | Gapinski | 514/381 |
| 4,963,590 | 10/1990 | Backstrom et al. | 514/678 |

FOREIGN PATENT DOCUMENTS

| | | | |
|---|---|---|---|
| 79141 | 10/1982 | European Pat. Off. | 514/680 |
| 142283 | 5/1985 | European Pat. Off. | |
| 967605 | 8/1964 | United Kingdom | 71/98 |
| 2038819 | 12/1978 | United Kingdom | |

OTHER PUBLICATIONS

Miyamoto et al., Chemical Abstracts, vol. 99, 121998 (1983).

(List continued on next page.)

*Primary Examiner*—James H. Reamer
*Attorney, Agent, or Firm*—George M. Gould; George W. Johnston; Ellen Ciambrone Coletti

[57] ABSTRACT

Catechol derivatives of the formula

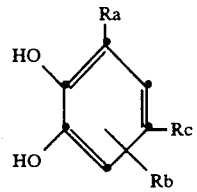

Ia wherein Ra, Rb and Rc have the significance given herein, the ester and ether derivatives thereof which are hydrolyzable under physiological conditions and the pharmaceutically acceptable salts thereof are described and possess valuable pharmacological properties. In particular, they inhibit the enzyme catechol-O-methyltransferase (COMT), a soluble, magnesium-dependent enzyme which catalyses the transference of the methyl group of S-adensoylmethionine to a catechol substrate, whereby the corresponding methyl ethers are formed. Suitable substrates which can be O-methylated by COMT and which can thus be deactivated are, for example, extraneuornal catecholamines and exogeneously-administered therapeutically active substances having a catechol structure.

Formula Ia above embraces not only compounds which form part of the invention, but also known compounds; the compounds which form part of the invention can be prepared according to known methods.

22 Claims, No Drawings

OTHER PUBLICATIONS

Chemical Abstracts, vol. 95, 135254t (1981).
Nikadejvic et al., Catechol-O-Methyl Transferase II. A New Class of Inhibitors of Catechol-O-Methyl Transferase, J. Pharmacol. Exp. Ther. 174, 83-93 (1970).
Fahn et al., Effect of Catechol-O-Methyl Transferase Inhibitor, U-0521 with Levodopa Administration, Biochem Pharmacol. 28, 1221-1225 (1979).
Reches et al., Catechol-O-Methyl Transferase Inhibition by U-0521 Increases Striatal Utilization of Levdopa, Arch. Pharmacol. 320, 34-37 (1982).
Borchardt et al., Catechol-O-Methyl Transferase, J. Med. Chem. 25, 258-263 (1982).
Borchardt and Huber, Catechol-O-Methyl Transferase, J. Med. Chem. 25,321-323 (1982).
Borchardt and Huber, Function and Regulation of Monoamine Enzymes, Basic and Clinical Aspects, ed. E. Usdin, N. Weinder and M. B. H. Youdim, MacMillin Publishers, 1981, 657-664.
Chemical Abstracts 92, 146461x (1980).
Chemical Abstracts, 98,50111f (1983).
Traxler and Ghisalba, A Genetic Approach to the Biosynthesis of the Rifamycin-Chromophore in Nocardia Mediterranei, J. Antibiotics 35 (10), 1361-6 (1982).
Chemical Abstracts Service, Registry Handbook 1965-1971, p. 10666R.

CATECHOL DERIVATIVES

This is a continuation of application Ser. No. 395,110, filed Aug. 16, 1989 now abandoned, which is a continuation of Ser. No. 07/022,891, filed Mar. 6, 1987, now abandoned.

BRIEF SUMMARY OF THE INVENTION

The invention relates to catechol derivatives of the formula

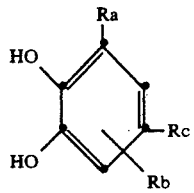

Ia wherein Ra is nitro or cyano, Rb is hydrogen or halogen, Rc is halogen, nitro, cyano or the group $-(A)_n-(Q)_m-R^1$ or $-(A)_n-Q-R^2$, A is vinylene optionally substituted by lower alkyl, n is the integer 0 or 1, m is the integer 0 or 1, $R^1$ is the group $-COR^3$, an aromatic carbocyclic group, or an aromatic or partially unsaturated heterocyclic group attached via a carbon atom, $R^2$ is hydrogen or an optionally substituted, saturated or partially unsaturated lower hydrocarbon residue, $R^3$ is hydroxy, amino, an optionally substituted, saturated or partially unsaturated, lower hydrocarbon residue attached via an oxygen atom or an imino or lower alkylimino group or a saturated, N-containing heterocyclic group attached via a ring nitrogen atom, Q is the group $-CO-$ or $>C=N-(Z-)_p-R^4$, Z is an oxygen atom or an imino group, P is the integer 0 or 1 and $R^4$ is hydrogen or saturated or partially unsaturated, lower hydrocarbon residue which is optionally substituted and which is optionally attached via a carbonyl group, the ester and ether derivatives thereof which are hydrolyzable under physiological conditions and the pharmaceutically acceptable salts thereof. The compounds of formula Ia possess valuable pharmacological properties. In particular, these compounds inhibit the enzyme catechol-O-methyltransferase (COMT), a soluble, magnesium-dependent enzyme which catalyzes the transference of the methyl group of S-adenosylmethionine to a catechol substrate, whereby the corresponding methyl ethers are formed. Suitable substrates which can be O-methylated by COMT and which can thus be deactivated are, for example, extraneuronal catecholamines and exogeneously-administered therapeutically active substances having a catechol structure.

The compounds of formula Ia above can accordingly be used in the prevention or control of illnesses in which a deactivation of extraneuronal catecholamines by COMT plays a role, for example, in the prevention or control of depressions. In this case the compounds of formula Ia above can be used as individual compounds or in combination with other therapeutically active substances which favorably influence the course of the illness. The compounds of formula Ia can, however, also be used as co-medications with other therapeutically active substances.

The compounds of formula Ia can, however, also be used to improve the prevention or control of illnesses with therapeutically active substances which have a catechol structure. The treatment of Parkinson's disease and of parkinsonism with L-dopa, a therapeutically active substance having the catechol structure, can be mentioned as an example. In such cases the compounds of formula Ia can be used in the form of a co-medication or as combination preparations.

The field of diagnostics offers a further possibility for the use of the compounds of formula Ia above. After the administration of $[^{18}F]$-6-fluoro-L-dopa, $[^{18}F]$-dopamine in the brain can be visualized with the aid of positron emission tomography. By adding a compound of formula Ia above, the COMT is inhibited and thus the formation of $[^{18}F]$-3-O-methyldopa is prevented. In the absence of a COMT-inhibitor, the $[^{18}F]$-3-O-methyldopa would penetrate into the brain and lead to a greatly increased background which would made the diagnosis very much more difficult.

DETAILED DESCRIPTION OF THE INVENTION

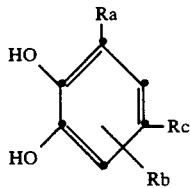

Ia wherein Ra is nitro or cyano, Rb is hydrogen or halogen, Rc is halogen, nitro, cyano or the group $-(A)_n-(Q)_m-R^1$ or $-(A)_n-Q-R^2$, A is vinylene optionally substituted by lower alkyl, n is the integer 0 or 1, m is the integer 0 or 1 $R^1$ is the group $-COR^3$, an aromatic carbocyclic group, or an aromatic or partially unsaturated heterocyclic group attached via a carbon atom, $R^2$ is hydrogen or an optionally substituted, saturated or partially unsaturated lower hydrocarbon residue, $R^3$ is hydroxy, amino, an optionally substituted, saturated or partially unsaturated, lower hydrocarbon residue attached via an oxygen atom or an imino or lower alkylimino group or a saturated, N-containing heterocyclic group attached via a ring nitrogen atom, Q is the group $-CO-$ or $>C=N-(Z-)_p-R^4$, Z is an oxygen atom or an imino group, P is the integer 0 or 1 and $R^4$ is hydrogen or saturated or partially unsaturated, lower hydrocarbon residue which is optionally substituted and which is optionally attached via a carbonyl group, including the ester and derivatives thereof which are hydrolyzable under physiological conditions and the pharmaceutically acceptable salts thereof. The compounds of formula Ia possess valuable pharmacological properties. In particular, these compounds inhibit the enzyme catechol-O-methyltransferase (COMT), a soluble, magnesium-dependent enzyme which catalyzes the transference of the methyl group of S-adenosylmethionine to a catechol substrate, whereby the corresponding methyl ethers are formed. Suitable substrates which can be O-methylated by COMT and which can thus be deactivated are, for example, extraneuronal catecholamines and exogeneously-administered therapeutically active substances having a catechol structure.

The compounds of formula Ia above can accordingly be used in the prevention or control of illnesses in which a deactivation of extraneuronal catecholamines by COMT plays a role, for example, in the prevention or control of depressions. In this case the compounds of formula Ia above can be used as individual compounds or in combination with other therapeutically active substances which favorably influence the course of the illness. The compounds of formula Ia can, however, also be used as co-medications with other therapeutically active substances.

The compounds of formula Ia can, however, also be used to improve the prevention or control of illnesses with therapeutically active substances which have a catechol structure. The treatment of Parkinson's disease and of parkinsonism with L-dopa, a therapeutically active substance having the catechol structure, can be mentioned as an example. In such cases the compounds of formula Ia can be used in the form of a co-medication or as combination preparations.

The field of diagnostics offers a further possibility for the use of the compounds of formula Ia above. After the administration of [$^{18}$F]-6-fluoro-L-dopa, [$^{18}$F]-dopamine in the brain can be visualized with the aid of positron emission tomography. By adding a compound of formula Ia above, the COMT is inhibited and thus the formation of [$^{18}$F]-3-O-methyldopa is prevented. In the absence of a COMT-inhibitor, the [$^{18}$F]-3-O-methyldopa would penetrate into the brain and lead to a greatly increased background which would made the diagnosis very much more difficult.

Formula Ia above embraces not only known, but also compounds which form part of the invention. The compounds of formula Ia which are known fall under the formula

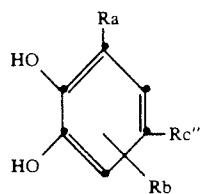

Ia$^1$ wherein Ra is nitro or cyano, Rb is hydrogen or halogen, Rc″ is nitro, cyano or the group —(A)$_n$—COOH or —(A)$_n$—Q—H, A is vinylene optionally substituted by lower alkyl, n is the number 0 or 1, Q is the group —CO— or >C=N—(Z)$_p$—R$^4$, Z is an oxygen atom or an imino group, p is the number 0 of 1 and R$^4$ is hydrogen or a saturated or partially unsaturated lower hydrocarbon residue which is optionally substituted and which is optionally attached via a carbonyl group, with the proviso that Ra is nitro when Rc″ is cyano or nitro, and ester and ether derivatives thereof which are hydrolyzable under phydiological conditions and the pharmaceutically acceptable salts thereof.

The compounds of formula Ia which form part of the invention are the compounds of the formula

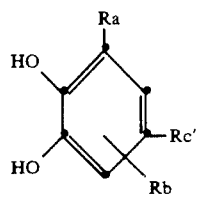

Ib wherein Ra is nitro or cyano, Rb is hydrogen or halogen, Rc′ is nitro, cyano or the group —(A)$_n$—(Q)$_m$—R$^{11}$ or —(A)$_n$—Q—R$^{21}$, A is vinylene optionally substituted by lower alkyl, n is the number 0 or 1, m is the number 0 or 1, R$^{11}$ is the group —COR$^{31}$, an aromatic carbocyclic group, or an aromatic or partially unsaturated heterocyclic group attached via a carbon atom, R$^{21}$ is an optionally substituted, saturated or partially unsaturated lower hydrocarbon residue, R$^{31}$ is hydroxy, amino, an optionally substituted, saturated or partially unsaturated, lower hydrocarbon residue attached via an oxygen atom or an imino or lower alkylimino group or a saturated, N-containing heterocyclic group attached via a ring nitrogen atom, Q is the group —CO— or >C=N—(Z)$_p$—R$^4$, Z is an oxygen atom or an imino group, P is the number 0 or 1 and R$^4$ is hydrogen or saturated or partially unsaturated, lower hydrocarbon residue which is optionally substituted and which is optionally attached via a carbonyl group, with the proviso that Ra is cyano when Rc′ is cyano or nitro and R$^{31}$ has a significance different from hydroxy when m is the number 0, and the ester and ether derivatives thereof which are hydrolyzable under physiological conditions and the pharmaceutically acceptable salts thereof.

Objects of the invention are: The above compounds of formula Ia and the mentioned derivatives thereof for use as therapeutically active substances; medicaments based on these compounds and derivatives; the preparation of such medicaments; the use of the compounds and derivatives in question in the prevention or control of illnesses; the use of the compounds and derivatives in question for the preparation of medicaments which in a given case inhibit the enzyme COMT in the sense of a desired side-effect; the compounds of formula Ib above and the mentioned derivatives thereof; the preparation of these compounds and derivatives; as well as intermediates for their preparation.

The term "lower" denotes residues and compounds with a maximum of 7, preferably a maximum of 4, carbon atoms. The term "alkyl", taken along or in combinations, such as, "alkyl group", "alkoxy", "alkylthio" and "alkylimino", denotes straight-chain or branched, saturated hydrocarbon residues, for example, such as methyl, ethyl, propyl, isopropyl, n-butyl, s-butyl, i-butyl, t-butyl and the like. The term "saturated or partially unsaturated lower hydrocarbon residue" denotes open-chain and cyclic groups and combinations thereof. Examples of saturated and partially unsaturated lower hydrocarbon residues are: lower alkyl groups such as those defined above; lower alkenyl groups, for example, 2-propenyl, 2-butenyl, 3-butenyl and 2-methyl-2-propenyl; C$_{3-7}$-cycloalkyl and C$_{8-10}$-bicycloalkyl groups optionally substituted by lower alkyl groups, for example, cyclopropyl, cyclopentyl, 2-methylcyclopentyl, cyclohexyl and 3-methylcyclohexyl; lower cycloalkenyl groups optionally substituted by lower alkyl groups, for example, 3-cyclopentenyl, 1-methyl-3-cyclopentenyl and 3-cyclohexenyl; lower alkyl or alkenyl groups substituted by lower cycloalkyl or cycloalkenyl groups, for example, cyclopropylmethyl, cyclopropylethyl, cyclopentylmethyl, cyclohexylmethyl, 2-cyclohexenylmethyl and 3-cyclopropyl-2-propenyl. The lower alkenyl groups preferably contain 2–4 carbon atoms; the cycloalkyl and cycloalkenyl groups preferably contain 3–6 carbon atoms.

The following come into consideration as substituents for the above lower hydrocarbon residues: Hydroxy, cyano, nitro, halogen, amino, lower alkylamino, di(lower alkyl)-amino, lower alkoxy, lower alkoxycarbonyl, aryl, arylaminocarbonyl, arylcarbonyl, arylcarbonylamino, lower alkanoyloxy, lower alkanoyl, carbamoyl, mono- or di(lower alkyl)carbamoyl, lower alkylenedioxy, trifluoromethyl, carboxy, lower alkanoylamino, lower alkoxycarbonylamino and lower alkylthio. The saturated or partially unsaturated lower hydrocarbon residues are preferably unsubstituted or mono- or disubstituted.

The term "aryl" denotes carbocyclic aromatic groups, preferably mono- or bicyclic groups. Especially preferred carbocyclic aromatic groups are phenyl and naphthyl, especially phenyl. These groups are optionally substituted by: halogen, trifluoromethyl, nitro, amino, mono- or di(lower alkyl)amino, lower alkyl, lower alkoxy, lower alkylthio, lower alkanoyl, lower alkoxycarbonyl, carboxy, hydroxy, cyano, lower alkanoyloxy, carbamoyl, mono- or di(lower alkyl)carbamoyl, lower alkylenedioxy, lower alkanoylamino or lower alkoxycarbonylamino. The carbocyclic aromatic groups are preferably unsubstituted or mono- or disubstituted.

The term "aromatic or partially unsaturated heterocyclic group" preferably denotes a mono-, di- or tricyclic, aromatic or partially unsaturated, heterocyclic group with up to 5 hetero atoms from the group consisting of nitrogen, sulfur and oxygen. The heterocyclic groups preferably contain 1–4 nitrogen atoms and/or an oxygen or sulfur atom. They are preferably mono- or bicyclic. The hetero atoms are preferably distributed on one or two rings, whereby nitrogen atoms can simultaneously also be components of 2 rings. The heterocyclic groups are preferably aromatic. They can be substituted and are preferably mono-, di- or trisubstituted. As substituents there come into consideration: halogen, trifluoromethyl, nitro, carboxy, amino, arylamino, lower alkyl, lower alkoxy, hydroxy, lower alkoxycarbonyl, lower alkanoyl, lower alkanoyloxy, oxo, lower alkylenedioxy, mercapto, lower alkylthio, lower alkylamino, di(lower alkyl)amino, $C_{3-7}$-cycloalkylamino. $C_{8-10}$-bicycloalkylamino, lower alkanoylamino, lower alkoxycarbonylamino, carbamoyl, mono- or di(lower alkyl)carbamoyl, cyano, aryl, aryl-lower alkyl, aryl-lower alkylamino, heteroaryl, heteroaryl-lower alkyl, heteroarylamino and $C_{3-7}$-cycloalkyl. The monocyclic heterocyclic groups are preferably 5- or 6-membered and contain a maximum of four hetero atoms. The bicyclic heterocyclic groups are preferably 8- to 10-membered, with the individual rings being preferably 5- or 6-membered.

The following are to be mentioned as examples of such heterocyclic groups: Pyridyl, pyrazinyl, triazinyl, thiadiazinyl, thiazolyl, oxazolyl, oxadiazolyl, pyrazolyl, tetrazolyl, imidazolyl, thienyl, quinolinyl, isoquinolinyl, dihydroisoquinolinyl, benzoxazinyl, quinoxalinyl, benzopyranyl, benzimidazolyl, indolyl, imidazothiazolyl, imidazothiadiazolyl, imidazopyridyl, benzothiazinyl, benzoquinoxalinyl and imidazobenzothiazolyl.

The term "heteroaryl" denotes aromatic heterocyclic groups, as defined above.

The term "a saturated, N-containing heterocyclic group attached via a ring nitrogen atom" preferably denotes a 3- to 7-membered, preferably 4- to 6-membered, saturated N-heterocycle which, in addition to the said nitrogen atom, can contain an oxygen, sulfur or nitrogen atom as a second hetero atom. These saturated N-heterocycles can be mono- or disubstituted by: lower alkyl, hydroxy, lower alkoxy, lower alkanoyloxy, lower hydroxyalkyl, lower alkoxyalkyl, lower alkanoyloxyalkyl, lower alkoxycarbonyl, lower alkanoyl, carbamoyl, mono- or di(lower alkyl)carbamoyl, oxo and/or lower alkylenedioxy.

The following are to be mentioned as examples of such N-containing heterocyclic groups: 4-morpholinyl, 1-pyrrolidinyl and 1-azetidinyl.

The ester and ether derivatives which are hydrolyzable under physiological conditions are preferably compounds of formula Ia in which at least one of the two phenolic hydroxy groups is acylated by a lower fatty acid or etherified by a lower 1-alkoxycarbonyloxy-1-alkyl, lower 1-alkanoyloxy-1-alkyl or by a lower 2-oxo-1-alkyl group.

The substituent Ra preferably is nitro. The substituent Rb is preferably situated in the p-position to the substituent Ra and preferably is hydrogen, chlorine or fluorine, with hydrogen being especially preferred. The substituent Rc' preferably is the group —CO—$R^{11}$ in which $R^{11}$ is an aromatic, mononuclear carbocyclic group or an aromatic, mononuclear heterocyclic group with 1–3 nitrogen atoms as the hetero ring member(s) which is attached via a carbon atom. In an especially preferred embodiment $R^{11}$ is a phenyl group optionally mono- or disubstituted by halogen, trifluoromethyl, cyano, hydroxy or lower alkyl, or a pyridyl group.

Particularly preferred compounds of the invention are:

3,4-Dihydroxy-5-nitrobenzophenone,
2'-fluoro-3,4-dihydorxy-5-notribenzophenone and
3,4-dihydroxy-5-nitrophenyl 4-pyridyl ketone.

The compounds of formula Ib, the ester and ether derivatives thereof which are hydrolyzable under physiological conditions and the pharmaceutically acceptable salts thereof can be prepared in accordance with the invention by a) cleaving the lower alkyl ether group(s) in a compound of the formula

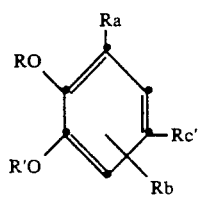

II wherein one of the symbols R and R' is lower alkyl and the other is hydrogen or lower alkyl and Ra, Rb and Rc' have the above significance, or b) reacting a compound of the formula

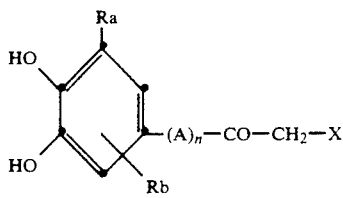

wherein X is a leaving group and Ra, Rb, A and n have the above significance,
with a thioamide, thiourea, thiocarboxylic acid hydrozide, thiosemicarbozide, amidine, guanidine, amidrazone, aminoguanidine, cyclic amidine, 1,2-diamine, 1,2-aminothiol or a 1,2-aminoalcohol and, if desired, dehydrogenating the cyclocondensation product obtained or c) reacting a compound of the formula

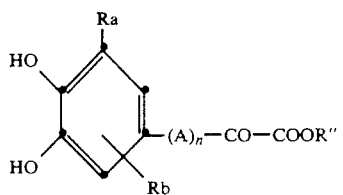

wherein R'' is lower alkyl and Ra, Rb, A and n have the above significance,
with a 1,2-diamine, 1,2-aminothiol, 1,2-aminoalcohol, semicarbazide, thiosemicarbazide, amidrazone or an aminoguanidine and, if desired, dehydrogenating the cyclocondensation product obtained, or d) reacting a compound of formula Ib¹ above with a β-aminocarbonyl compound, or e) converting the carboxaldehyde group(s) in a compound of the formula

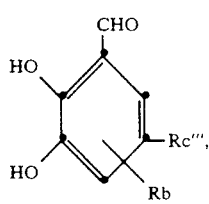

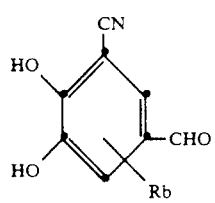

or

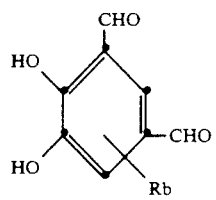

wherein Rc'', is nitro, cyano or the group —(A)ₙ—R¹² and R¹² is the group —COR³¹, an aromatic carbocyclic group, or an aromatic or partially unsaturated heterocyclic group attached via a carbon atom and Ra, Rb, A, n and R³¹ have the above significance,
or in a di-O-lower alkanoyl derivative thereof into the cyano group(s), or f) reacting a di-O-lower alkanoyl derivative of a carboxylic acid of the formula

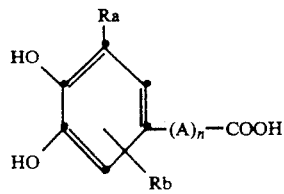

or

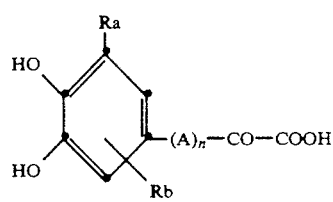

wherein Ra, Rb, A and n have the above significance, in the presence of a condensation agent or a reactive derivative or a di-O-lower alkanoyl derivative of a carboxylic acid of formula Ia³ or Ib³ with a compound of the formula $$HO—R^5 \quad V$$

or $$HNR^6R^7 \quad VI$$

wherein R⁵ is an optionally substituted, saturated or partially unsaturated, lower hydrocarbon residue, R⁶ is hydrogen or lower alkyl and R⁷ is hydrogen or an optionally substituted, saturated or partially unsaturated lower hydrocarbon residue or R⁶ and R⁷ taken together with the nitrogen atom signify a saturated N-containing heterocyclic group, or g) hydrolyzing a compound of formula Ib² or a compound of the formula

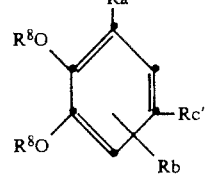

wherein R⁸ is lower alkanoyl and Ra, Rb and Rc' have the above significance, h) reacting a compound of the formula

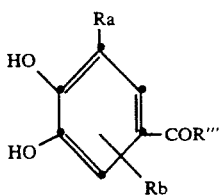

wherein Ra and Rb have the above significance and R''' is hydrogen or lower alkyl, or a di-O-lower alkanoyl derivative thereof in the presence of a secondary amine with a compound of the formula

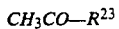

wherein $R^{23}$ is an optionally substituted, saturated or partially unsaturated lower hydrocarbon residue, or i) reacting a compound of the formula

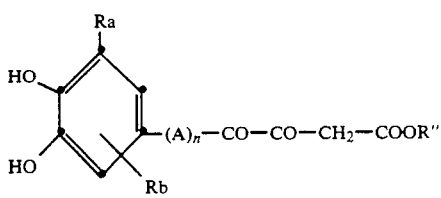

wherein Ra, Rb, A, n and R'' have the above significance,
with a hydrazine or an amidine, or j) reacting a compound of formula Ib above in which m is the integer 1 and Q is the group —CO— with a compound of the formula

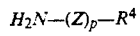

wherein Z, p and $R^4$ have the above significance, and, if desired, k) converting a compound of formula Ib above into an ester or ether derivative which is hydrolyzable under physiological conditions or into a pharmaceutically acceptable salt thereof.

In accordance with process variant a) the compounds of formula Ib can be prepared by cleaving the ether group(s) in a compound of formula II. This ether cleavage can be carried out according to known methods which are familiar to any person skilled in the art. The ether cleavage can be carried out, for example, by treatment with hydrogen bromide in a suitable solvent. Suitable solvents are, for example, water, acetic acid and mixtures thereof. The reaction is preferably carried out at an elevated temperature, for example in a temperature range of about 100° C. to the boiling temperature of the reaction mixture. There are preferably used 48 percent hydrobromic acid or mixtures thereof with acetic acid.

The ether cleavage can also be carried out by treatment with boron tribromide in a suitable solvent at temperatures of about −60° C. to about room temperature. Suitable solvents are especially halogenated lower hydrocarbons, such as, methylene chloride, chloroform and the like. Other suitable methods are: treatment with pyridinium hydrochloride at temperatures of about 150° C. to about 250° C. and treatment with sodium iodide/solicon tetrachloride in an inert organic solvent at an elevated temperature, for example, at the reflux temperature of the reaction mixture. Suitable solvents for the latter process are, for example, acetonitrile, aromatic hydrocarbons, such as, benzene or toluene, mixtures thereof and the like.

In accordance with process variant b) there can be prepared compounds of the formula

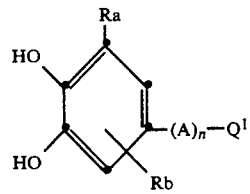

wherein Ra, Rb, A and n have the above significance and $Q^1$ is a group of the formula

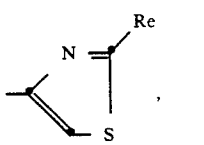

(a)

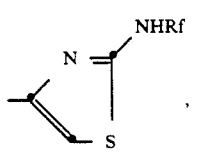

(b)

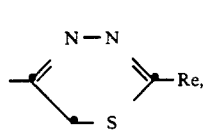

(c)

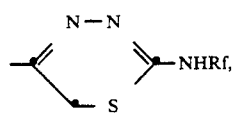

(d)

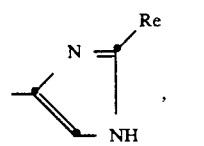

(e)

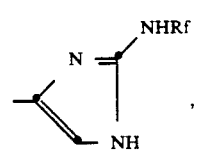

(f)

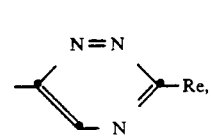

(g)

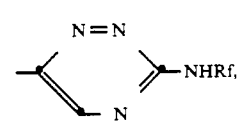

(h)

-continued

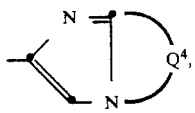  (i)

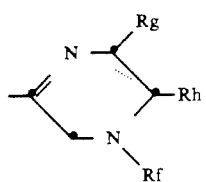  (k)

or

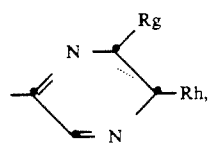  (k')

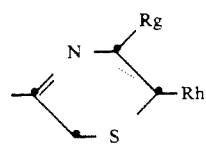  (l)

or

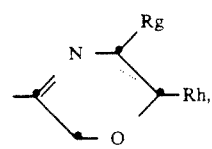  (m)

in which Re is hydrogen, $C_{3-7}$-alkyl, $C_{3-7}$-cycloalkyl, aryl, heteroaryl, aryl-lower alkyl or heteroaryl-lower alkyl, Rf is hydrogen, aryl, aryl-lower alkyl, lower alkyl, lower alkoxycarbonyl, heteroaryl, heteroaryl-lower alkyl, $C_{8-10}$-bicycloalkyl or $C_{3-7}$-cycloalkyl, Rg and Rh each are independently hydrogen, cyano, lower alkyl, $C_{3-7}$-cycloalkyl, aryl, aryl-lower alkyl, heteroaryl or heteroaryl-lower alkyl or Rg and Rh taken together with the two carbon atoms to which they are attached are an aromatic carboxycyclic group, or an aromatic or partially unsaturated heterocyclic group, the dotted line is an optional bond and $Q^4$ taken together with the carbon atom and the nitrogen atom signify an aromatic or partially unsaturated, heterocyclic group which contains at least one nitrogen atom as a hetero ring member.

Suitable solvents for this process aspect are lower alcohols such as ethanol, n-butanol, n-hexanol and ethylene glycol, open-chain and cyclic ethers which can contain free hydroxy groups, for example, tetrahydrofuran, dioxane, t-butyl methyl ether, ethylene glycol dimethyl ether, diethylene glycol dimethyl ether, ethylene glycol monomethyl ether and diethylene glycol monomethyl ether, acetonitrile, dimethylformamide, dimethylacetamide and dimethyl sulfoxide. The desired reaction can also be carried out without a solvent by dry heating the reaction partners. The reaction is preferably carried out an at elevated temperature, for example, in a range of about 50° C. to 150° C., whereby it is preferably carried out at the boiling temperature of the solvent insofar as it is carried out in the presence of a solvent and the boiling point lies in the previously mentioned range.

In accordance with process variant c) there can be prepared compounds of the formula

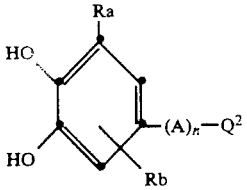  Ib$^8$ in which Ra, Rb, A and n have the above significance and $Q^2$ is a group of the formula

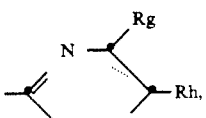  (n)

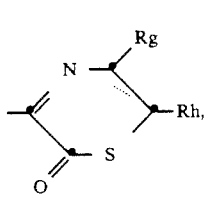  (o)

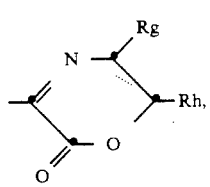  (p)

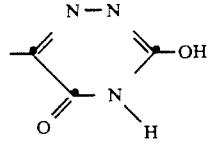  (q)

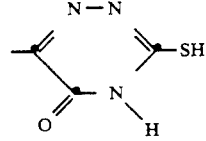  (r)

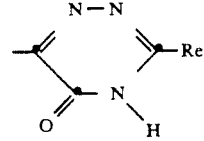  (s)

or

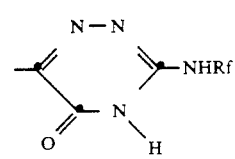  (t)

in which Re, Rf, Rg, Rh and the dotted line have the above significance.

The reaction in accordance with process variant c) can be carried out under the same reaction conditions as process variant b).

In accordance with process variant d) there can be prepared compounds of the formula

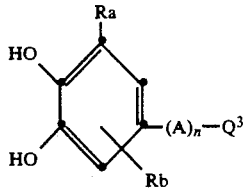

Ib⁹ wherein $Q^3$ is the group of the formula

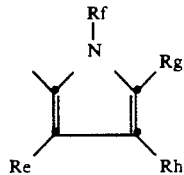

(u)

and Ra, Rb, Re, Rf, Rg, Rh, A, n and the dotted line have the above significance.

Process variant d) can also be carried out under the same reaction conditions as process variant b).

In accordance with process variant e) there can be prepared compounds of formula Ib in which Ra is cyano, Rc' is nitro, cyano or the group $-(A)_n-R^{12}$ and $R^{12}$ is the group $-COR^{31}$, an aromatic carbocyclic group or an aromatic or partially unsaturated heterocyclic group attached via a carbon atom and Rb, A, n and $R^{31}$ have the above significance. The conversion of the carboxaldehyde group(s) into the cyano group(s) can be effected according to known methods which are familiar to any person skilled in the art. For example, a compound of formula Ia². III or IV can be treated with hydroxylamine O-sulfonic acid at an elevated temperature, with water being preferably used as the solvent. The reaction can be carried out in a temperature range of about 50° C. to about 100° C.

In accordance with process variant f) there can be prepared di-O-lower alkanoyl derivatives of compounds of formula Ib in which Rc' is the group $-(A)-_n-(CO)_m-COR^{32}$ and $R^{32}$ is amino, an optionally substituted, saturated or partially unsaturated, lower hydrocarbon residue attached via an oxygen atom or an imino or lower alkylimino group or a saturated, N-containing heterocylic group attached via a ring nitrogen atom and A, n and m have the above significance. This reaction can also be carried out according to known methods which are familiar to any person skilled in the art. Lower alkyl esters can be prepared, for example, by treating the carboxylic acid with the corresponding lower alcohol in the presence of an acid, with the corresponding lower alcohol being preferably used as the solvent. Suitable acids are, for example, mineral acids such as hydrogen chloride and organic sulfonic acids such as p-toluenesulfonic acid. The reaction temperature preferably lies in a range of room temperature to the boiling temperature of the chosen solvent.

The remaining esters and the amides are preferably prepared starting from reactive carboxylic acid derivatives. Suitable reactive carboxylic acid derivatives are, for example, the corresponding carboxylic acid halides, especially the carboxylic acid chlorides, corresponding carboxylic acid anhydrides and mixed anhydrides, for example, with trifluoroacetic acid and organic sulfonic acids such as mesitylenesulfonic acid and p-toluenesulfonic acid, corresponding carboxylic acid imidazolides and the like. The reaction is conveniently carried out in the presence of an acid-binding agent and in an inert organic solvent. Suitable acid-binding agents are, for example, tertiary amines such as triethylamine and pyridine. In the preparation of amides, excess amine of formula VI can also be used as the acid-binding agent. Suitable solvents are, for example, open-chain and cyclic ethers such as tetrahydrofuran, diethyl ether, t-butyl methyl ether, dioxane, ethylene glycol, dimethyl ether or the like, halogenated hydrocarbons such as methylene chloride, chloroform and 1,2-dichloroethane, acetonitrile and dimethylformamide.

The hydrolysis of compounds of formula Ib⁴ to the corresponding catechol derivatives in accordance with process variant g) can also be carried out according to known methods which are familiar to any person skilled in the art. The hydrolysis can be carried out, for example, by treatment with an alkali metal hydroxide such as sodium hydroxide or potassium hydroxide in a suitable solvent. Suitable solvents are, for example, lower alcohols such methanol and water or mixtures thereof. The hydrolysis can be carried out, for example, in a temperature range of about 0° C. to the boiling temperature of the solvent. However, it is preferably carried out at room temperature.

In accordance with process variant h) there can be prepared compounds of the formula

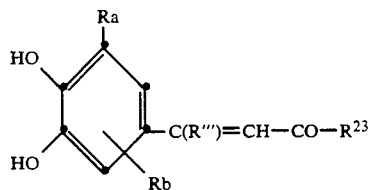

Ib¹⁰ wherein Ra, Rb R''' and $R^{23}$ have the above significance, and the corresponding di-O-lower alkanoyl derivatives thereof. Cyclic amines such as pyrrolidine, piperidine, morpholine and thiomorpholine are preferably used as the secondary amine. Suitable solvents for this process are, for example, open-chain and cyclic ethers such as tetrahydrofuran, diethyl ether, t-butyl methyl ether, dioxane, ethylene glycol and dimethyl ether, halogenated hydrocarbons such as methylene chloride, chloroform and 1,2-dichloroethane, acetonitrile and dimethylformamide. The reaction temperature conveniently lies in a range of about 0° C. to the boiling temperature of the chosen solvent. The reaction is preferably carried out at room temperature. In an especially preferred embodiment the reaction is carried out in the presence of an acid, preferably a carboxylic acid such as acetic acid.

In accordance with process variant i) there can be prepared compounds of the formula

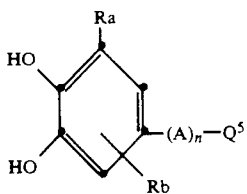

Ib¹¹ wherein Q⁵ is the group

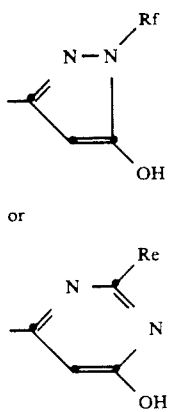

and Ra, Rb, Re, Rf, A and n have the above significance.

Suitable solvents for this process are, for example, lower alcohols such as methanol and ethanol, open-chain and cyclic ethers such as tetrahydrofuran, diethyl ether, t-butyl methyl ether, dioxane, ethylene glycol and dimethyl ether, acetonitrile and dimethylformamide. The reaction is preferably carried out at an elevated temperature, for example in a range of about 50° C. to the boiling temperature of the chosen solvent. It is preferably carried out at the boiling temperature of the chosen solvent.

In accordance with process variant j) there can be prepared compounds of the formula

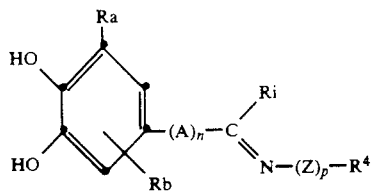

Ib¹² wherein Ri is the group —COR³¹, an aromatic carbocyclic group, or an aromatic or partially unsaturated heterocyclic group attached via a carbon atom or an optionally substituted, saturated or partially unsaturated lower hydrocarbon residue and Ra, Rb, R³¹, R⁴, A, Z, n and p have the above significance.

This process can also be carried out according to know methods which are familiar to any person skilled in the art. Suitable solvents are, for example, lower alcohols such as methanol and ethanol, dimethylformamide and water. The reaction is conveniently carried out at room temperature.

In accordance with process variant k), the compounds of formula Ib can be converted into ester or ether derivatives which are hydrolyzable under physiological conditions. Suitable ester derivatives which are hydrolyzable under physiological conditions are especially the compounds of formula Ib in which ate last one of the two phenolic hydroxy groups is acylated by a lower fatty acid. These can be prepared according to known methods which are familiar to any person skilled in the art. In a preferred embodiment, the acylation is carried out with the corresponding lower fatty acid anhydride in the presence of a catalytic amount of a strong acid, with excess fatty acid anhydride being preferably used as the solvent. Suitable acids are, for example, sulfuric acid and organic sulfonic acids such as p-toluenesulfonic acid.

Suitable ether derivatives which are hydrolyzable under physiological conditions are, for example, compounds of formula Ib in which at least one of the two phenolic hydroxy groups is etherified by a lower 1-alkoxycarbonyl-oxy-1-alkyl, lower 1-alkanoyloxy-1-alkyl or by a lower 2-oxo-1-alkyl group. The etherification can be carried out according to known methods which are familiar to any person skilled in the art. For example, a compound of formula Ib can be reacted with a lower 1-alkoxycarbonyloxy-1-alkyl halide, a lower 1-alkanoyloxy-1-alkyl halide or a lower 2-oxo-1-alkyl halide, with this etherification being conveniently carried out in the presence of a base. As halides there come into consideration, in particular, the iodides. Suitable bases are, for example, alkali metal hydroxides and alkali metal carbonates such as sodium hydroxide and sodium carbonate.

In accordance with process variant k), compounds of formula Ib above can also be converted into pharmaceutically acceptable salts. As salts there come into consideration, in particular, salts with pharmaceutically acceptable bases. As examples of such salts there are to be mentioned the alkali metal salts such as the sodium and potassium salts. These salts can be prepared according to known methods which are familiar to any person skilled in the art.

The various compounds which are used as starting materials are known or can be prepared according to known methods. The Examples which follow contain detailed information concerning the preparation of the starting materials.

As mentioned earlier, the compounds of formula Ia inhibit the enzyme COMT. This activity can be determined quantitatively as follows: Rat liver homogenate is incubated in the presence of a suitable substrate as described in J. Neurochem. 38, 191–195 (1982) and the COMT activity is measured. In a second series of experiments the incubation is carried out in the presence of a compound of formula Ia. The $IC_{50}$ can then be calculated from the difference of the COMT activity which is determined. $IC_{50}$ is given in nmol/l and is that concentration in the incubation mixture which is required to reduce the COMT activity by 50%. The $IC_{50}$ values for some compounds of formula Ia are given in the following Table. Moreover, this Table contains data concerning the acute toxicity of these compounds ($LD_{50}$ in mg/kg in the case of single oral administration to mice).

| Compound of formula Ia | $IC_{50}$ in nmol/l | $LD_{50}$ in mg/kg p.o. |
|---|---|---|
| 3,4-Dihydroxy-5-nitrophenyl 2-pyridyl ketone | 53.4 | 1250–2500 |
| 3,4-Dihydroxy-5-nitrophenyl 3-pyridyl ketone | 47.0 | 1000–2000 |

-continued

| Compound of formula Ia | IC$_{50}$ in nmol/l | LD$_{50}$ in mg/kg p.o. |
|---|---|---|
| 3,4-Dihydroxy-5-nitrophenyl 4-pyridyl ketone | 67.0 | 1000–2000 |
| n-Butyl 3,4-dihydroxy-5-nitrobenzoate | 20.0 | 312–625 |
| n-Butyl 3,4-dihydroxy-5-nitrocinnamate | 25.9 | 2500–5000 |
| Ethyl 3,4-dihydroxy-5-nitrophenylglyoxylate | 48.1 | 1250–2500 |
| 3,4-Dihydroxy-5-nitrobenzophenone | 48.0 | 500–1000 |
| 3,5-Dinitropyrocatechol | 36.9 | 500–1000 |
| 2'-Fluoro-3,4-dihydroxy-5-nitrobenzophenone | 42.0 | 312–625 |

The compounds of formula Ia, ester or ether derivatives thereof, and salts thereof can be used as medicaments, for example, in the form of pharmaceutical preparations for enteral or parenteral administration. The compounds of formula Ia can be administered, for example, perorally, for example in the form of tablets, coated tablets, dragees, hard and soft gelatine capsules, solutions, emulsions or suspensions, rectally, for example, in the form of suppositories, or parenterally, for example, in the form of injection solutions.

The manufacture of the pharmaceutical preparations can be effected in a manner which is familiar to any person skilled in the art by bringing the compounds of formula Ia, optionally in combination with other therapeutically valuable substances, into a galenical administration form together with suitable, non-toxic, inert, therapeutically compatible solid or liquid carrier materials and, if desired, the usual pharmaceutical adjuvants.

As carrier materials there are suitable not only inorganic carrier materials, but also organic carrier materials. Thus, for tablets, coated tablets, dragees and hard gelatine capsules there can be used as carrier materials, for example, lactose, maize starch or derivatives thereof, talc, stearic acid or its salts. Suitable carriers for soft gelatine capsules are, for example, vegetable oils, waxes, fats and semi-solid and liquid polyols. Depending on the nature of the active substances no carriers are, however, required in the case of soft gelatine capsules. Suitable carrier materials for the preparation of solutions and syrups are, for example, water, polyols, saccharose, invert sugar and glucose. Suitable carrier materials for injection solutions are, for example, water, alcohols, polyols, glycerine and vegetable oils. Suitable carrier materials for suppositories are, for example natural or hardened oils, waxes, fats and semi-liquid or liquid polyols.

As pharmaceutical adjuvants there come into consideration the usual preserving agents, solubilizers, stabilizing agents, wetting agents, emulsifying agents, flavor-improving agents such as sweetening agents and flavoring agents, coloring agents, salts for varying the osmotic pressure, buffers, coating agents and antioxidants.

The dosage of the compounds of formula Ia, ester or ether derivatives thereof and salts thereof can vary within wide limits depending on the illness to be treated, the age and the individual condition of the patient and on the mode of administration and will, of course, be fitted to the individual requirements in each particular case. In the improvement of the treatment of Parkinson's disease and of parkinsonism with L-dopa a daily dosage of 25 mg to about 1000 mg, especially about 100 mg to about 300 mg, comes into consideration. Depending on the dosage it is convenient to administer the daily dosage in several dosage units.

The pharmaceutical preparations in accordance with the invention conveniently contain about 25 mg to about 300 mg, preferably about 50 mg to about 150 mg, of a compound of formula Ia or of an ester or ether derivative thereof which is hydrolyzable under physiological conditions or of a pharmaceutically acceptable salt thereof.

The Examples which follow further illustrate the invention. All temperatures are given in degrees Celsius.

EXAMPLE 1 a) 17.1 g of 4-hydroxy-3-methoxy-5-nitrobenzaldehyde are treated with 170 ml of constant-boiling hydrobromic acid and heated under reflux for 3.5 hours. After cooling the separated precipitate is filtered under suction, washed twice with ice-water and taken up in ethyl acetate. The organic phase is washed twice with 50 ml of sodium chloride solution each time, dried over magnesium sulfate and evaporated in a water-jet vacuum. The crystals obtained are taken up in methylene chloride, whereupon the solution is filtered over a ten-fold amount of silica gel. The material obtained is crystallized from ethyl acetate/isopropyl ether. There is obtained 3,4-dihydroxy-5-nitrobenzaldehyde in the form of yellow crystals of m.p. 142°–143°.

b) a solution of 1.7 g of hydroxylamine O-sulfonic acid in 6 ml of water is added to a solution of 1.83 g of 3,4-dihydroxy-5-nitrobenzaldehyde in 25 ml of water, subsequently stirred at 65° for 3.5 hours, cooled, the separated precipitate is filtered off under suction and taken up in ethyl acetate. The organic phase is dried over sodium sulfate and evaporated in a water-jet vacuum. The crystals obtained are recrystallized from ethyl acetate/n-hexane. There is obtained 3,4-dihydroxy-5-nitrobenzonitrile in the form of yellow crystals of m.p. 194°–195°.

EXAMPLE 2 aa) 10 ml of tert.butyl lithium solution (1.4M in hexane) are added dropwise at −70° within 10 minutes to 4.1 g of 4-(benzyloxy)-3-methoxy-bromobenzene dissolved in 40 ml of tetrahydrofuran. After stirring at −70° for 2 hours. 1 ml of pyridine-3-carbaldehyde is added within 5 minutes The reaction mixture is stirred at −70° for 1 hour and at 0° for 2 hours. and poured into 100 ml of 1N hydrochloric acid. The mixture is extracted three times with 50 ml of ether each time. The combined ether phases are washed with 100 ml of 1N hydrochloric acid and 20 nl of water. The combined aqueous phases are made alkaline with aqueous ammonia solution and extracted three times with 100 ml of methylene chloride each time. The combined methylene chloride phases are dried over sodium sulfate and evaporated. There is obtained alpha-[4-(benzyloxy)-3-methoxyphenyl]-3-pyridinemethanol as an oil.

ab) In an analogous manner, using pyridine-4-carbaldehyde there is obtained alpha-[4-(benzyloxy)-3-methoxyphenyl]-4-pyridinemethanol as an oil.

ba) 3.2 g of alpha-[4-(benzyloxy)-5-methoxyphenyl]-3-pyridinemethanol suspended in 50 ml of water are treated with 2.5 g of potassium permananate, whereupon the mixture is stirred at 90° for 30 minutes After adding a further 1.0 g of potassium permanganate and stirring for a further 30 minutes at 90° the mixture is cooled to room temperature and extracted twice with 150 ml of ethyl acetate each time. The combined ethyl acetate phases are washed with sodium chloride solution, dried over sodium sulfate and evaporated. The thus-obtained residue is chromatographed on 50 g of silica gel with ethyl acetate. After recrystallization from methylene chloride/hexane there is obtained 4-(benzyloxy)-3-methoxyphenyl 3-pyridyl ketone of m.p. 76°.

bb) In an analogous manner, from alpha-[4-(benzyloxy)-3-methoxyphenyl)-4-pyridinemethanol there is obtained 4-(benzyloxy)-3-methoxyphenyl 4-pyridyl ketone of m.p. 85°–87° (methylene chloride/hexane).

ca) 50 ml of 33 percent hydrobromic acid in acetic acid are added dropwise within 15 minutes at 10° to 20 g of 4-(benzyloxy)-3-methoxyphenyl 3-pyridyl ketone dissolved in 200 ml of methylene chloride. After stirring at 20° for 3 hours, the reaction mixture is poured into a mixture of 100 ml of conc. aqueous ammonia and ice. The pH is adjusted to 6 by adding acetic acid. The methylene chloride phase is separated; the aqueous phase is extracted twice more with 100 ml of methylene chloride each time. The combined methylene chloride phases are dried over sodium sulfate and evaporated. The residue is recrystallized from methylene chloride/hexane. There is obtained 4-hydroxy-3-methoxyphenyl 3-pyridyl ketone of m.p. 150°–151°.

cb) In an analogous manner, from 4-(benzyloxy)-3-methoxyphenyl 4-pyridyl ketone there is obtained 4-hydroxy-3-methoxyphenyl 4-pyridyl ketone of m.p. 215°–218° (acetonitrile).

da) 0.38 ml of 65 percent nitric acid is added dropwise at room temperature to 1.15 g of 4-hydroxy-3-methoxyphenyl 3-pyridyl ketone dissolved in 15 ml of acetic acid. After stirring for 2 hours, the reaction mixture is poured into 120 ml of ice-water, whereupon the mixture is adjusted to pH 5 with conc. ammonia and the precipitate formed is filtered off. The thus-obtained residue is heated under reflux in 20 ml of acetonitrile, whereupon it is again filtered off. There is obtained 4-hydroxy-3-methoxy-5-nitrophenyl 3-pyridyl ketone as brown crystals of m.p. 193°.

db) In an analogous manner, from 4-hydroxy-3-methoxyphenyl 4-pyridyl ketone there is obtained 4-hydroxy-3-methoxy-5-nitrophenyl 4-pyridyl ketone of m.p. 240°.

e) 3.5 g of 4-hydroxy-3-methoxy-5-nitrophenyl 3-pyridyl ketone dissolved in 70 ml of 48 percent aqueous hydrobromic acid are stirred at 100° for 18 hours. The reaction mixture is subsequently evaporated under reduced pressure. The residue is recrystallized from water. There is obtained 3,4-dihydroxy-5-nitrophenyl 3-pyridyl ketone hydrobromide of m.p. 265°.

f) In an analogous manner, from 4-hydroxy-3-methoxy-5-nitrophenyl 4-pyridyl ketone there is obtained 3,4-dihydroxy-5-nitrophenyl 4-pyridyl ketone of m.p. 246° (from water).

g) 13.2 g of 3,4-dihydroxy-5-nitrophenyl 4-pyridyl ketone are suspended in 500 ml of methanol and treated while stirring with 4.88 g of methanesulfonic acid. The suspension is heated under reflux for 60 minutes. It is subsequently cooled to 10°, the crystals are filtered under suction and washed twice with 30 ml of methanol each time. There is obtained 3,4-dihydroxy-5-nitrophenyl 4-pyridyl ketone methanesulfonate of m.p. 260°–261° (dec.).

EXAMPLE 3 a) A solution of 2.6 g of 4-hydroxy-3-methoxy-5-nitrobenzoic acid in 26 ml of constant-boiling hydrobromic acid is heated under reflux for 2 hours. After cooling the solvent is distilled in a water-jet vacuum. The crystalline residue is recrystallized from 50 ml of water at boiling temperature. There is obtained 3,4-dihydroxy-5-nitrobenzoic acid in the form of yellow crystals of m.p. 224°–226°.

b) 1.0 g of 3,4-dihydroxy-5-nitrobenzoic acid is treated with 20 ml of methanolic hydrochloric acid, stirred at 45° for 3 hours and, after removing the solvent, the residue is taken up in methylene chloride. The organic phase is washed with sodium chloride solution, dried over sodium sulfate and evaporated. The crystalline product obtained is taken up in methylene chloride and filtered over a ten-fold amount of silica gel. The material obtained is recrystallized from ethyl acetate/n-hexane. There is obtained methyl 3,4-dihydroxy-5-nitrobenzoate in the form of yellow crystals of m.p. 144°–145°.

The following esters are obtained in an analogous manner starting from 3,4-dihyroxy-5-nitrobenzoic acid:

c) Ethyl 3,4-dihydroxy-5-nitrobenzoate of m.p. 106°–107° (from ethyl acetate/n-hexane), d) n-butyl 3,4-dihydroxy-5-nitrobenzoate of m.p. 73°–74° (from methylene chloride) and e) n-hexyl 3,4-dihyroxy-5-nitrobenzoate of m.p. 44°–45° (from isopropyl ether).

EXAMPLE 4 a) 25 ml of 2M phenyl lithium solution (in benzene/ether (7:3)) are added dropwise within 15 minutes to 10.0 g of 3,4-dimethoxy-5-nitrobenzaldehyde dissolved in 150 ml of tetrahydrofuran and the mixture stirred at 0° for 1 hour and at 20° for 2 hours. The mixture is subsequently treated with 150 ml of 2N sulfuric acid and extracted three times with 150 ml of ether. The combined ether phases are washed with sodium chloride solution, dried over sodium sulfate and evaporated. The thus-obtained residue is chromatographed on 180 g of silica gel with methylene chloride. There is obtained 3,4-dimethoxy-5-nitrobenzhydrol as an amorphous solid.

b) 2.5 g of 3,4-dimethoxy-5-nitrobenzhydrol dissolved in 50 ml of methylene chloride are treated with 2.2 g of pyridinium chlorochromate, whereupon the mixture is stirred at room temperature for 2 hours. The insoluble constituents are subsequently filtered. The filtrate is evaporated and the residue is chromatographed on 60 g of silica gel with ethylene chloride. After crystallization from methylene chloride/hexane there is obtained 3,4-dimethoxy-5-nitrobenzophenone of m.p. 78°–80°.

c) 0.5 g of 3,4-dimethoxy-5-nitrobenzophenone is stirred at 100° for 30 hours in a mixture of 4 ml of acetic acid and 4 ml of 48 percent aqueous hydrobromic acid. The reaction mixture is subsequently evaporated to dryness. The residue is taken up in methylene chloride. It is washed with water, dried over sodium sulfate and evaporated. After recrystallization from methylene chloride/hexane there is obtained 3,4-dihydroxy-5-nitrobenzophenone of m.p. 132°.

EXAMPLE 5 a) 4.9 g of magnesium are suspended in 15 ml of absolute ethanol and, after adding 1 ml of carbon tetra-chloride, warmed until the reaction starts. A solution of 31.8 g of diethyl malonate in 19.9 ml of absolute ethanol and 80 ml of absolute toluene is then added dropwise while stirring so that the temperature lies between 50° and 60°.

The reaction mixture is subsequently stirred at this temperature for an additional 1 hour, whereupon it is cooled to −5° and a solution of 49.3 g of 3,4-dimethoxy-5-nitrobenzoyl chloride (m.p. 82°-85°) in 300 ml of absolute toluene and 50 ml of absolute tetrahydrofuran is added dropwise so that the temperature does not exceed −5°. The mixture is subsequently stirred at room temperature overnight. After distillation of the solvent the residue is dissolved in 500 ml of ethyl acetate. The solution is treated while stirring and cooling with ice with an ice-cold solution of 12 ml of concentrated sulfuric acid in 80 ml of water. The organic phase is washed with sodium chloride solution, dried over magnesium sulfate and evaporated. The oil obtained is chromatographed on a ten-fold amount of silica gel with methylene chloride. The crystalline material obtained is recrystallized from isopropyl ether. There is obtained diethyl 3,4-dimethoxy-5-nitrobenzoylmalonate in the form of pale beige crystals of m.p. 70°.

b) 19.0 g of diethyl 3,4-dimethoxy-5-nitrobenzoylmalonate are dissolved in 100 ml of glacial acetic acid, 5 drops of concentrated sulfuric acid are added thereto and the mixture is heated under reflux for 16 hours. The acetic acid is distilled at 60° in a water-jet vacuum and the residue is treated three times with 250 ml of toluene each time, whereby it is evaporated each time. The crystalline residue is extracted with ethyl acetate. The organic phase is washed with water, dried over magnesium sulfate and evaporated. The crystals obtained are chromatographed on a 30-fold amount of silica gel with toluene. The crystalline material obtained is recrystallized from isopropyl ether. There is obtained 3,4-dimethoxy-5'-nitroacetophenone in the form of yellowish crystals of m.p. 86°-87°.

c) 2 g of 3',4'-dimethoxy-5'-nitroacetophenone are treated with 30 ml of constant-boiling hydrobromic acid and stirred at 140° for 2.5 hours. After cooling the mixture is poured into 200 ml of ice-water and extracted three times with 100 ml of ethyl acetate each time. The organic phase is washed twice with 25 ml of sodium chloride solution each time, dried over sodium sulfate and evaporated. The product obtained is filtered with ethyl acetate over a 20-fold amount of silica gel. By recrystallization of the material obtained from water there is obtained 3',4'-dihydroxy-5'-nitroacetophenone in the form of yellow crystals of m.p. 159°-160°.

The same compound is obtained starting from 4'-hydroxy-3'-methoxy-5'-nitroacetophenone by treatment with hydrobromic acid at the boiling temperature.

EXAMPLE 6 a) 100 g of guaiacol are dissolved in 136.4 g of isobutyric anhydride, treated with 120 g of anhydrous zinc chloride (whereby all passes into solution), the reaction mixture is heated to 155° and cooled after three minutes. The residue is first subjected to a steam distillation in order to remove readily volatile constituents and is then extracted three times with 500 ml of ether each time. The organic phase is washed twice with 250 ml of water each time, once with 150 ml of saturated bicarbonate solution and again with 250 ml of water, dried over sodium sulfate and evaporated in a water-jet vacuum. The brown resin obtained is distilled in a high vacuum. The distillate of b.p. 105°-120° (6.67 Pa) is dissolved in ether, whereupon the solution is treated with n-hexane until crystallization begins. The crystals obtained are recrystallized from ether/hexane. There is obtained 4'-hydroxy-3'-methoxy-2-methyl-propiophenone in the form of colorless crystals of m.p. 86°-87°.

b) 15.0 g of 4'-hydroxy-3'-methoxy-2-methyl-propiophenone are dissolved in 300 ml of glacial acetic acid and 7.65 ml of 50.5 percent nitric acid (11.2N) in 40 ml of glacial acetic acid are added dropwise thereto while stirring within 15 minutes. After 15 minutes the reaction mixture is poured into ice-water and the separated crystals are filtered under suction, washed with water and dissolved in methylene chloride. The solution is dried over sodium sulfate and evaporated. The crude product obtained is taken up on methylene chloride and filtered over 100 g of silica gel. The thus-obtained crystals are recrystallized from methylene chloride/n-hexane. There is obtained 4'-hydroxy-3'-methoxy-2-methyl-5'-nitropropiophenone in the form of yellow crystals of m.p. 85°-87°.

c) 8.0 g of 4'-hydroxy-3'-methoxy-2-methyl-5'-nitropropiophenone are treated with 64 g of pyridine hydrochloride and stirred at 180° for 45 minutes. After cooling the reaction mixture is poured into 500 ml of ice-water, whereupon it is made acid with 20 ml of 3N hydrochloric acid and extracted with methylene chloride. The organic phase is washed with water, dried over sodium sulfate and evaporated in a water-jet vacuum. After crystallization from methylene chloride/n-hexane there is obtained 3',4'-dihydroxy-2-methyl-5'-nitropropiophenone in the form of yellow crystals of m.p. 98°-99°.

EXAMPLE 7 a) 100 g of guaiacol are dissolved in 136.4 g of butyric anhydride, treated with 120 g of zinc chloride, heated for 3 minutes as given in Example 6.a and then worked-up as described there. The crude product obtained after high vacuum distillation is chromatographed with toluene on 600 g of silica gel. After recrystallization from ether/n-hexane there is obtained 4'-hydroxy-3'-methoxy-butyrophenone in the form of colorless crystals of m.p. 40°-41°.

b) 6.5 ml of 11.2N nitric acid are added dropwise to a solution of 12.7 g of 4'-hydroxy-3'-methoxybutyrophenone in 250 ml of glacial acetic acid while stirring within 10 minutes. The reaction mixture is subsequently stirred for 15 minutes, poured into ice-water, the separated precipitate is filtered under suction, washed with ice-water and taken up in methylene chloride. The methylene chloride solution is filtered over 50 g of silica gel. The material obtained is recrystallized from methylene chloride/n-hexane. There is obtained 4'-hydroxy-3'-methoxy-5'-nitrobutyrophenone in the form of yellow crystals of m.p. 92°-93°.

c) 10.2 g of 4'-hydroxy-3'-methoxy-5'-nitrobutyrophenone are treated with 80 g of pyridine hydrochloride and stirred at 200° for 40 minutes. After cooling the reaction mixture is poured into 500 ml of ice-water. The mixture is treated with 30 ml of 3N hydrochloric acid and extracted with methylene chloride. The organic phase is dried over sodium sulfate and evaporated. The crude product obtained is chromatographed with methylene chloride on 150 g of silica gel. The material obtained is recrystallized from methylene chloride/n-hexane. There is obtained 3',4'-dihydroxy-5'-nitrobutyrophenone in the form of yellow crystals of m.p. 88°-90°.

EXAMPLE 8 a) 2.25 g of 3,4-dihydroxy-5-nitrocinnamic acid are dissolved in 50 ml of methanol and hydrochloric acid gas is introduced into this solution for 10 minutes. After 1 hour 50 ml of isopropyl ether are added thereto, and the separated precipitate is filtered under suction and washed with isopropyl ether. After recrystallization from methanol/ether there is obtained methyl 3,4-dihydroxy-5-nitrocinnamate in the form of yellow crystals of m.p. 186°–187°.

b) In an analogous manner, from 3,4-dihydroxy-5-nitrocinnamic acid and butanolic hydrochloric acid solution there is obtained n-butyl 3,4-dihydroxy-5-nitrocinnamate in the form of yellowish crystals of m.p. 129°–130°.

EXAMPLE 9

5.0 g of diethyl 3,4-dimethoxy-5-nitrobenzoyl malonate are dissolved in 50 ml of absolute methylene chloride. After cooling to −20° a solution of 16.9 g of boron tribromide in 30 ml of methylene chloride is added dropwise thereto while stirring so that the temperature does not exceed −20°. The mixture is subsequently stirred at room temperature overnight. After adding 80 ml of ethanol the mixture is stirred at room temperature for 30 minutes and the solvent is subsequently distilled in a water-jet vacuum. The residue is treated with water and extracted with methylene chloride. The organic phase is washed with water, dried over sodium sulfate and evaporated. The crude product obtained is filtered with ethyl acetate over 50 g of silica gel. The crystalline residue obtained is recrystallized from methylene chloride/n-hexane. There is obtained ethyl 3,4-dihydroxy-5-nitro-benzoylacetate in the form of yellow crystals of m.p. 141°–142°.

EXAMPLE 10 a) A solution of 1.49 g of 2-phenylethylamine in 100 ml of methylene chloride is treated with 1.26 g of triethylamine. A solution of 3.0 g of 3,4-dimethoxy-5-nitrobenzoyl chloride in 100 ml of methylene chloride is added dropwise thereto while stirring, whereupon the mixture is stirred for a further 15 minutes. The organic phase is then extracted twice with 50 ml of ice-water each time, dried over sodium sulfate and evaporated in a water-jet vacuum. After recrystallization from methylene chloride/n-hexane there is obtained 3,4-dimethoxy-5-nitro-N-phenethylbenzamide in the form of pale beige needles of m.p. 121°–122°.

b) 3.6 g of 3,4-dimethoxy-5-nitro-N-phenylbenzamide are heated under reflux with 35 ml of phosphorus oxychloride under a nitrogen atmosphere for 96 hours. After distilling the excess phosphorus oxychloride in a water-jet vacuum at 60°, the residue is treated three times with 100 ml of toluene each time, with the solvent being distilled each time. The residue is taken up in methylene chloride. The organic phase is washed with water, dried over sodium sulfate and evaporated in a water-jet vacuum. The red resin obtained is chromatographed on 120 g of silica gel with methylene chloride/ethyl acetate (1:1). There is obtained 1-(3,4-dimethoxy-5-nitrophenyl)-3,4-dihydroisoquinoline in the form of a yellow resin.

c) 1.4 g of 1-(3,4-dimethoxy-5-nitrophenyl)-3,4-dihydroisoquinoline are treated with 15 ml of constant-boiling hydrobromic acid and heated to boiling under reflux under a nitrogen atmosphere for 1.5 hours. After distilling the hydrobromic acid in a water-jet vacuum, the crystalline residue is recrystallized from acetone. There is obtained 5-(3,4-dihydro-1-isoquinolinyl)-3-nitropyrocatechol hydrobromide in the form of yellow crystals of m.p. >250° (decomposition).

EXAMPLE 11 a) 5.0 g of 4-hydroxy-5-methoxy-isophthalaldehyde are treated with 50 ml of constant-boiling hydrobromic acid and heated to boiling under reflux and while stirring under an argon atmosphere for 3 hours. After cooling 50 ml of ice-water are added thereto, and the separated precipitate is filtered under suction and washed with water. The crude product is taken up in ethyl acetate and filtered over 50 g of aluminum oxide (activity grade II). The crystalline material obtained is recrystallized from ethyl acetate/n-hexane. There is obtained 4,5-dihydroxyisophthalaldehyde in the form of slightly orange crystals of m.p. 201°–202°.

b) A solution of 3.27 g of hydroxylamine O-sulfonic acid in 12 ml of water is added dropwise at 30° while stirring to a solution of 2.0 g of 4,5-dihydroxyisophthalaldehyde in 20 ml of water, whereupon the mixture is held at 65° for 10 hours. After cooling the separated precipitate is filtered under suction, washed with water and taken up in ethyl acetate. The organic phase is washed with water, dried over sodium sulfate and evaporated in a water-jet vacuum. After recrystallization from ethyl acetate there is obtained 4,5-dihydroxyisophthalonitrile in the form of yellow crystals which decompose above 300°.

EXAMPLE 12 a) A solution of 38 g of fuming nitric acid (96%) in 50 ml of glacial acetic acid is added dropwise while stirring and within 30 minutes at 20°–25° to a solution of 112.5 g of 2-bromo-4'-hydroxy-3'-methoxyacetophenone in 560 ml of glacial acetic acid. Yellow-brown crystals thereby separate. After 90 minutes the reaction mixture is poured on to 300 g of ice. The crystals are filtered under suction, washed with 1000 ml of water and dissolved in 1000 ml of methylene chloride. The organic phase is washed with saturated sodium chloride solution, dried over sodium sulfate, filtered and the filtrate is evaporated at 50° in a water-jet vacuum until crystallization begins. The crystallizate, cooled to room temperature, is removed by filtration under suction and washed with a small amount of methylene chloride. There is obtained 2-bromo-4'-hydroxy-3'-methoxy-5'-nitroacetophenone of m.p. 147°–149°.

b) Method A:

ba) A suspension of 580.1 mg of 2-bromo-4'-hydroxy-3'-methoxy-5'-nitroacetophenone in 10 ml of ethanol is treated with 443.8 mg of selenium dioxide and heated under reflux for 71 hours. Thereafter, the selenium is removed by filtration and the filtrate is evaporated. The residue is dissolved in methylene chloride, washed with saturated sodium chloride solution, dried over sodium sulfate, filtered and evaporated. There is obtained ethyl 4-hydroxy-3-methoxy-5-nitrophenylglyoxylate of m.p. 165°–167° (from ethanol).

In an analogous manner:

bb) From 2-bromo-4'-hydroxy-3'-methoxy-5'-nitroacetophenone and n-butanol there is obtained n-butyl 4-hydroxy-3-methoxy-5-nitrophenylglyoxylate of m.p. 105°–107° (from ethanol) and bc) from 2-bromo-4'-hydroxy-3'-methoxy-5'-nitroacetophenone and n-hexanol there is obtained hexyl 4-hydroxy-3-methoxy-5-nitrophenylglyoxylate of m.p. 103°–105° (from n-hexanol/petroleum ether).

c) Method B:

ca) A suspension of 29.01 g of 2-bromo-4′-hydroxy-3′-methoxy-5′-nitroacetophenone in 300 ml of tert.butanol is treated with 27.74 g of selenium dioxide and heated to boiling under reflux for 18 hours. The hot reaction mixture is suction filtered through a filter aid of diatomaceous earth while rinsing with methylene chloride. The filtrate is evaporated and the residue is suspended in 150 ml of hot methylene chloride. The crystalline precipitate is filtered under suction and washed with a small amount of methylene chloride. There is obtained 4-hydroxy-3-methoxy-5-nitrophenylglyoxylic acid of m.p. 169°–171°.

2.42 g of 4-hydroxy-3-methoxy-5-nitrophenylglyoxylic acid are dissolved in 25 ml of dry N,N-dimethylformamide, treated at room temperature with 50 mg of 4-dimethylaminopyridine and 920 mg of dry methanol, subsequently cooled to 0° with an ice-bath and 2.27 g of N,N-dicyclohexylcarbodiimide are added thereto. After 10 minutes the ice-bath is removed and the reaction mixture is stirred for a further 1 hour at room temperature. The mixture is subsequently evaporated. The residue is dissolved in ethyl acetate, whereupon insoluble urea is filtered, the filtrate is washed four times with water, dried over sodium sulfate, filtered and evaporated. There is obtained methyl 4-hydroxy-3-methoxy-5-nitrophenylglyoxylate of m.p. 155°–157° (from methylene chloride/ether).

In an analogous manner:

cb) From 4-hydroxy-3-methoxy-5-nitrophenylglyoxylic acid and ethanol there is obtained ethyl 4-hydroxy-3-methoxy-5-nitrophenylglyoxylate of m.p. 165°–167° (from ethanol) and cc) From 4-hydroxy-3-methoxy-5-nitrophenylglyoxylic acid and isopropanol there is obtained i-propyl 4-hydroxy-3-methoxy-5-nitrophenylglyoxylate of m.p. 99°–101° (from isopropanol).

d) A suspension of 17.2 g of ethyl 4-hydroxy-3-methoxy-5-nitrophenylglyoxylate in 100 of dry acetonitrile and 100 ml of dry toluene is treated with 10.53 g of sodium iodide and 11.9 g of silicon tetrachloride and heated under reflux for 47 hours. The reaction mixture is then evaporated and the residue is distilled six times with 200 ml of toluene each time. The residue obtained is partitioned between water and ether and filtered through a filter aid of diatomaceous earth. The ethereal phase is washed four times with saturated sodium chloride solution, dried over sodium sulfate, filtered and evaporated. The oily residue is treated three times with ether and active carbon. There is obtained ethyl 3,4-dihydroxy-5-nitrophenylglyoxylate of m.p. 77°–79° (from ether/n-hexane).

In an analogous manner:

e) From methyl 4-hydroxy-3-methoxy-5-nitrophenylglyoxylate there is obtained methyl 3,4-dihydroxy-5-nitrophenylglyoxylate as a yellow distillate at 145°–150° and 10.67 Pa.

f) from isopropyl 4-hydroxy-3-methoxy-5-nitrophenylglyoxylate there is obtained isopropyl 3,4-dihydroxy-5-nitrophenylglyoxylate as a yellow distillate at 155°–160° and 12.0 Pa, g) from n-butyl 4-hydroxy-3-methoxy-5-nitrophenylglyoxylate there is obtained n-butyl, 3,4-dihydroxy-5-nitrophenylglyoxylate as a yellow distillate at 160°–165° and 10.67 Pa and h) from n-hexyl 4-hydroxy-3-methoxy-5-nitrophenylglyoxylate there is obtained hexyl 3,4-dihydroxy-5-nitrophenylglyoxylate as a yellow distillate at 165°–170° and 12.0 Pa.

EXAMPLE 13

236.1 mg of n-hexyl 3,4-dihydroxy-nitrophenylglyoxylate are dissolved in 15 ml of ethanol and treated with 7.59 ml of 0.1N sodium hydroxide solution. After 1 hour the reddish-yellow solution is evaporated. The resulting sodium salt of the n-hexyl 3,4-dihydroxy-5-nitrophenylglyoxylate is crystallized from water and has a m.p. of ~300°.

EXAMPLE 14

A solution of 3.18 g of n-hexyl 3,4-dihydroxy-5-nitrophenylglyoxylate in 47.5 ml of ethanol is treated with 1.11 g of O-methylhydroxylamine hydrochloride, 1.95 g of sodium acetate and 2.5 ml of water and heated to boiling under reflux for 5 hours. Thereafter, the reaction mixture is evaporated and the residue is treated with ether and water. The organic phase is washed with saturated sodium chloride solution, dried over sodium sulfate, filtered and evaporated. The residue is chromatographed on silica gel with methylene chloride. There is obtained a 7:3 mixture of n-hexyl E- and Z-3,4-dihydroxy-5-nitrophenylglyoxylate O-methyl oxime as a reddish oil: 80 MHz NMR spectrum (CDCl$_3$): signal for O-methyl at 3.96 and 4.05 ppm.

EXAMPLE 15

A solution of 5.1 g of ethyl 3,4-dihydroxy-5-nitrophenylglyoxylate in dry methylene chloride is treated dropwise at −10° within 15 minutes with 25 g of boron tribromide. The mixture is then stirred at −10° for 1 hour and subsequently at room temperature for 17 hours. Thereafter, the reaction mixture is evaporated, the residue is treated cautiously with water and stirred at 50° for an additional 30 minutes. After cooling to room temperature, the flocculent precipitate is filtered under suction. The aqueous phase is acidified with 10 ml of 1N hydrochloric acid, extracted four times with ether, the combined organic extracts are washed four times with saturated sodium chloride solution, dried over sodium sulfate, filtered and evaporated. The crude product is filtered three times in succession in ether through a filter aid of diatomaceous earth. There is obtained 3,4-dihydroxy-5-nitrophenylglyoxylic acid of m.p. 172°–174° from isopropyl ether).

EXAMPLE 16 a) a mixture of 3.93 g of n-hexyl 3,4-dihydroxy-5-nitrophenylglyoxylate and 1.38 g of 2-aminophenol is melted at 120° while stirring. The melt crystallizes after 5 minutes. After 2 hours it is cooled and recrystallized from methanol. There is obtained 3-(3,4-dihydroxy-5-nitrophenyl)-2H-1,4-benzoxazin-2-one of m.p. 202°–204°.

In an analogous manner:

b) from n-hexyl 3,4-dihydroxy-5-nitrophenylglyoxylate and 2-amino-p-cresol there is obtained 3-(3,4-dihydroxy-5-nitrophenyl)-6-methyl-2H-1,4-benzoxazin-2-one of m.p. 233°–235° (from methanol/methylene chloride).

c) from n-hexyl 3,4-dihydroxy-5-nitrophenylglyoxylate and 2-amino-4-propylphenol there is obtained 3-(3,4-dihydroxy-5-nitrophenyl)-6-propyl-2H-1,4-benzoxazin-2-one of m.p. 200°–202° (from methanol).

d) from n-hexyl 3,4-dihydroxy-5-nitrophenylglyoxylate and 3-amino-4-hydroxybenzoic acid there is obtained 3-(3,4-dihydroxy-5-nitrophenyl)-2-oxo-2H-1,4-benzoxazine-6-carboxylic acid of m.p. 286°-287° (from acetone/petroleum ether).

e) from n-hexyl 3,4-dihydroxy-5-nitrophenylglyoxylate and 2-amino-4-chlorphenol there is obtained 6-chloro-3-(3,4-dihydroxy-5-nitrophenyl)-2H-1,4-benzoxazin-2-one of m.p. 241°-243° (from methanol).

f) from n-hexyl 3,4-dihydroxy-5-nitrophenylglyoxylate and 2-amino-4,6-dichlorophenol there is obtained 6,8-dichloro-3(3,4-dihydroxy-5-nitrophenyl)-2H-1,4-benzoxazin-2-one or m.p. 237°-239° (from ethanol/ether) and g) from n-hexyl 3,4-dihydroxy-5-nitrophenylglyoxylate and 2-amino-5-nitrophenol there is obtained 3-(3,4-dihydroxy-5-nitrophenyl)-7-nitro-2H-1,4-benzoxazin-2-one of m.p. 253°-255° (from acetonitrile/ethanol).

EXAMPLE 17 a) A mixture of 396.0 mg of n-hexyl 3,4-dihydroxy-5-nitrophenylglyoxylate and 137.6 mg of 1,2-phenylenediamine is heated to 120° for 60 minutes. Thereafter, the mixture is suspended in methanol, filtered under suction and recrystallized from N,N-dimethylformamide/water. There is obtained 3-(3,4-dihydroxy-5-nitrophenyl)-2(1H)-quinoxalinone of m.p. >300°.

In an analogous manner:

b) From n-hexyl 3,4-dihydroxy-5-nitrophenylglyoxylate and N-methyl-1,2-phenylene diamine there is obtained 1-methyl-3-(3,4-dihydroxy-5-nitrophenyl)-2(1H)-quinoxalinone of m.p. 271°-273° (from methanol).

c) from n-hexyl 3,4-dihydroxy-5-nitrophenylglyoxylate and N-propyl-1,2-phenylene diamine there is obtained 1-propyl-3-(3,4-dihydroxy-5-nitrophenyl)-2(1H)quinoxalinone of m.p. 183°-185° (from methanol).

d) from n-hexyl 3,4-dihydroxy-5-nitrophenylglyoxylate and 4,5-dimethyl-1,2-phenylenediamine there is obtained 3-(3,4-dihydroxy-5-nitrophenyl)-6,7-dimethyl-2(1H)-quinoxalinone of m.p. >300° (from N,N-dimethylformamide/water).

e) from n-hexyl 3,4-dihydroxy-5-nitrophenylglyoxylate and 4,5-dichloro-1,2-phenylenediamine there is obtained 6,7-dichloro-3-(3,4-dihydroxy-5-nitrophenyl)-2(1H)-quinoxalinone of m.p. >300° (from N,N-dimethylformamide/water), f) from n-hexyl 3,4-dihydroxy-5-nitrophenylglyoxylate and 3-chloro-5-trifluoromethyl-1,2-phenylenediamine there is obtained a 1:1 mixture of 8(and 5)-chloro-3-(3,4-dihydroxy-5-nitrophenyl)-6 (and 7)-trifluoromethyl-2(1H)-quinoxalinone of m.p. >300° (from N,N-dimethylformamide/water), g) from n-hexyl 3,4-dihydroxy-5-nitrophenylglyoxylate and 4-methoxy-1,2-phenylenediamine there is obtained a 1:1 mixture of 3-(3,4-dihydroxy-5-nitrophenyl)-6(and 7)-methoxy-2(1H)-quinoxalinone of m.p. >300° (from ethanol/ether), h) from n-hexyl 3,4-dihydroxy-5-nitrophenylglyoxylate and 4-nitro-1,2-phenylenediamine there is obtained 1:1 mixture of 3-(3,4-dihydroxy-5-nitrophenyl)-6(and 7)-nitro-2(1H)-quinoxalinone of m.p. >300° (from N,N-dimethylformamide/water) and i) from n-hexyl 3,4-dihydroxy-5-nitrophenylglyoxylate and N-hexyl-1,2-phenylenediamine there is obtained 1-hexyl-3-(3,4-dihydroxy-5-nitrophenyl)-2(1H)-quinolalinone of m.p. 152°-154° (from methanol).

EXAMPLE 18

A solution of 1.07 g of n-hexyl 3,4-dihydroxy-5-nitrophenylglyoxylate and 696.3 mg of 2,3-diaminonaphthalene in 3 ml of 1-hexanol is heated to boiling under reflux for 3 hours. The reaction mixture is then cooled and diluted with methanol. The crude product is filtered under suction and recrystallized from N,N-dimethylformamide/water. There is obtained 3-(3,4-dihydroxy-5-nitrophenyl)-benzo[g]quinoxalin-2(1H)-one of m.p. >300°.

EXAMPLE 19

A suspension of 2.05 g of n-hexyl 3,4-dihydroxy-5-nitrophenylglyoxylate and 600.8 mg of thiosemicarbazide is stirred intensively at 90° for 30 minutes. The mixture is then cooled to 40° and treated with a solution of 870.1 mg of sodium hydroxide in 15 ml of water. The solution is subsequently heated to 90° for 30 minutes, cooled to room temperature and treated dropwise with 2 ml of conc. hydrochloric acid. The crystallized-out product is filtered under suction and then dissolved in ethyl acetate. The solution is washed with saturated sodium chloride solution, dried over sodium sulfate, filtered and evaporated. There is obtained 6-(3,4-dihydroxy-5-nitrophenyl)-3-mercapto-1,2,4-triazin-5(4H)-one of m.p. 282°-284° (from ethanol).

EXAMPLE 20 aaa) A suspension of 2.9 g of 2-bromo-4'-hydroxy-3'-methoxy-5'-nitroacetophenone and 761.2 mg of thiourea in 170 ml of ethanol is treated at 60° with 820.3 mg of sodium acetate and stirred for 6 hours. The reaction mixture is then evaporated, the residue is treated with 170 ml of water and heated to 60° for 30 minutes. After cooling the product is filtered under suction and washed with water. There is obtained 4-(2-amino-4-thioazolyl)-2-methoxy-6-nitrophenol of m.p. 248°-250° (from ethanol).

In an analogous manner:

aab) From 2-bromo-4'-hydroxy-3'-methoxy-5'-nitroacetophenone and N-phenylthiourea there is obtained 4-(2-anilino-4-thiazolyl)-2-methoxy-6-nitrophenol of m.p. 185°-187° (from ether).

aba) 50 ml of 1,2-dichloroethane and 3.56 g of calcium carbonate are added to a solution of 4.88 g of 6-amino-4'-(trifluoromethyl)-hexanilide hydrochloride in 70 ml of water. The suspension is treated within 60 minutes while stirring at room temperature with a solution of 2.6 g of thiophosgene in 1.7 ml of toluene. After 16 hours the precipitate is removed by filtration under suction and the organic phase is washed with 1N hydrochloric acid and water. After drying over sodium sulfate and filtration the filtrate is evaporated. There is obtained crude 4'-(trifluoromethyl)hexananilide-6-isothiocyanate.

abb) A solution of 5.2 g of crude 4'-(trifluoromethyl)-hexananilide-6-isothiocyanate in 60 ml of ethanol is treated with 100 ml of conc. ammonia solution. After 30 minutes the reaction mixture is evaporated. The residue is dissolved in ethyl acetate, washed with water, dried over sodium sulfate, filtered and evaporated. There is obtained 1-[5-[($\alpha,\alpha,\alpha$-trifluoro-p-tolyl)carbamoyl]-pentyl]-2-thiourea of m.p. 140°-142° (from ethanol).

abc) A suspension of 666.7 mg of 1-[5-[$\alpha\alpha,\alpha$-trifluoro-p-tolyl)carbamoyl]pentyl]-2-thiourea and 580.2 mg of 2-bromo-4'-hydroxy-3'-methoxy-5'-nitroacetophenone in 50 ml of ethanol is treated at 60° with 164.2 mg of sodium acetate. A reddish-yellow solution thereby results. After 90 minutes the reaction mixture is evaporated, the residue is treated with water, the precipitate is filtered under suction and washed four times with 10 ml of water each time. There is obtained 6-[[4-hydroxy-3-methoxy-5-nitrophenyl)-2-thiazolyl)]-amino]-4'-(trifluoromethyl)hexananilide of m.p. 160°–162° (from ethanol).

ac) A solution of 29.0 g of 2-bromo-4'-hydroxy-3'-methoxy-5'-nitroacetophenone and 13.5 g of 2-aminoacetophenone in 250 ml of dry N,N-dimethylformamide is stirred at 90° for 16 hours. The reaction mixture is then evaporated to about two thirds and poured on to ice. The separated crystals are filtered under suction and dissolved in methylene chloride. The solution is washed with saturated sodium chloride solution, dried over sodium sulfate, filtered and evaporated. There is obtained 2-(4-hydroxy-3-methoxy-5-nitrobenzoyl)-3-methylindole of m.p. 195°–197° (from methylene chloride/methanol).

ada) A suspension of 14.5 g of 2-bromo-4'-hydroxy-3'-methoxy-5'-nitroacetophenone and 5.41 g of 1,2-phenylenediamine in 350 ml of methanol is treated with 4.92 g of sodium acetate and the mixture is heated to boiling under reflux for 22 hours. The reaction mixture is then evaporated, the residue is dissolved in methylene chloride, this solution is washed four times with water, dried over sodium sulfate, filtered and evaporated. There is obtained 2-(4-hydroxy-3-methoxy-5-nitrophenyl)quinoxaline of m.p. 195°–197° (from methylene chloride/methanol).

In an analogous manner:

adb) From 2-bromo-4'-hydroxy-3'-methoxy-5'-nitroacetophenone and 4,5-dimethyl-1,2-phenylenediamine there is obtained 6,7-dimethyl-2-(4-hydroxy-3-methoxy-5-nitrophenyl)quinoxaline of m.p. 207°–209° (from methylene chloride/methanol).

b) A suspension of 267.3 mg of 4-(2-amino-4-thiazolyl)-2-methoxy-6-nitrophenol in 10 ml of dry methylene chloride is treated at −20° with 1.25 g of boron tribromide. After the addition the mixture is stirred at −20° for a further 1 hour and at room temperature without cooling for 18 hours. The reaction mixture is then evaporated, the residue is treated cautiously with water and stirred at 50° for 30 minutes. After cooling to room temperature the mixture is suction filtered and the crude product is removed by filtration and washed with a small amount of water. There is obtained 5-(2-amino-4-thiazolyl)-3-nitropyrocatechol hydrobromide of m.p. 244°–246° (from methanol).

In an analogous manner:

c) From 4-(2-anilino-4-thiazolyl)-2-methoxy-6-nitrophenol there is obtained 5-(2-anilino-4-thiazolyl)-3-nitropyrocatechol of m.p. 202°–204° (from methanol), d) from 6-[4-(4-hydroxy-3-methoxy-5-nitrophenyl)-2-thiazolyl)amino]-4'-(trifluoromethyl)hexananilide there is obtained 6-[[4-(3,4-dihydroxy-5-nitrophenyl)-2-thiazolyl]amino]-4'-(trifluoromethyl)hexananilide of m.p. 214°–216° (from methanol).

e) from 2-(4-hydroxy-3-methoxy-5-nitrobenzoyl)-3-methylindole there is obtained 5-bromo-2-(3,4-dihydroxy-5-nitrobenzoyl)-3-methylindole of m.p. 265°–267° (from methanol), f) from 2-(4-hydroxy-3-methoxy-5-nitrophenyl)-quinoxaline there is obtained 2-(3,4-dihydroxy-5-nitrophenyl)-quinoxaline of m.p. 241°–243° (from methanol) and g) from 6,7-dimethyl-2-(4-hydroxy-3-methoxy-5-nitrophenyl)quinoxaline there is obtained 6,7-dimethyl-2-(3,4-dihydroxy-5-nitrophenyl)quinoxaline of m.p. 274°–276° (from methanol).

EXAMPLE 21

A mixture of 3.12 g of 2-bromo-3',4'-dihydroxy-5'-nitroacetophenone and 849.3 mg of thioacetamide are heated to boiling under reflux for 18 hours in 40 ml of ethanol. After cooling, the crystals are filtered under suction and recrystallized from methanol/isopropanol. There is obtained 5-(2-methyl-4-thiazolyl)-3-nitropyrocatechol hydrobromide of m.p. 280°–282°.

EXAMPLE 22

A solution of 1.38 g of 2-bromo-3',4'-dihydroxy-5'-nitroacetophenone and 461 mg of thiosemicarbazide in 20 ml of n-butanol is heated to boiling under reflux for 60 minutes. After cooling to room temperature the crystals are filtered under suction and recrystallized from n-butanol. There is obtained 5-(2-amino-6H-1,3,4-thiadiazin-5-yl)-3-nitropyrocatechol hydrobromide of m.p. 265°–267°.

EXAMPLE 23

A solution of 1.38 g of 2-bromo-3',4'-dihydroxy-5'-nitroacetophenone and 505.7 mg of 2-amino-1,3,4-thiadiazole in 25 ml of n-butanol is heated to boiling under reflux for 7 hours. The reaction mixture is then cooled to room temperature and the separated crystals are filtered under suction. There is obtained 5-(imidazo-[2,1-b]-1,3,4-thiadiazol-6-yl)-3-nitropyrocatechol of m.p. 278°–280° (from methanol).

EXAMPLE 24

A mixture of 2.78 g of 2-bromo-3',4'-dihydroxy-5'-nitroacetophenone, 1.01 g of 2-aminothiazole and 40 ml of ethanol is heated to boiling under reflux for 23 hours. The reaction mixture is then cooled to room temperature and the crystals are removed by filtration under suction. There is obtained 5-(imidazo[2,1-b]thiazol-6-yl)-3-nitropyrocatechol hydrobromide of m.p. 286°–288° (from methanol).

EXAMPLE 25

A mixture of 1.95 g of 2-bromo-3',4'-dihydroxy-5'-nitroacetophenone, 1.06 g of 2-aminobenzothiazole and 50 ml of ethanol is heated to boiling under reflux for 17 hours. The reaction mixture is then cooled to room temperature, whereupon the crystals are removed by filtration under suction. There is obtained 5-(imidazo[2,1-b]benzothiazol-2-yl)-3-nitropyrocatechol of m.p. 303°–305° (from N,N-dimethylformamide/methanol).

EXAMPLE 26

A mixture of 2.78 g of 2-bromo-3',4'-dihydroxy-5'-nitroacetophenone, 1.51 g of 2-aminothiophenol and 50 ml of ethanol is heated to boiling under reflux for 1 hour. The reaction mixture is then cooled to room temperature, whereupon the crystals are removed by filtration under suction. There is obtained 5-(2H-1,4-benzothiazin-3-yl)-3-nitropyrocatechol of m.p. 302°–304° (from N,N-dimethylformamide/methanol).

EXAMPLE 27

A mixture of 987.5 mg of 2-bromo-3',4'-dihydroxy-5'-nitroacetophenone and 1.01 g of 2-aminopyridine is melted at 110°. After 30 minutes the melt is treated with 15 ml of ethanol and heated to boiling under reflux for 3 hours. The reaction mixture is then cooled to room temperature and the crystals are removed by filtration under suction. There is obtained 5-(imidazo[1,2-a]-pyridin-3-yl)-3-nitropyrocatechol of m.p. 250°-252° (from N,N-dimethylformamide/methanol).

EXAMPLE 28 a) 8.9 g of 1,1'-carbonyldiimidazole are added to a solution of 10.7 g of 4-hydroxy-3-methoxy-5-nitrobenzoic acid in 500 ml of dry tetrahydrofuran and the reaction mixture is subsequently heated to 65°-70° for 5 hours. It is then cooled to room temperature and a solution of 21.6 g of 6-aminohexyl-t-butylcarbamate in 50 ml of dry tetrahydrofuran is added dropwise thereto within 15 minutes. The reaction mixture is then heated to 65°-70° for 18 hours, evaporated, the residue is suspended in ethyl acetate, suction filtered and the suction filtered material is chromatographed on silica gel with acetone-methylene chloride (3:1). There is obtained [6-(4-hydroxy-5-nitro-m-anisamido)hexyl]-t-butylcarbamate of m.p. 145°-147° (from isopropanol).

b) 5.8 ml of hydrobromic acid in glacial acetic acid (~33 percent) are added at room temperature to a solution of 4.1 g of [6-(4-hydroxy-5-nitro-m-anisamido)-hexyl]-t-butylcarbamate in 80 ml of glacial acetic acid. The mixture is stirred for 2 hours, the separated crystals are removed by filtration under suction and washed with ether. There is obtained N-(6-aminohexyl)-4-hydroxy-5-nitro-m-anisamide hydrobromide of m.p. 207°-209° (from isopropanol).

c) 1.25 g of boron tribromide are added −20° to a suspension of 392.3 mg of N-(6-aminohexyl)-4-hydroxy-5-nitroanisamide hydrobromide in 25 ml of dry methylene chloride. After the addition the mixture is stirred at −20° for 1 hour and subsequently at room temperature for 17 hours. The reaction mixture is then evaporated, the residue is treated with 10 ml of water and stirred at room temperature for 1 hour. After evaporating the water the residue is chromatographed on Sephadex LH 20 with toluene/ethanol (1:1). There is obtained N-6-aminohexyl-3,4-dihydroxy-5-nitrobenzamide hydrobromide of m.p. 205°-207° (from ethanol).

EXAMPLE 29 aa) A solution of 4.93 g of 5-nitrovanillin and 2.7 g of 1,2-phenylenediamine in 45 ml of methanol and 15 ml of nitrobenzene is heated to boiling under reflux. After 15 minutes crystals begin to separate from the red solution. After 18 hours the reaction mixture is cooled to room temperature and diluted with 60 ml of methanol. The crystals are filtered under suction and washed with methanol. There is obtained 4-(2-benzimidazolyl)-2-methoxy-6-nitrophenol of m.p. 198°-200° (from N,N-dimethylformamide/methanol).

In an analogous manner:

ab) From 5-nitrovanillin and 4,5-dichloro-1,2-phenylenediamine there is obtained 4-(5,6-dichloro-2-benzimidazolyl)-2-methoxy-6-nitrophenol of m.p. 258°-260° (from N,N-dimethylformamide/ether).

b) A suspension of 860.1 mg of 4-(2-benzimidazolyl)-2-methoxy-6-nitrophenol in 10 ml of glacial acetic acid and 10 ml of 48 percent hydrobromic acid is heated to boiling under reflux for 72 hours. The mixture is then evaporated and the residue is treated four times with 50 ml of toluene each time, which is again distilled each time. There is obtained 5-(2-benzimidazolyl)-3-nitropyrocatechol of m.p. >300° (from acetone/water).

In an analogous manner:

c) From 4-(5,6-dichloro-2-benzimidazolyl)-2-methoxy-6-nitrophenol there is obtained 5-(5,6-dichloro-2-benzimidazolyl)-3-nitropyrocatechol of m.p. 282°-284° (from acetone/water).

EXAMPLE 30

A suspension of 29.0 g of 2-bromo-4'-hydroxy-3'-methoxy-5'-nitroacetophenone in 700 ml of dry methylene chloride is treated at −20° within 30 minutes with a solution of 125.3 g of boron tribromide in 300 ml of dry methylene chloride. After the addition the mixture is stirred at −20° for a further 1 hour and at room temperature for 16 hours, then evaporated, the residue is treated cautiously with water while cooling with ice and stirred at 50° for 30 minutes. After cooling the mixture is extracted with ether, the ethereal phase is washed with water, dried over sodium sulfate, filtered and evaporated. There is obtained 2-bromo-3',4'-dihydroxy-5'-nitroacetophenone of m.p. 138°-140° (from methylene chloride).

EXAMPLE 31 a) A solution of 3.6 g of ethyl 3,4-dihydroxy-5-nitrophenylglyoxylate in 30 ml of acetic anhydride is heated at 110° for 30 minutes in the presence of a catalytic amount of conc. sulfuric acid, cooled to room temperature, the reaction mixture is poured into 150 ml of water and stirred for 60 minutes. The mixture is extracted with ether, washed with saturated sodium chloride solution, the combined organic extracts are dried sodium sulfate, filtered and evaporated. There is obtained ethyl 3,4-diacetoxy-5-nitrophenylglyoxylate of m.p. 87°-89° (from ether/petroleum ether).

In an analogous manner:

b) From 3-(3,4-dihydroxy-5-nitrophenyl)-2H-1,4-benzoxazin-2-one there is obtained 3-(3,4-diacetoxy-5-nitrophenyl)-2H-1,4-benzoxazin-2-one of m.p. 186°-188° (from methylene chloride/methanol).

c) from 3-(3,4-dihydroxy-5-nitrophenyl)-2(1H)-quinoxalinone there is obtained 3-(3,4-diacetoxy-5-nitrophenyl)-2(1H)-quinoxalinone of m.p. 241°-243° (from methylene chloride/methanol), d) from 3,4-dihydroxy-5-nitrobenzophenone there is obtained 3,4-diacetoxy-5-nitrobenzophenone of m.p. 141°-143° (from methylene chloride/ether), e) from 2'-fluoro-3,4-dihydroxy-5-nitrobenzophenone there is obtained 3,4-diacetoxy-2'-fluoro-5-nitrobenzophenone of m.p. 122°-124° (from ether) and f) from 3,4-dihydroxy-5-nitrophenyl 4-pyridyl ketone there is obtained 3,4-diacetoxy-5-nitrophenyl 4-pyridyl ketone of m.p. 148°-150° (from methylene chloride/ether).

EXAMPLE 32 a) A solution of 2.0 g of 3,5-dinitropyrocatechol in 25 ml of propionic anhydride is heated at 110° for 18 hours in the presence of a catalytic amount of conc. sulfuric acid, the excess anhydride is distilled off at 70° in a high vacuum (1.33 Pa), the residue is dissolved in methylene chloride, washed with water, dried over sodium sulfate, filtered and evaporated. There is obtained 1,2-dipropionyloxy-3,5-dinitrobenzene of m.p. 74°-76° (from methylene chloride/petroleum ether).

In an analogous manner:

b) From 3-(3,4-dihydroxy-5-nitrophenyl)-6-methyl-2H-1,4-benzoxazin-2-one there is obtained 3-(3,4-dipropionyloxy-5-nitrophenyl)-6-methyl-2H-1,4-benzoxazin-2-one of m.p. 158°–160° (from methylene chloride), c) from 6-chloro-3-(3,4-dihydroxy-5-nitrophenyl)-2H-1,4-benzoxazin-2-one there is obtained 5-(6-chloro-2-oxo-2H-1,4-benzoxazin-3-yl)-3-nitro-o-phenylenedipropionate of m.p. 148°–150° 1 (from methylene chloride/ether), d) from 3-(3,4-dihydroxy-5-nitrophenyl)-7-nitro-2H-1,4-benzoxazin-2-one there is obtained 3-nitro-5-(7-nitro-2-oxo-2H-1,4-benzoxazin-3-yl)-o-phenylenedipropionate of m.p. 177°–179° (from methanol), e) from 3-(3,4-dihydroxy-5-nitrophenyl)-2-oxo-2H-1,4-benzoxazine-6-carboxylic acid there is obtained 3-[3,4-benzoxazine-6-carboxylic acid there is obtained 3-[3,4-bis(propionyloxy)-5-nitrophenyl]-2-oxo-2H-1,4-benzoxazine-6-carboxylic acid of m.p. 192°–194° (from methylene chloride), f) from 3-nitro-5-(2-quinoxalinyl)pyrocatechol there is obtained 3-nitro-5-(2-quinoxalinyl)-o-phenylenedipropionate of m.p. 152°–154° (from methylene chloride/ether, g) from 5-(2-benzimidazolyl)-3-nitropyrocatechol there is obtained 5-(2-benzimidazolyl)-3-nitro-o-phenylenedipropionate of m.p. 179°–181° (from ether), h) from 6,7-dichloro-3-(3,4-dihydroxy-5-nitrophenyl)-2(1H)-quinoxalinone there is obtained 5-(6,7-dichloro-3,4-dihydro-3-oxo-2-quinoxalinyl)-3-nitro-o-phenylenedipropionate of m.p. 260°–262° (from methylene chloride), i) from 5-bromo-2-(3,4-dihydroxy-5-nitrobenzoyl)-3-methylindole there is obtained 5-bromo-2-(3,4-dipropionyloxy-5nitrobenzoyl)-3-methylindole of m.p. 196°–198° (from ether) and j) from 6-(3,4-dihydroxy-5-nitrophenyl)-3-mercapto-1,2,4-triazin-5(4H)-one there is obtained 3-nitro-5-(2,3,4,5-tetrahydro-5-oxo-3-thioxo-as-triazin-6-yl)-o-phenylenedipropionate of m.p. 237°–239° (from ether).

EXAMPLE 33 a) A solution of 1.09 g of ethyl 3,4-dihydroxy-5-nitrophenylglyoxylate in 6 ml of isobutyric anhydride is heated at 110° for 17 hours in the presence of a catalytic amount of conc. sulfuric acid. The reaction mixture is then treated ten times with 10 ml of toluene each time, whereby it is evaporated each time at 80° and 18.7 mbar. The oily residue is distilled in a bulb-tube at 175°–180° and 8.0 Pa. There is obtained ethyl 3,4-diisobutyryloxy-5-nitrophenylglyoxylate.

In an analogous manner:

b) From 3,5-dinitropyrocatechol there is obtained 1,2-diisobutyryloxy-3,5-dinitrobenzene of m.p. 78°–80° (from ether), c) from 3-(3,4-dihydroxy-5-nitrophenyl)-6-methyl-2H-1,4-benzoxazin-2-one there is obtained 3-(3,4-diisobutyryl-oxy-5-nitrophenyl)-6-methyl-2H-1,4-benzoxazin-2-one of m.p. 142°–144° (from ether), d) from 2-(3,4-dihydroxy-5-nitrophenyl)quinoxaline there is obtained 2-(3,4-diisobutyryloxy-5-nitrophenyl)-quinoxaline of m.p. 155°–157° (from ether), e) from 1-methyl-3-(3,4-dihydroxy-5-nitrophenyl)-2(1H)-quinoxalinone there is obtained 1-methyl-3-(3,4-diisobutyryloxy-5-nitrophenyl)-2(1H)-quinoxalinone of m.p. 138°–140° (from ether), f) from 5-(imidazo[2,1-b]-1,3,4-thiadiazol-6-yl)-3-nitropyrocatechol there is obtained 5-(imidazo[2,1-b]-1,3,4-thiadiazol-6-yl)-3-nitro-o-phenylene diisobutyrate of m.p. 169°–171° (from methylene chloride), g) from 2-bromo-3',4'-dihydroxy-5'-nitroacetophenone there is obtained 5-(bromoacetyl)-3-nitro-o-phenylene diisobutyrate of m.p. 56°–58° (from methylene chloride/hexane), h) from 5-(2-amino-4-thiazolyl)-3-nitropyrocatechol hydrobromide there is obtained 3-nitro-5-(2-isobutyramido-4-thiazolyl)-o-phenylene diisobutyrate of m.p. 157°–159° (from methylene chloride/ether), i) from 5-(2-amino-6H-1,3,4-thiadiazin-5-yl)-3-nitropyrocatechol hydrobromide there is obtained 3-nitro-5-(2-isobutyramido-4-isobutyryl-1,3,4-thiadiazin-5-yl)-o-phenylene diisobutyrate of m.p. 177°–179° (from ether), j) from 3-(3,4-dihydroxy-5-nitrophenyl)-6-propyl-2H-1,4-benzoxazin-2-one there is obtained 3-nitro-5-(2-oxo-6-propyl-2H-1,4-benzoxazin-3-yl)-o-phenylene diisobutyrate of m.p. 131°–133° (from methanol), k) from 5-(imidazo[1,2-a]pyridin-3-yl)-3-nitropyrocatechol there is obtained 5-(imidazo[1,2-a]pyridin-3-yl)-3-nitro-o-phenylene diisobutyrate of m.p. 137°–139° (from ether), l) from 5-(imidazo[2,1-b]benzothiazol-2-yl)-3-nitropyrocatechol there is obtained 5-(imidazo[2,1-b]benzothiazol-2-yl)-3-nitro-o-phenylene diisobutyrate of m.p. 197°–199° (from methylene chloride/ether and m) from 3,4-dihydroxy-5-nitrophenyl 2-pyridyl ketone hydrobromide there is obtained 3-nitro-5-(2-pyridylcarbonyl)-o-phenylene diisobutyrate of m.p. 83°–85° (from ether/hexane).

EXAMPLE 34 a) A solution of 613.0 mg of ethyl 3,4-dihydroxy-5-nitrophenylglyoxylate in 4 ml of pivaloyl anhydride is heated to 100° for 17 hours in the presence of a catalytic amount of conc. sulfuric acid, the cooled solution is diluted with ether, washed with saturated sodium solution, dried over sodium sulfate, filtered and evaporated. The residue is treated ten times with 10 ml of toluene, whereby it is evaporated again each time. After bulb-tube distillation (air-bath) at 175°–180° and 4.0 Pa there is obtained ethyl 3,4-dipivaloxyloxy-5-nitrophenylglyoxylate.

In an analogous manner:

b) From 3-(3,4-dihydroxy-5-nitrophenyl)-6-methyl-2H-1,4-benzoxazin-2-one there is obtained 3-(3,4-dipivaloyloxy-5-nitrophenyl)-6-methyl-2H-benzoxazin-2-one of m.p. 180°–192° (from ether), c) from 3,4-dihydroxy-5-nitrobenzophenone there is obtained 3,4-dipivaloyloxy-5-nitrobenzophenone of m.p. 101°–103° (from t-butyl methyl ether) and d) from 2'-fluoro-3,4-dihydroxy-5-nitrobenzophenone there is obtained 3,4-dipivaloyloxy-2'-fluorobenzophenone of m.p. 74°–76° (from low-boiling petroleum ether).

EXAMPLE 35

A solution of 1.7 g of 3-(3,4-dihydroxy-5-nitrophenyl)-2(1H)-quinoxalinone in 17 ml of oenanthic anhydride is heated to 110° for 17 hours in the presence of a catalytic amount of conc. sulfuric acid, the excess anhydride is then distilled in a high vacuum, the residue is dissolved in methylene chloride, the organic solution is washed with water, dried over sodium sulfate, filtered and evaporated. There is obtained 5-(1,2-dihydro-2-oxo-3-quinoxalinyl)-3-nitro-o-phenylene diheptanoate of m.p. 186°–188° (from methylene chloride/ether).

EXAMPLE 36 a) 1.26 g of sodium acetate are added to a solution of 1.35 g of 2-bromo-3',4'-dihydroxy-5'-nitroacetophenone in 25 ml of alcohol and heated to boiling under reflux. After 6 hours, the reaction mixture is filtered from separated sodium bromide and evaporated. The residue is dissolved in ethyl acetate. The solution is washed with saturated sodium chloride solution, dried over sodium sulfate, filtered and evaporated at 50°. There is obtained (3,4-dihydroxy-5-nitrobenzoyl)methyl acetate of m.p. 166°–168° (from ethyl acetate/ether).

In an analogous manner:

b) from 2-bromo-3',4'-dihydroxy-5'-nitroacetophenone and sodium isobutyrate there is obtained (3,4-dihydroxy-5-nitrobenzoyl)methyl isobutyrate of m.p. 120°–122° (from ethyl acetate/ether) and c) from 2-bromo-3',4'-dihydroxy-5'-nitroacetophenone and sodium 3,4-dihydroxy-5-nitrophenylglyoxylate there is obtained 3,4-dihydroxy-5-nitrophenacyl (3,4-dihydroxy-5-nitrobenzoyl)formate of m.p. 224°–226° (from methanol/ethyl acetate).

EXAMPLE 37

A suspension of 2.91 g of 2-bromo-3',4'-dihydroxy-5'-nitroacetophenone is treated with 1.31 g of thionicotinamide in 50 ml of alcohol and heated to boiling under reflux for 2 hours. After cooling to room temperature the crystals are filtered under suction and recrystallized from N,N-dimethylformamide/alcohol. There is obtained 3-nitro-5-[2-(3-pyridyl)-4-thiazolyl]pyrocatechol of m.p. 279°–281°.

EXAMPLE 38

A solution of 552 g of 2-bromo-3',4'-dihydroxy-5'-nitroacetophenone and 2.7 g of 2-aminoacetophenone in 100 ml of dry N,N-dimethylformamide is stirred at 90° for 24 hours. The reaction mixture is evaporated, the residue is dissolved in ethyl acetate, washed with water, dried over sodium sulfate, filtered and evaporated. There is obtained 2-(3,4-dihydroxy-5-nitrobenzoyl)-3-methylindole of m.p. 212°–214° (from n-butanol).

EXAMPLE 39

A suspension of 7.32 g of 2-bromo-3',4'-dihydroxy-5'-nitroacetophenone is treated with 4.06 g of 1-(3-pyridinyl)-2-thiourea in 100 ml of n-butanol and heated to boiling under reflux for 3 hours. After cooling to room temperature the crystals are filtered under suction and recrystallized from n-butanol. There is obtained 3-nitro-5-[2-(3-pyridylamino)-4-thiazolyl]pyrocatechol hydrobromide of m.p. >300°.

EXAMPLE 40

A suspension of 6.35 g of 2-bromo-3',4'-dihydroxy-5'-nitroacetophenone is treated with 4.68 g of 1-(3-quinolinyl)-2-thiourea in 150 ml of n-butanol and heated to boiling under reflux for 3 hours. After cooling to room temperature the crystals are filtered under suction and recrystallized from n-butanol. There is obtained 3-nitro-5-[2-(3-quinolinylamino)-4-thiazolyl]pyrocatechol hydrobromide of m.p. >300°.

EXAMPLE 41

A suspension of 8.28 g of 2-bromo-3',4'-dihydroxy-5'-nitroacetophenone is treated with 6.37 g of rac-1-(2-exo-bornyl)-2-thiourea in 100 ml of n-butanol and heated to boiling under reflux for 3 hours. After cooling to room temperature the crystals are filtered under suction and recrystallized from n-butanol. There is obtained rac-3-nitro-5-[2-(2-exo-bornylamino)-4-thiazolyl]-pyrocatechol hydrobromide of m.p. 262°–264°.

EXAMPLE 42

0.875 ml of pyrrolidine in 35 ml of tetrahydrofuran is treated at 5° with 0.605 ml of acetic acid and subsequently with 1.73 g of 3,4-dihydroxy-5-nitrobenzaldehyde and 2.87 g of 6-oxo-4'-(trifluoromethyl)-heptananilide and stirred at 23° under argon for 56 hours. The residue obtained after evaporating the reaction mixture is partitioned between ethyl acetate and 1N sodium hydroxide solution. The combined sodium hydroxide extracts are made acid with conc. hydrochloric acid, extracted with ethyl acetate, the combined ethyl acetate extracts are washed with saturated sodium chloride solution, dried over sodium sulfate, evaporated and the residue is chromatographed on 120 g of silica gel with methylene chloride/methanol (91:9). After recrystallization from ethyl acetate/petroleum ether there is obtained (E)-8-(3,4-dihydroxy-5-nitrophenyl)-6-oxo-4'-(trifluoromethyl)-7-octenanilide of m.p. 194°–197°.

EXAMPLE 43 a) 26.0 g of 2-chloro-3-hydroxy-p-anisaldehyde are dissolved in 400 ml of acetic anhydride and 5 ml of pyridine. The solution is stirred at 80° for 8 hours, subsequently evaporated, the residue is partitioned between ice-water and methylene chloride, the organic phase is dried over sodium sulfate, evaporated and the residue is recrystallized from methylene chloride/petroleum ether. There is obtained 2-chloro-3-formyl-6-methoxyphenyl acetate of m.p. 48°–50°.

b) 38 g of 2-chloro-3-formyl-6-methoxyphenyl acetate are introduced portionwise at −5° to −10° within 15 minutes into 150 ml of 98 percent nitric acid. After stirring at −5° for 30 minutes the reaction mixture is poured into 1.5 l of ice-water and extracted three times with 500 ml of methylene chloride. The combined organic phases are washed with ice-water, dried over sodium sulfate and evaporated. The residue is crystallized from ether. There is obtained 2-chloro-3-formyl-6-methoxy-5-nitrophenyl acetate of m.p. 84°–85°.

c) 35.8 g of 2-chloro-3-formyl-6-methoxy-5-nitrophenyl acetate are dissolved in 300 ml of methanol. After adding 145 ml of 1N sodium hydroxide solution the mixture is stirred at 23° for 1 hour. After evaporation of the methanol, the residue is diluted with ice-water, made acid with 2N hydrochloric acid and extracted twice with 400 ml of ethyl acetate each time. The organic phases are washed with saturated sodium chloride solution, dried over sodium sulfate and evaporated. The residue is recrystallized from methylene chloride/petroleum ether. There is obtained 2-chloro-3-hydroxy-5-nitro-p-anisaldehyde of m.p. 130°.

d) 1.3 g of 2-chloro-3-hydroxy-5-nitro-p-anisaldehyde are dissolved in 80 ml of methylene chloride, treated with 0.82 ml of boron tribromide, stirred at 23° for 18 hours, the reaction mixture is treated with 5 ml of methanol while cooling with ice, evaporated, the residue is dried in a high vacuum, digested in water, filtered and recrystallized from acetonitrile. There is obtained 2-chloro-3,4-dihydroxy-5-nitrobenzaldehyde of m.p. 193°–195°.

EXAMPLE 44 a) A mixture of 30 g of 2-chloro-3-hydroxy-p-anisaldehyde and 230 ml of ethanol is stirred at 70° for 4 hours in the presence of 12.3 g of hydroxylamine hydrochloride, the reaction mixture is subsequently evaporated, the residue is dried in a high vacuum and recrystallized from methanol/water. There is obtained 2-chloro-3-hydroxy-p-anisaldehyde oxime of m.p. 174°–176°.

b) 21 g of 2-chloro-3-hydroxy-p-anisaldehyde oxime are heated under reflux for 20 hours together with 400 ml of acetic anhydride. Thereupon, the reaction mixture is evaporated, the residue is treated with 300 ml of ice-water, stirred for 1 hour, decanted, the thus-cooled residue is partitioned between methylene chloride and water, the organic phase is dried over sodium sulfate, evaporated, the residue is dried in a high vacuum, chromatographed on 200 g of silica gel with methylene chloride and recrystallized from methylene chloride/petroleum ether. There is obtained 2-chloro-3-cyano-6-methoxyphenyl acetate of m.p. 97°–99°.

c) In analogy to Examples 43b and 43c, from 2-chloro-3-cyano-6-methoxyphenyl acetate there is obtained 2-chloro-3-hydroxy-5-nitro-p-anisonitrile of m.p. 157°–159° (methylene chloride/hexane).

d) In analogy to Example 43d, from 2-chloro-3-hydroxy-5-nitro-p-anisonitrile there is obtained 2-chloro-3,4-dihydroxy-5-nitro-benzonitrile of m.p. 180° (acetonitrile).

EXAMPLE 45 a) 5.5 g of α-chloro-2-fluoro-3,4-dimethoxytoluene and 4.05 g of potassium acetate are stirred at 80° for 25 hours in 50 ml of dimethylformamide. The reaction mixture is subsequently poured into 150 ml of ice-water and extracted with ether. The ether phases are washed with sodium chloride solution, dried over sodium sulfate and evaporated, 2-fluoro-3,4-dimethoxybenzyl acetate is obtained as an oil.

b) 5.4 g of 2-fluoro-3,4-dimethoxybenzyl acetate are heated to 80° for 1.5 hours together with 50 ml of methanol and 50 ml of 1N sodium hydroxide solution. After evaporation of the methanol the residue is extracted with methylene chloride. The combined extracts are washed with water, dried over sodium sulfate and evaporated. The residue is chromatographed on 80 g of silica gel with methylene chloride/methanol (95:5). 2-fluoro-3,4-dimethoxybenzyl alcohol is obtained as an oil.

c) 3.0 g of 2-fluoro-3,4-dimethoxybenzyl alcohol and 5.0 g of manganese dioxide are heated under reflux for 1 hour together with 50 ml of benzene. The insoluble constituents are subsequently filtered while washing with methylene chloride. The filtrate is evaporated and the residue is recrystallized from methylene chloride/hexane. There is obtained 2-fluoro-3,4-dimethoxybenzaldehyde of m.p. 52°–54°.

d) 4.4 g of 2-fluoro-3,4-dimethoxybenzaldehyde and 1.83 g of hydroxylamine hydrochloride are heated under reflux for 5 hours together with 30 ml of ethanol. The reaction mixture is subsequently evaporated and the residue, dried in a high vacuum at 23°, is introduced into 40 ml of phosphorus oxychloride. After stirring at 23° for 2.5 hours the reaction mixture is evaporated, the residue is treated with ice-water, the precipitate which thereby forms is filtered off, washed with water, taken up in methylene chloride, the methylene chloride solution is dried over sodium sulfate and evaporated. By recrystallization of the residue from methylene chloride/hexane there is obtained 2-fluoro-3,4-dimethoxybenzonitrile of m.p. 64°–65°.

e) 2.0 g of 2-fluoro-3,4-dimethoxybenzonitrile are dissolved in 60 ml of methylene chloride, treated with 1.1 ml of boron tribromide, stirred at 23° for 1 hour, subsequently treated with an additional 1.0 ml of boron tribromide and stirred at 23° for an additional 80 minutes. Thereupon, the reaction mixture is poured into 100 ml of ice-cold saturated sodium hydrogen carbonate solution, whereupon the mixture is extracted twice with 300 ml of ether, the combined ether phases are washed twice with sodium chloride solution, dried over sodium sulfate, evaporated and the residue is chromatographed on 50 g of silica gel with methylene chloride and methylene chloride/methanol (97:3). There is obtained 2-fluoro-3-hydroxy-p-anisonitrile of m.p. 198°–200°.

f) 0.9 g of 2-fluoro-3-hydroxy-p-anisonitrile are dissolved in 10 ml of acetic anhydride and 0.5 ml of pyridine, whereupon the mixture is stirred at 120° for 2 hours. The reaction mixture is subsequently evaporated and the residue is partitioned between ice-water and methylene chloride. The organic phase is dried over sodium sulfate and evaporated, and the residue is recrystallized from methylene chloride/hexane. There is obtained 3-cyano-2-fluoro-6-methoxyphenyl acetate of m.p. 90°–91°.

g) 0.8 g of 3-cyano-2-fluoro-6-methoxyphenyl acetate are introduce din three portions at −15° into 5 ml of 96 percent nitric acid, whereupon the mixture is stirred at −10° for 1 hour. Thereupon, the reaction mixture is poured on to 50 g of ice. The mixture is extracted twice with 70 ml of ethyl acetate each time. The combined organic phases are washed with saturated sodium chloride solution, dried over sodium sulfate and evaporated. The thus-obtained residue is dissolved in 50 ml of 1N sodium carbonate solution and 50 ml of methanol, whereupon the solution is stirred at 23° for 1 hour and the methanol is distilled off. The residal aqueous phase is adjusted to pH 2 at 0° with conc. hydrochloric acid and extracted twice with 100 ml of ethyl acetate. The combined organic phases are washed with saturated sodium chloride solution, dried over sodium sulfate and evaporated, and the residue is chromatographed on 45 g of silica gel with methylene chloride/methanol (97:3). After recrystallization from ether/hexane there is obtained 2-fluoro-3-hydroxy-5-nitro-p-anisonitrile of m.p. 112°–113°.

h) 550 mg of 2-fluoro-3-hydroxy-5-nitro-p-anisonitrile are dissolved in 30 ml of methylene chloride, whereupon the solution is treated with 0.44 ml of boron tribromide. After stirring at 23° for 6 hours an additional 0.1 ml of boron tribromide are added thereto, whereupon the mixture is stirred at 23° for an additional 1.5 hours. Thereupon, 3 ml of ethanol are added thereto at −15°. The reaction mixture is evaporated and the residue is dried in a high vacuum at 23°. By recrystallization from ether/hexane there is obtained 2-fluoro-3,4-dihydroxy-5-nitrobenzonitrile of m.p. 154°.

EXAMPLE 46 a) 9.5 g of 3,4-dimethoxy-5-nitrobenzoic acid are suspended in 95 ml of thionyl chloride. The suspension is stirred at 80° for 1 hour. By two-fold evaporation with the addition of absolute toluene there are obtained 10 g of 3,4-dimethoxy-5-nitrobenzoyl chloride which is dissolved in 100 ml of tetrahydrofuran. This solution is added dropwise to 300 ml of 28 percent aqueous ammonia. The mixture is subsequently stirred at 40° for 2 hours and cooled to 5°. The crystalline precipitate is filtered off. There is obtained 3,4-dimethoxy-5-nitrobenzamide of m.p. 182°–185°.

b) 2.46 g of chlorine are introduced while cooling with ice into a mixture of 8.0 g of sodium hydroxide, 50 ml of water and 30 g of ice. Thereupon, 6.5 g of 3,4-dimethoxy-5-nitrobenzamide suspended in 5 ml of tetrahydrofuran are slowly added thereto. The reaction mixture is heated to 70° within 30 minutes, stirred at 70° for 1 hour, cooled to 5° and the separated crystals are filtered off. There is obtained 3,4-dimethoxy-5-nitroaniline of m.p. 129°–131°. By extraction of the filtrate with ethyl acetate, drying the extract over sodium sulfate, concentration and crystallization of the residue with the addition of ether there can be obtained an additional portion of 3,4-dimethoxy-5-nitroaniline.

c) 10 g of finely powdered 3,4-dimethoxy-5-nitroaniline are suspended in 15 ml of 12N hydrochloric acid and 40 ml of water, whereupon the suspension is stirring at 30° for 1 hour. Thereupon, 3.8 g of sodium nitrite dissolved in 20 ml of water are added dropwise thereto at −5° within 15 minutes. The solution is stirred at −5° for 30 minutes and the cold diazonium salt solution is added dropwise within 45 minutes to 100 ml of pyridine of 40°. The mixture is subsequently stirred at 70° for 1 hour. The reaction mixture is evaporated and the residue is taken up in 300 ml of ethyl acetate. It is extracted three times with 200 ml of 2N hydrochloric acid each time. The acidic-aqueous phase is adjusted to pH 9 with conc. ammonia and extracted with methylene chloride. The combined methylene chloride extracts are dried over sodium sulfate and evaporated, and the residue is chromatographed on 250 g of silica gel with ethyl acetate. After crystallization from methylene chloride/hexane there is obtained 2-(3,4-dimethoxy-5-nitrophenyl)-pyridine of m.p. 89°–90°.

d) 1.5 g of 2-(3,4-dimethoxy-5-nitrophenyl)pyridine are dissolved in 30 ml of 48 percent aqueous hydrobromic acid. The reaction mixture is stirred at 100° for 16 hours and at 23° for 18 hours. The precipitate which thereby forms is filtered and recrystallized from methanol/ether. There is obtained 3-nitro-5-(2-pyridyl)-pyrocatechol hydrobromide of m.p. 230°–240°.

EXAMPLE 47 a) 2.76 ml of 2-bromopyridine dissolved in 30 ml of absolute tetrahydrofuran are treated −60° within 30 minutes with 19.2 ml of 1.6M n-butyl lithium solution (in hexane), whereupon the mixture is stirred at −60° for 30 minutes. 6.0 g of 3,4-dimethoxy-5-nitrobenzaldehyde dissolved in 50 ml of tetrahydrofuran are then added dropwise thereto at −40° within 30 minutes. The reaction mixture is warmed to 0° within 2 hours, poured into ice-water and extracted with ethyl acetate. The combined extracts are dried over sodium sulfate and evaporated, and the residue is chromatographed on 200 g of silica gel with ethyl acetate. There is obtained α-(3,4-dimethoxy-5-nitrophenyl)-2-pyridinemethanol as a brown oil.

b) 7 g of manganese dioxide and added portionwise to 4.0 g of α-(3,4-dimethoxy-5-nitrophenyl)-2-pyridinemethanol dissolved in 100 ml of acetone while constantly heating under reflux over a period of 2.5 hours. Thereupon, the mixture is heated under reflux for an additional 2 hours. The manganese salts are subsequently filtered and the residue obtained after evaporation is recrystallized from ether/hexane. There is obtained 3,4-dimethoxy-5-nitrophenyl 2-pyridyl ketone of m.p. 113°.

c) 1.5 g of 3,4-dimethoxy-5-nitrophenyl-2-pyridyl ketone dissolved in 30 ml of 48 percent hydrobromic acid are stirred at 100° for 18 hours. Thereupon, the reaction mixture is evaporated and the residue is recrystallized from acetonitrile/methanol. There is obtained 3,4-dihydroxy-5-nitrophenyl 2-pyridyl ketone hydrobromide of m.p. 213°.

EXAMPLE 48 a) 11.3 g of tin dichloride dihydrate are added to 2.25 g of 3',4'-dimethoxy-5'-nitroacetophenone dissolved in 50 ml of ethanol, whereupon the mixture is stirred at 74° for 30 minutes. Thereupon, the reaction mixture is poured on to 100 g of ice, neutralized with about 300 ml of saturated sodium hydrogen carbonate solution and treated with 150 ml of methylene chloride. The mixture is filtered and the methylene chloride phase is separated. This is dried over sodium sulfate and evaporated, and the residue is recrystallized from ether/petroleum ether. There is obtained 5'-amino-3',4'-dimethoxyacetophenone of m.p. 63°–65°.

b) A solution of 5.2 g of sodium nitrile in 20 ml of water is added dropwise at 0° within 20 minutes to 14.0 g of 5'-amino-3',4'-dimethoxyacetophenone dissolved in 155 ml of 1N hydrochloric acid. After stirring at −2° for 30 minutes the cold diazonium salt solution is added dropwise within 30 minutes at 5°–10° to a solution of 8.7 g of copper(I) cyanide and 5.45 g of potassium cyanide in 60 ml of water. After completion of the addition 200 ml of methylene chloride are added, and the reaction mixture is stirred at 23° for 3 hours and then filtered. The organic phase is separated, washed with water, dried over sodium sulfate and evaporated. The residue is recrystallized from methylene chloride/petroleum ether. There is obtained 5'-cyano-3',4'-dimethoxyacetophenone of m.p. 125°–126°.

c) 3.75 g of aluminum powder and 28.5 g of iodine are heated under reflux for 2 hours in 160 ml of absolute benzene. 3.0 g of 5'-cyano-3',4'-dimethoxyacetophenone and 0.5 g of tetra-n-butylannomium iodide are then added at 20°, whereupon the mixture is heated under reflux for 1 hour. Thereupon, the mixture is treated at 20° with 50 g of ice and filtered. The residue is washed with ethyl acetate. The phases are separated and the aqueous phase is extracted twice with ethyl acetate. The combined organic phases are washed with 20 percent sodium thiosulfate solution, dried over sodium sulfate and evaporated. The thus-obtained residue is dissolved in 20 ml of acetic anhydride and 0.5 ml of pyridine and stirred at 120° for 6 hours. The mixture is subsequently evaporated and the residue is partitioned between methylene chloride and ice-water. The methylene chloride phase is dried over sodium sulfate and evaporated, and the residue is chromatographed on 100 g of silica gel with methylene chloride. After recrystallization from ether there is obtained 5'-cyano-3',4'-diacetoxyacetophenone of m.p. 76°–79°.

EXAMPLE 49

0.33 g of 5'-cyano-3',4'-diacetoxyacetophenone dissolved in 3.3 ml of methanol is treated with 2.7 ml of 1.0N sodium hydroxide solution and the reaction mixture is stirred at 23° for 45 minutes. The mixture is subsequently acidified with 2N hydrochloric acid, diluted with 5 ml of saturated sodium chloride solution and extracted twice with 30 ml of ethyl acetate each time.

The combined ethyl acetate phases are dried over sodium sulfate and evaporated. The residue is recrystallized from toluene/acetonitrile. There is obtained 5'-cyano-3',4'-dihydroxyacetophenone as brownish crystals which decompose which decompose above 215°.

EXAMPLE 50 a) 3.48 g of phenyltrimethylammonium bromide dibromide dissolved in 30 ml of tetrahydrofuran are added dropwise at room temperature within 45 minutes to 1.9 g of 5'-cyano-3',4'-dimethoxyacetophenone dissolved in 30 ml of tetrahydrofuran, whereupon the mixture is stirred for 30 minutes. Thereupon, the reaction mixture is poured into 120 ml of ice-water and extracted three times with 70 ml of methylene chloride. The combined methylene chloride phases are washed with 2N sulfuric acid, dried over sodium sulfate and evaporated. The residue is chromatographed on 20 g of silica gel with methylene chloride. After recrystallization from methylene chloride/hexane there is obtained 5-(bromoacetyl)-2,3-dimethoxybenzonitrile of m.p. 138°-141°.

b) 1.45 g of 5-(bromoacetyl)-2,3-diethoxybenzonitrile and 1.12 g of selenium dioxide are stirred at 120° for 18 hours in 10 ml of n-hexanol. After cooling to room temperature the mixture is diluted with 20 ml of methylene chloride and filtered. The filtrate is washed with water, dried over sodium sulfate and evaporated. The residue is chromatographed on 70 g of silica gel with hexane/ether (2:1). there is obtained hexyl (3-cyano-4,5-dimethoxyphenyl)glyoxylate as an oil.

c) 4.8 ml of boron tribromide dissolved in 20 ml of methylene chloride are added dropwise while cooling with ice within 20 minutes to 4.0 g of hexyl (3-cyano-4,5-dimethoxyphenyl)glyoxylate dissolved in 100 ml of methylene chloride and the reaction mixture is stirred at room temperature for 18 hours. 40 ml of methanol are subsequently added dropwise thereto at −60°, the mixture is stirred at room temperature for 1 hour and evaporated. The residue is taken up in methanol. It is heated under reflux for 10 minutes, evaporated to dryness and dried in a high vacuum. The thus-obtained crude product is recrystallized from acetonitrile. There is obtained methyl (3-cyano-4,5-dihydroxyphenyl)glyoxylate of m.p. 252°.

EXAMPLE 51

1.075 g of methyl (3-cyano-4,5-dihydroxyphenyl)glyoxylate and 0.60 g of 2-amino-p-cresol are stirred at 120° for 70 minutes in 2 ml of dimethylformamide. The mixture is subsequently cooled to room temperature and diluted with 15 ml of water. The precipitate is filtered and dried in a water-jet vacuum at 80° for 6 hours. After recrystallization from acetonitrile there is obtained 2,3-dihydroxy-5-(6-methyl-2-oxo-2H-1,4-benzoxazin-3-yl)benzonitrile of m.p. 278°-280°.

EXAMPLE 52 a) A solution of 2.5 g of 3,4-dimethoxy-5-nitrobenzoyl chloride in 10 ml of absolute tetrahydrofuran is treated with 1.1 ml of ethyl isocyanoacetate and subsequently with a solution of 3.0 ml of triethylamine in 10 ml of tetrahydrofuran and stirred at room temperature for 48 hours. After distillation of the solvent, the residue is extracted with ethyl acetate/water. The crude product obtained after evaporation is chromatographed on a 20-fold amount of silica gel with ethyl acetate. After recrystallization from ethyl acetate/hexane there is obtained ethyl 5-(3,4-dimethoxy-5-nitrophenyl)-4-oxazolecarboxylate in the form of yellow crystals of m.p. 109°-110°.

b) 1.0 g of ethyl 5-(3,4-dimethoxy-5-nitrophenyl)-4-oxazolecarboxylate is treated with 10 ml of constant-boiling hydrobromic acid and stirred at 140° for 2 hours. After distillation of the excess hydrobromic acid, the yellow residue is recrystallized from ethanol/acetone. There is obtained 2-amino-3',4'-dihydroxy-5'-nitroacetophenone hydrobromide in the form of yellow crystals of m.p. >250° (dec.).

EXAMPLE 53 a) 10 g of ethyl (3,4-dimethoxy-5-nitrobenzoyl)acetate are suspended in 100 ml of ethanol, treated with 1.7 g of methylhydrazine and heated under reflux for 16 hours. After distillation of about 50 ml of ethanol, the mixture is cooled to 0° and the separated precipitate is filtered under suction. After recrystallization from ethanol there is obtained 3-(3,4-dimethoxy-5-nitrophenyl)-1-methylpyrazol-5-ol in the form of yellow crystals of m.p. 200°-202°.

b) 2.0 g of 3-(3,4-dimethoxy-5-nitrophenyl)-1-methylpyrazol-5-ol are suspended in 100 ml of methylene chloride. After cooling to −40° a solution of 4.9 ml of boron tribromide in 60 ml of methylene chloride is added dropwise thereto within 1 hour. The mixture is subsequently stirred at room temperature for 16 hours, cooled to −20° and treated within 30 minutes with 100 ml of ethanol. After stirring at room temperature for 1 hour, the solvent is removed by distillation in a water-jet vacuum at 40°. The residue is treated three times with a mixture of 100 ml of ethanol/toluene each time, with the solvent being distilled each time. The residue is recrystallized from ethanol. There is obtained 5-(5-hydroxy-1-methylpyrazol-3-yl)-3-nitropyrocatechol hydrobromide int he form of yellow crystals of m.p. >250°.

EXAMPLE 54 a) 16.8 g (0.7 g-atom) of magnesium are treated with 15 ml of ethanol and, after adding 2 ml of carbon tetrachloride, the reaction is initiated by heating. A solution of 130.3 g of tert.butyl ethyl malonate in 70 ml of ethanol and 600 ml of absolute ether is added dropwise thereto while stirring within about 30 minutes so that the reaction proceeds at the reflux temperature. The mixture is subsequently stirred at 50° for an additional 3 hours and the solvent is distilled at 40° in a water-jet vacuum. The residue is dissolved in 900 ml of tetrahydrofuran. To this solution is added dropwise while stirring at 50° a solution of 170 g of 3,4-dimethoxy-5-nitrobenzoyl chloride in 700 ml of absolute tetrahydrofuran and the mixture is stirred at the reflux temperature for 1 hour. The solvent is distilled at 40° in a water-jet vacuum. The residue is treated with 1 l of ether. 260 ml of 3N sulfuric acid are added thereto while cooling and stirring and the mixture is stirred for 30 minutes. The aqueous phase is extracted twice with 600 ml of ether each time. The organic phase is washed neutral with water, dried over sodium sulfate and evaporated. The brown oil obtained is filtered over 1 kg of silica gel with toluene. The resulting mixture, consisting of ethyl tert.butyl (3,4-dimethoxy-5-nitrobenzoyl)malonate and ethyl (3,4-dimethoxy-5-nitrobenzoyl)acetate, is dissolved in 600 ml of methylene chloride and treated while stirring within about 30 minutes with 193 ml of trifluoracetic acid. The mixture is subsequently stirred at 40° for 2 hours and then evaporated at 40° in a water-jet vacuum. The oil obtained is extracted with ether/water. The organic phase is dried over sodium sulfate and evaporated. After dissolution in diisopropyl ether/hexane and cooling the separated crystals are filtered under suction and recrystallized from diisopropyl ether. There is obtained ethyl (3,4-dimethoxy-5-nitrobenzoyl)acetate in the form of slightly yellowish crystals of m.p. 67°-68°.

b) 10.0 g of ethyl (3,4-dimethoxy-5-nitrobenzoyl)acetate are reacted with 4.0 g of phenylhydrazine in analogy to Example 53a. After recrystallization from methylene chloride/ethanol, there is obtained 3-(3,4-dimethoxy-5-nitrophenyl)-1-phenyl-2-pyrazolin-5-one in the form of yellow crystals of m.p. 190°-192°.

c) In analogy to Example 53b, with boron tribromide there is obtained therefrom 5-(5-hydroxy-1-phenyl-pyrazol-3-yl)-3-nitropyrocatechol hydrobromide in the form of yellow crystals of m.p. >220° (dec.).

EXAMPLE 55

20.1 g of diethyl (3,4-dimethoxy-5-nitrobenzoyl)malonate are dissolved in 200 ml of methylene chloride, whereupon the solution is cooled to −20° and at this temperature there is added dropwise while stirring within 15 minutes a solution of 68.1 g of boron tribromide in 120 ml of methylene chloride. The mixture is subsequently stirred at room temperature overnight. After cooling to −20°, the mixture is treated with 300 ml of ethanol and stirred at room temperature for 30 minutes. The solvent is distilled in a water-jet vacuum at 40°. The residue is treated with 300 ml of ice-water and methylene chloride. The organic phase is washed with water, dried over sodium sulfate and evaporated. The crude product obtained is chromatographed on a 10-fold amount of silica gel with toluene. After crystallization from methylene chloride/hexane there is obtained ethyl (3,4-dihydroxy-5-nitrobenzoyl)acetate in the form of yellow crystals of m.p. 136°-137°.

EXAMPLE 56

2.0 g of ethyl (3,4-dihydroxy-5-nitrobenzoyl)acetate are suspended in 50 ml of ethanol. After treatment with 0.4 g of hydrazine hydrate the mixture is held at the reflux temperature for 16 hours. After distillation of the solvent, the residue is held at the boiling temperature for 5 minutes with 50 ml of ethyl acetate. The separated precipitate is filtered under suction and the filtrate is concentrated to 10 ml. The crystals, which separate in the cold, are filtered under suction. There is obtained 5-(5-hydroxypyrazol-3-yl)-3-nitropyrocatechol in form of orange crystals of m.p. 228° (dec.).

EXAMPLE 57

7.3 g of 3,4-dihydroxy-5-nitrobenzoic acid are treated with 30 ml of acetic anhydride, whereupon the mixture is held at the reflux temperature for 8 hours. The reaction mixture is poured on to ice. The separated precipitate is filtered under suction, washed with water and taken up in methylene chloride. The organic phase is dried over sodium sulfate and evaporated. The residue obtained is recrystallized from methylene chloride/n-hexane in the cold. There is obtained 3,4-diacetoxy-5-nitrobenzoic acid in the form of colorless crystals of m.p. 126°-127°.

EXAMPLE 58 a) 9.7 g of 3,4-diacetoxy-5-nitrobenzoic acid are treated with 12.5 ml of thionyl chloride, whereupon the mixture is stirred at 100° for 1.5 hours. After distillation of the excess thionyl chloride, the 5-(chloro-carbonyl)-2-nitro-o-phenylene diacetate is distilled, b.p. 160° (26.7 Pa).

b) 3.2 g of 5-(chlorocarbonyl)-2-nitro-o-phenylene diacetate are dissolved in 50 ml of dimethylformamide. The ice-cold solution is treated while stirring with a solution of 2.2 ml of diethylamine in 20 ml of dimethylformamide. The mixture is subsequently stirred at room temperature for 1 hour, whereupon the solvent is distilled in a water-jet vacuum at 50°. The residue obtained is treated with water and methylene chloride. The organic phase is dried over sodium sulfate and evaporated. The yellow resin obtained is crystallized from methylene chloride/ether. There is obtained N,N-diethyl-3,4-dihydroxy-5-nitrobenzamide in the form of yellow crystals of m.p. 145°-146°.

EXAMPLE 59

3.2 g of 5-(chlorocarbonyl)-2-nitro-o-phenylenediacetate are dissolved in 50 ml of dimethylformamide, whereupon the solution is treated at 0°-5° while stirring and within 40 minutes with a solution of 3.02 ml of 2,2-diethylaminoethylamine in 20 ml dimethylformamide. The mixture is subsequently stirred at room temperature for 30 minutes. The solvent is distilled in a water-jet vacuum at 60°. The residue is extracted twice with 20 ml of ethanol each time, dissolved in hot ethanol and treated with an excess of ethanolic hydrochloric acid, whereupon the mixture is evaporated. After recrystallization from ethanol/ethyl acetate there is obtained N-[2-(diethylamino)ethyl]-3,4-dihydroxy-5-nitrobenzamide hydrochloride in the form of yellow crystals of m.p. 139° (dec.).

EXAMPLE 60 a) 10.0 g of 2,3-dimethoxy-5-nitrobenzaldehyde are treated with 50 ml of glacial acetic acid and 50 ml of constant-boiling hydrobromic acid and held at the reflux temperature for 7 hours. After treatment with ice the separated precipitate is filtered under suction, washed with water and taken up in ethyl acetate. The organic phase is dried over sodium sulfate and evaporated. The crude product obtained is filtered over silica gel with ethyl acetate. After crystallization from ethyl acetate/hexane there is obtained 2,3-dihydroxy-5-nitrobenzaldehyde in the form of brownish crystals of m.p. 226°-228°.

b) 4.5 g of 2,3-dihydroxy-5-nitrobenzaldehyde are suspended in 75 ml of water. After treatment with 4.2 g of hydroxylamine o-sulphonic acid, the mixture is stirred at 65° for 16 hours. After cooling the separated crystals are filtered under suction and washed with water. The filtrate is extracted with ethyl acetate. The crystals and the dried organic phase are combined, whereupon the mixture is evaporated and the residue is recrystallized from diisopropyl ether. There is obtained 2,3-dihydroxy-5-nitrobenzonitrile in the form of yellow crystals of m.p. 186°-188°.

EXAMPLE 61 a) 4.0 g of 3,4-dimethyoxy-5-nitro-benzonitrile are dissolved in 50 ml of dimethylformamide, whereupon the solution is treated with 1.66 g of ammonium chloride and 2.02 g of sodium azide and stirred at 125° for 31 hours. After in each case 8 and 15 hours the same amounts of ammonium chloride and sodium azide are added thereto. After cooling the mixture is poured on to ice. The separated precipitate is filtered under suction, washed with water and dried. There is obtained 2-methoxy-6-nitro-4-(1H-tetrazol-5-yl)phenol in the form of orange crystals of m.p. >240° (dec.).

b) 4.0 g of 2-methoxy-6-nitro-4-(1H-tetrazol-5-yl)phenol are treated with 40 ml of constant-boiling hydrobromic acid, whereupon the mixture is stirred at 140° for 8 hours under a nitrogen atmostphere. After cooling, the mixture is poured on to ice. The separated precipitate is filtered under suction and recrystallized from ether. There is obtained 3-nitro-5-(1H-tetrazol-5-yl)-pyrocatechol in the form of orange crystals of m.p. >240° (dec.).

EXAMPLE 62

A total of 7.2 g of 3,4-dihydroxy-5-nitro-benzonitrile are introduced portionwise into 130 ml of conc. sulfuric acid while stirring within 10 minutes, whereupon the mixture is stirred at 50° for 4 hours. The reaction mixture is poured into 800 ml of ice-water. The separated precipitate is filtered under suction, washed with water and taken up in ethyl acetate. The organic phase is dried over sodium sulfate and evaporated. After recrystallization from acetone/ethyl acetate there is obtained 3,4-dihydroxy-5-nitrobenzamide in the form of orange crystals of m.p. 235°–236°.

EXAMPLE 63 a) A solution of 11.25 g of 2-hydroxyacetophenone in 100 ml of absolute dimethylformamide is added dropwise under an argon atmosphere within 15 minutes to a suspension of 3.6 g of a 55 percent sodium hydride dispersion in 50 ml of absolute dimethyformamide and the mixture is stirred at room temperature for 1 hour. After cooling to 0°, a solution of 20.3 g of 3,4-dimethoxy-5-nitrobenzoyl chloride in 100 ml of absolute dimethylformamide is added dropwise thereto within 20 minutes and the mixture is stirred at room temperature overnight. The reaction mixture is poured into ice-water, whereupon the mixture is extracted twice with 250 ml of ethyl acetate each time. The organic phase is extracted twice with 100 ml of sodium chloride solution each time, dried over sodium sulfate and evaporated. The brown oil obtained is heated in 100 ml of toluene. The separated precipitate is filtered under suction and the filtrate is chromatographed on a 30-fold amount of silica gel with toluene/ethyl acetate (4:1). After recrystallization from ethyl acetate/hexane there is obtained o-acetylphenyl 3,4-dimethoxy-5-nitrobenzoate in the form of yellowish crystals of m.p. 108°–109°.

b) 10.0 g of o-acetylphenyl 3,4-dimethoxy-5-nitrobenzoate are dissolved in 50 ml of pyridine. After treatment with 8.12 g of powdered and dried potassium hydroxide, the mixture is stirred at 80° for 5 minutes. After cooling the mixture is poured on to ice. The aqueous solution is made acid by treatment with 3N hydrochloric acid. The separated precipitate is removed by filtration under suction. After recrystallization from ethyl acetate/hexane, there is obtained 1-(o-hydroxyphenyl)-3-(3,4-dimethoxy-5-nitrophenyl)-1,3-propanedione in the form of yellowish crystals of m.p. 188°–189°.

c) A solution of 1.82 g of boron tribromide in 20 ml of methylene chloride is added dropwise within about 20 minutes to a solution of 500 mg of 1-(o-hydroxyphenyl)-3-(3,4-dimethoxy-5-nitrophenyl)-1,3-propanedione in 50 ml of methylene chloride while stirring and under an argon atmosphere at −20°, whereupon the mixture is stirred at room temperature overnight. After cooling to −20° the mixture is treated dropwise with 25 ml of ethanol and evaporated at 40° in a water-jet vacuum. After recrystallization from ethanol, there is obtained 1-(3,4-dihydroxy-5-nitrophenyl)-3-(o-hydroxyphenyl)-1,3-propanedione in the form of yellow crystals of m.p. 251°–252°.

EXAMPLE 64 a) A solution of 2.0 g of o-acetylphenyl 3,4-dimethoxy-5-nitrobenzoate in 12.5 ml of glacial acetic acid is treated with 0.94 g of sodium acetate and held at the reflux temperature for 4 hours. After cooling the mixture is poured into ice-water. The separated crystals are filtered under suction. After recrystallization from ethyl acetate/hexane there is obtained 2-(3,4-dimethoxy-5-nitrophenyl)-4H-1-benzopyran-4-one in the form of colorless crystals of m.p. 216°–217°.

b) A solution of 10 ml of boron tribromide in 50 ml of methylene chloride are added dropwise within 30 minutes at −10° to a solution of 1.0 g of 2-(3,4-dimethoxy-5-nitrophenyl)-4H-1-benzopyran-4-one in 100 ml of methylene chloride under an argon atmosphere, whereupon the mixture is stirred at room temperature overnight. After cooling to −20°, 20 ml of ethanol are added dropwise thereto. The mixture is then evaporated in a waterjet vacuum. The yellow residue obtained is extracted with water/ethyl acetate. The organic phase is washed with water, dried over sodium sulfate and evaporated. After recrystallization from ethanol/ethyl acetate, there is obtained 2-(3,4-dihydroxy-5-nitrophenyl)-4H-1-benzopyran-4-one in the form of yellow crystals of m.p. >240° (dec.).

EXAMPLE 65 a) 92 ml of n-butyl lithium solution (1.6M in hexane) are added dropwise at −70° within 20 minutes to 33.0 g of 4-bromobenzotrifluoride (dissolved in 150 ml of tetrahydrofuran). After stirring at −70° for 45 minutes, 36 g of 3-methoxy-4-benzyloxybenzaldehyde (dissolved in 100 ml of tetrahydrofuran) are added dropwise thereto at between −70° and −60°. The reaction mixture is stirred at −70° for 2 hours and at 0° for 1 hour, poured into a mixture of ice and 100 ml of 2N sulfuric acid and extracted twice with 500 ml of ether. The combined ether phases are washed with saturated sodium chloride solution, dried over sodium sulfate and evaporated. There is obtained 4-(benzyloxy)-3-methoxy-4'-(trifluoromethyl)benzhydrol which can be used directly in the subsequent reaction step.

b) 52.6 g of 4-(benzyloxy)-3-methoxy-4'-(trifluoromethyl)benzhydrol (dissolved in 500 ml of methylene chloride) are treated within 10 minutes at 20° with 30.6 g of pyridinium chlorochromate and stirred at 20° for 2 hours. The precipitate formed is subsequently filtered and washed with methylene chloride. The filtrate is evaporated and the residue is chromatographed on 150 g of silica gel with methylene chloride. After recrystallization from methylene chloride/hexane, there is obtained 4-benzyloxy)-3-methoxy-4'-(trifluoromethyl)-benzophenone of melting point 101°.

c) 70 ml. of 33 percent hydrobromic acid in acetic acid are added within 15 minutes at 10° to 20 g of 4-(benzyloxy)-3-methoxy-4'-(trifluoromethyl)benzophenone (dissolved in 150 ml of methylene chloride). After stirring at 20° for 1.5 hours, the reaction mixture is poured into 600 ml. of ice-water; the methylene chloride phase is separated and the aqueous phase is extracted twice more with 100 ml. of methylene chloride. The combined methylene chloride phases are washed with 600 ml of water, dried over sodium sulfate and evaporated. The residue is chromatographed on 150 g of silica gel with methylene chloride. After recrystallization from methylene chloride/hexane, there is obtained 4-hydroxy-3-methoxy-4'-(trifluoromethyl)benzophenone of melting point 97°.

d) 3.2 ml of 65 percent nitric acid are added dropwise within 10 minutes at 20° to 12.8 g of 4-hydroxy-3-methoxy-4'-(trifluoromethyl)benzophenone (dissolved in 160 ml of acetic acid). After stirring for 1.5 hours, the reaction mixture is poured into 600 ml of ice-water, and the precipitate formed is filtered off, washed with water and dissolved in methylene chloride. The methylene chloride solution is dried over sodium sulfate and evaporated, and the residue is recrystallized from methylene chloride/hexane. There is obtained 4-hydroxy-3-methoxy-5-nitro-4'-(trifluoromethyl)benzophenone of melting point 172°.

e) 2.0 g of 4-hydroxy-3-methoxy-5-nitro-4'-(trifluoromethyl)benzophenone (dissolved in 20 ml of 33 percent hydrobromic acid in glacial acetic acid) are stirred at 90° for 18 hours. Thereupon, 20 ml of 48 percent aqueous hydrobromic acid are added thereto, whereupon the mixture is stirred at 110° for an additional 18 hours. The reaction mixture is subsequently evaporated under reduced pressure and the residue is recrystallized from water. There is obtained 3,4-dihydroxy-5-nitro-4'-(trifluoromethyl)benzophenone of melting point 116°-118°.

EXAMPLE 66 a) 18.7 g of 4-hydroxy-3-methoxy-5-nitro-4'-(trifluoromethyl)benzophenone (dissolved in 250 ml of tetrahydrofuran) are treated at room temperature with 27.5 ml of 2N potassium hydroxide solution, whereupon the mixture is evaporated. The residue is treated with 200 ml of toluene, whereupon the mixture is again evaporated. Thereupon, the mixture is heated with 400 ml of toluene for 4 hours with the separation of water and under reflux. 100 ml of toluene are distilled and 10 ml of dimethylformamide and 20 ml of dimethyl sulfate (freshly distilled) are added, whereupon the mixture is heated under reflux for 5 hours. 300 ml of 1N sodium hydroxide solution are subsequently added at 20°. The reaction mixture is stirred for 30 minutes and treated with 200 ml of ether. The organic phase is separated; the aqueous phase is extracted twice more with 100 ml of ether; the combined ether phases are dried over sodium sulfate and evaporated, and the residue is chromatographed on 70 g of silica gel with methylene chloride. After recrystallization from methylene chloride/hexane there is obtained 3,4-dimethoxy-5-nitro-4'-(trifluoromethyl)benzophenone of melting point 115°.

b) 49.5 g of tin dichloride dihydrate are added to 16.0 g of 3,4-dimethoxy-5-nitro-4'-(trifluoromethyl)benzophenone (dissolved in 300 ml of ethanol), whereupon the mixture is stirred at 75° for 30 minutes. Thereupon, the reaction mixture is poured into 800 ml of ice-water. It is neutralized with 28 percent sodium hydroxide solution and extracted three times with 600 ml of methylene chloride. The combined methylene chloride phases are washed with water, dried over sodium sulfate and evaporated. After recrystallization from methylene chloride/hexane there is obtained 5-amino-3,4-dimethoxy-4'-(trifluoromethyl)benzophenone of melting point 95°-96°.

c) 3.25 g of 5-amino-3,4-dimethoxy-4'-(trifluoromethyl)-benzophenone (dissolved in 50 ml of acetone) are evaporated under reduced pressure after the addition of 15 ml of 2N sulfuric acid. The thus-obtained residue is suspended in 20 ml of acetic acid, diluted with 100 ml of water and treated at 5° with a solution of 700 mg of sodium nitrite in 10 ml of water. It is stirred at 5° for 1 hour. Thereupon, the diazonium salt solution is filtered, added at 5° to a solution of 2.0 g of sodium cyanide and 1.0 g of copper(I) cyanide in 20 ml of water and stirred at 5° for 1 hour. Thereupon, 200 ml of methylene chloride are added thereto. Insoluble constituents are filtered off. The phases are separated; the aqueous phase is extracted twice more with 100 ml of methylene chloride. The combined methylene chloride phases are washed with water, dried over sodium sulfate and evaporated. The residue is chromatographed on 30 g of silica gel with methylene chloride. After recrystallization from methylene chloride/hexane, there is obtained 5-cyano-3,4-dimethoxy-4'-(trifluoromethyl)benzophenone of melting point 130°.

d) 1.5 g 5-cyano-3,4-dimethoxy-4'-(trifluoromethyl)-benzophenone (dissolved in 75 ml of methylene chloride) are treated at 5° with 2.18 ml of boron tribromide, whereupon the mixture is stirred at room temperature for 18 hours. The reaction mixture is subsequently diluted with 50 ml of methylene chloride. The mixture is heated under reflux for an additional 4 hours, treated at −70° with 15 ml of methanol, stirred at room temperature for 2 hours, evaporated, the residue is dried in vacuo and partitioned between ethyl acetate and ice-water. The aqueous phase is extracted twice more with ethyl acetate. The combined ethyl acetate phases are dried over sodium sulfate and evaporated. The thus-obtained material is stirred at 130° for 6 hours with 10 ml of acetic anhydride and 1 ml of pyridine. The mixture is evaporated and the residue is partitioned between ice-water and methylene chloride. The methylene chloride phase is dried over sodium sulfate and evaporated, and the residue is chromatographed on 30 g of silica gel with methylene chloride. The thus-obtained diacetate is dissolved in 10 ml of methanol. The solution is treated with 4.2 ml of 1N sodium hydroxide solution, stirred at 0° for 1 hour, neutralized with acetic acid, evaporated and partitioned between ethyl acetate and saturated sodium chloride solution. The ethyl acetate phases are dried over sodium sulfate and evaporated, and the residue is recrystallized from methylene chloride. There is obtained 5-cyano-3,4-dihydroxy-4'-(trifluoromethyl)benzophenone of melting point 204°-206°.

In an analogous manner:

a1) From 2'-fluoro-4-hydroxy-3-methoxy-5-nitrobenzophenone there is obtained 3,4-dimethoxy-2'-fluoro-5-nitrobenzophenone of m.p. 86°-88° (from ether/low-boiling petroleum ether), b1) from 3,4-dimethoxy-2'-fluoro-5-nitrobenzophenone there is obtained 5-amino-3,4-dimethoxy-2'-fluorobenzophenone of m.p. 93°-95° (from ether/low-boiling petroleum ether), c1) from 5-amino-3,4-dimethoxy-2'-fluorobenzophenone there is obtained 5-benzoyl-2,3-dimethoxy-2'-fluorobenzonitrile of m.p. 132°-134° (from methylene chloride/low-boiling petroleum ether) and d1) from 5-benzoyl-2,3-dimethoxy-2'-fluorobenzonitrile there is obtained 5-benzoyl-2,3-dihydroxy-2'-fluorobenzonitrile of m.p. 228°-230° (from ether/low-boiling petroleum ether).

In an analogous manner:

b2) from 3,4-dimethoxy-5-nitrobenzophenone there is obtained 5-amino-3,4-dimethoxybenzophenone as an amorphous solid, c2) from 5-amino-3,4-dimethoxybenzophenone there is obtained 5-benzoyl-2,3-dimethoxybenzonitrile of m.p. 98°-100° (from ether/hexane) and d2) from 5-benzoyl-2,3-dimethoxybenzonitrile there is obtained 5-benzoyl-2,3-dihydroxybenzonitrile of m.p. 212°-214° (from ethyl acetate/ether).

EXAMPLE 67 a) A solution of 16.0 g of 3,4-dimethoxy-5-nitrobenzoyl chloride in 80 ml of pyridine is added dropwise to a solution of 2.68 g of 1-methylimidazole and 6.6 g of triethylamine in 80 ml of pyridine, whereupon the mixture is stirred at 60° for 3 hours. After treatment with 1.70 ml of 3N sodium hydroxide solution the mixture is stirred for an additional 1 hour and subsequently poured into ice-water. The separated grey crystals are filtered under suction and taken up in ethyl acetate, whereupon the organic phase is dried over magnesium sulfate and the solvent is distilled. After recrystallization from ethyl acetate/hexane there is obtained 3,4-dimethoxy-5-nitrophenyl (1-emthylimidazol-2-yl) ketone in the form of colorless crystals of m.p. 144°-145°.

b) 5.0 g of 3,4-dimethoxy-5-nitrophenyl (1-methylimidazol-2-yl) ketone are treated with 50 ml of hydrobromic acid (48%), whereupon the mixture is stirred under reflux temperature for 2 hours. After cooling the separated precipitate is filtered under suction, washed with ice-water and recrystallized from ethanol. There is obtained 3,4-hydroxy-5-nitrophenyl (1-methylimidazol-2-yl) ketone hydrobromide in the form of yellow crystals of decomposition point >240°.

EXAMPLE 68

In analogy to Example 67, from 3,4-dimethoxy-5-nitrobenzoyl chloride and 1-benzylimidazole there is obtained 1-benzylimidazol-2-yl (3,4-dimethoxy-5-nitrophenyl) ketone in the form of colorless crystals of m.p. 134°-135° (from methylene chloride/hexane) and therefrom with hydrogen bromide there is obtained 1-benzylimidazol-2-yl (3,4-dihydroxy-5-nitrophenyl) ketone hydrobromide as yellow crystals of m.p. 218°-219° (dec.).

EXAMPLE 69 a) A solution of 10.0 g of 1-[(benzyloxy)-methyl]imidazole in 50 ml of acetonitrile is added dropwise within 10 minutes while cooling with ice to a solution of 13.0 g of 3,4-dimethoxy-5-nitrobenzoyl chloride and 5.4 g of triethylamine in 80 ml of acetonitrile so that the temperature does not exceed 25°. The mixture is subsequently stirred for an additional 3 hours, whereupon the solvent is distilled. After treatment with water, the mixture is extracted with ethyl acetate. After two-fold washing with water, the organic phase is dried over sodium sulfate and evaporated. The resulting oil is chromatographed on 600 g of silica gel with toluene/ethyl acetate (95:5). There is obtained 1-[(benzyloxy)methyl]imidazol-2-yl (3,4-dimethoxy-5-nitrophenyl) ketone as a yellowish oil b) In analogy to Example 67b) there is obtained after treatment with hydrobromic acid 3,4-dihydroxy-5-nitrophenyl (imidazol-2-yl) ketone hydrobromide as yellow crystals of m.p. 247°-248°.

EXAMPLE 70 a) A solution of 25.0 g of 3-bromoquinoline is dissolved in 200 ml of dry ether and cooled to −60°. At this temperature there are added dropwise within 15 minutes 75.1 ml of a 1.6 molar solution of n-butyllithium, whereupon the mixture is stirred for 10 minutes. A solution of 26.5 g of vanillin benzyl ether in 250 ml of dry ether is added dropwise thereto at −60°, the mixture is subsequently stirred at room temperature of 3 hours, poured into about 1.5 l of ice-water and extracted three times with 600 ml of ethyl acetate each time. The organic phase is washed with water, dried over sodium sulfate and evaporated. The resulting oil is chromatographed on 1 kg of silica gel with methylene chloride/ethyl acetate (1:1). The crystalline crude product obtained is recrystallized form ethyl acetate. There is obtained α-[4-(benzyloxy)-3-methoxyphenyl]-3-quinolinemethanol in the form of colourless crystals of m.p. 124°-125°.

b) A solution of 6.2 g of α-[4-(benzyloxy)-3-methoxyphenyl]-3-quinolinemethanol in 200 ml of methylene chloride is treated with 62 g of manganese dioxide and stirred at the reflux temperature 2 hours. After cooling the precipitate is filtered under suction and washed with methylene chloride. The filtrate is evaporated and the oil obtained is dissolved in hot ether, whereupon the solution is treated with a small amount of pentane. The separated crystals are filtered under suction. There is obtained 4-(benzyloxy)-3-methoxyphenyl (3-quinolinyl) ketone in the form of colorless crystals of m.p. 110°-111°.

c) 11.0 g of 4-(benzyloy)-3-methoxyphenyl (3-quinolinyl) ketone are treated with 50 ml of trifluoroacetic acid, whereupon the mixture is stirred at room temperature for 2 hours. After distillation of the trifluoroacetic acid, the residue is treated twice with 50 ml of ethanol each time and the solvent is distilled each time. The oil obtained crystallizes upon treatment with ethanol. After recrystallization from ethanol, there is obtained 4-hydroxy-3-methoxypyenyl (3-quinolinyl) ketone in the form of yellowish crystals of m.p. 196°-197°.

d) A solution of 1.91 ml of 65 percent nitric acid in 20 ml of glacial acetic acid is added dropwise to a solution of 5.5 g of 4-hydroxy-3-methoxyphenyl (3-quinolinyl) ketone in 300 ml of glacial acetic acid at 150° and the mixture is then stirred at this temperature for an additional 2 hours. The mixture is then poured into ice-water and extracted three times with 300 ml of ethyl acetate each time. The organic phase is washed five times with 100 ml of water each time, dried over sodium sulfate and evaporated. After treatment of the residue with ethyl acetate, there is obtained 4-hydroxy-3-methoxy-5-nitrophenyl (3-quinolinyl) ketone in the form of yellow crystals of m.p. 220°-221° (dec.).

e) 820 mg of 4-hydroxy-3-methoxy-5-nitrophenyl (3-quinolinyl) ketone are treated with 50 ml of 48 percent hydrobromic acid and held at the reflux temperature for 3 hours. After distillation of the hydrobromic acid at 50°, the residue is treated with 70 ml of hot water and the insoluble constituent is filtered under suction. There is obtained 3,4-dihydroxy-5-nitrophenyl (3-quinolinyl) ketone hydrobromide in the form of yellow crystals of m.p. 270° (dec.).

EXAMPLE 71

In analogy to Example 70 there is obtained α-[4-(benzyloxy)-3-methoxyphenyl]-4-quinolinemethanol as colorless crystals of m.p. 117°–118° (ethyl acetate), therefrom with manganese dioxide there is obtained 4-(benzyloxy)-3-methoxyphenyl (4-isoquinolinyl) ketone as colorless crystals of m.p. 126.5°–127.5°, therefrom with trifluoroacetic acid there is obtained 4-hydroxy-3-methoxyphenyl (4-isoquinolinyl) ketone as yellow crystals of m.p. 197.5°–198.5° and therefrom by nitration with nitric acid in glacial acetic acid and subsequent treatment with hydrobromic acid, there is obtained 3,4-dihydroxy-5-nitrophenyl (4-isoquinolinyl) ketone hydrobromide as yellow crystals of m.p. 256° (dec.).

EXAMPLE 72

In analogy to Example 70 there is obtained α-[4-(benzyloxy)-3-methoxyphenyl]-2-napthhalenemethanol as colorless crystals (ethyl acetate/hexane) of m.p. 113°–114°, therefrom with manganese dioxide there is obtained 4-(benzyloxy)-3-methoxyphenyl (2-naphthyl) ketone as colorless crystals (ethyl acetate/hexane) of m.p. 104°–105°, therefrom by treatment with trifluoroacetic acid and nitration with nitric acid in glacial acetic acid there is obtained 4-hydroxy-3-methoxy-5-nitrophenyl (2-nephthyl) ketone as yellow crystals of m.p. 187°–188° and therefrom by treatment with hydrobromic acid there is obtained 3,4-dihydroxy-5-nitrophenyl (2-naphthyl) ketone as yellow crystals of m.p. 814°–185°.

EXAMPLE 73 a) A solution of 20.0 g of 3-phenylpropyl bromide in 300 ml of ether is treated at −60° while stirring within 15 minutes with a solution of 71.8 ml of tert.butyllithium (1.4 molar) in pentane. After 10 minutes there is added dropwise at this temperature within 15 minutes a solution of 22.14 g of vanillin benzyl ether in 200 ml of ether, whereupon the mixture is stirred for an additional 2 hours. The mixture is poured into 1 l of ice-water and extracted three times with 500 ml of ethyl acetate each time. The organic phase is washed twice with 200 ml of water each time, dried over sodium sulfate and evaporated. The oil obtained is chromatographed on 1 kg of silica gel with methylene chloride. The crystals obtained are recrystallized from ether/pentane. There is obtained 4-(benzyloxy)-3-methoxy-α-(3-phenylpropyl)-benzyl alcohol in the form of colorless crystals of m.p. 71°–73°.

b) A solution of 9.0 g of 4-(benzyloxy)-3-methoxy-α-(3-phenylpropyl)benzyl alcohol in 250 ml of methylene chloride is treated with 90 g of manganese dioxide and held at the reflux temperature for 2 hours. After cooling, the precipitate is filtered under suction and washed with methylene chloride. The filtrate is evaporated and the residue is recrystallized from ethyl acetate/ether. There is obtained 4'-(benzyloxy)-3'-methoxy-4-phenylbutyrophenone in the form of colorless crystals of m.p. 81°–82°.

c) A solution of 7.0 g of 4'-(benzyloxy)-3'-methoxy-4-phenylbutyrophenone in 40 ml of 33 percent hydrobromic acid in glacial acetic acid is stirred at room temperature for 5 hours and subsequently poured into 500 ml of ice-water. The solution is adjusted to pH 6.0 by the addition of conc. ammonia and extracted three times with 250 ml of ethyl acetate each time. The organic phase is washed three times with 50 ml of water each time, dried over sodium sulfate and evaporated. The oil obtained is dissolved in 20 ml of ether, whereupon the solution is treated with hexane until it becomes turbin and is left to crystallize out. There is obtained colorless 4'-hydroxy-3'-methoxy-4-phenylbutyrophenone of m.p. 91°–92°.

d) A solution of 0.79 ml of 65 percent nitric acid in 25 ml of glacial acetic acid is added dropwise to a solution of 2.2 g of 4'-hydroxy-3'-methoxy-4-phenylbutyrophenone in 25 ml of glacial acetic acid and the mixture is stirred at room temperature for an additional 2 hours. The mixture is poured into 150 ml of ice-water and, after treatment with 20 ml of 3N hydrochloric acid, extracted three times with 75 ml of ethyl acetate each time. The organic phase is washed with water, dried over sodium sulfate and evaporated. The crude product obtained is taken up in ethyl acetate and filtered over 75 g of silica gel. After recrystallization from acetonitrile, there is obtained 4'-hydroxy-3'-methoxy-5'-nitro-4-phenylbutyrophenone in the form of yellow crystals of m.p. 120°–121°.

e) 1.0 g of 4'-hydroxy-3'-methoxy-5'-nitro-4-phenylbutrophenone is held at 200° for 1 hour with 8 g of pyridine hydrochloride. The reaction mixture is poured while still warm into ice-water and extracted with ethyl acetate. The organic phase is washed with 1N hydrochloric acid and subsequently with water, dried over sodium sulfate and evaporated. The dark residue obtained is chromatographed on a 30-fold amount of silica gel with ethyl acetate. From methylene chloride/hexane there is obtained 3',4'-dihydroxy-5'-nitro-4-phenylbutyrophenone in the form of yellow crystals of m.p. 118°–119°.

EXAMPLE 74 a) A solution of 14.68 g of potassium cyanide in 20 ml of water is added to a solution of 10.0 g of 3,4-dimethoxy-5-nitrobenzaldehyde in 100 ml of dioxane. 18.81 ml of 37 percent hydrochloric acid are now added dropwise thereto within 30 minutes while stirring vigorously. After the addition of 120 ml of ether, the excess hydrogen cyanide gas is driven off by passing argon through the mixture. The reaction mixture is filtered a siliceous earth filter aid, and the organic phase is washed with water dried over sodium sulfate and evaporated. The α-hydroxy-3,4-dimethoxy-phenylacetonitrile (yellowish oil) which is formed is dissolved in 200 ml of ether, whereupon the solution is treated with 20 ml of ethanol, cooled to 0° and hydrochloric acid gas is passed in for 30 minutes. After 3 hours, the separated colorless precipitate is filtered under suction and recrystallized from ethanol/ether. There is obtained ethyl (3,4-dimethoxy-5-nitrophenyl)hydroxy-acetimidate hydrochloride.

b) 19.7 g of ethyl (3,4-dimethoxy-5-nitrophenyl)hydroxyacetimidate are dissolved in 500 ml of ethanol, 6.73 g of o-phenylenediamine are added, the mixture is stirred at room temperature for 2 hours and subsequently held at the reflux temperature overnight. After distillation of the solvent, the residue is treated with 50 ml of water, made alkaline with sodium carbonate solution and extracted twice with 250 ml of methylene chloride each time. The organic phase is washed with water, dried over sodium sulfate and evaporated. The orange residue obtained is chromatographed on 400 g of silica gel with methylene chloride/ethyl acetate (1:1). From ether/hexane there is obtained α-(3,4-dimethoxy-5- nitrophenyl)-2-benzimidazolemethanol in the form of yellowish crystals of m.p. 50° (dec.).

c) 13.2 g of α-(3,4-dimethoxy-5-nitrophenyl)-2-benzimidazolemethanol are dissolved in 200 ml of methylene chloride and, after treatment with 130 g of manganese dioxide, the mixture is stirred at the reflux temperature for 2 hours. After filtration, the solvent is distilled. There is obtained 2-benzimidazolyl (3,4-dimethoxy-5-nitrophenyl) ketone in the form of yellowish crystals of m.p. 212°-213°.

d) 1.0 g of 2-benzimidazolyl (3,4-dimethoxy-5-nitrophenyl) ketone and 8.0 g of pyridine hydrochloride are held at 200° for 60 minutes. The dark solution is poured while still warm into ice-water and extracted three times with 100 ml of ethyl acetate each time. The organic phase is washed with water, dried over sodium sulfate and evaporated. After recrystallization from ethyl acetate/hexane, there is obtained 2-benzimidazolyl (3,4-dihydroxy-5-nitrophenyl) ketone in the form of yellow crystals of m.p. 240°-250°.

EXAMPLE 75 a) 30.0 g of 3,4-dimethoxy-5-nitrobenzoic acid are dissolved in 250 ml of tetrahydrofuran and, after the addition of 21.85 g of 1,1'-carbonyldiimidazole, the mixture is stirred at the reflux temperature for 2 hours. The mixture is poured into 300 ml of ice-water and the precipitated crystals are filtered under suction after stirring for 30 minutes. The crystals are taken up in methylene chloride, whereupon the organic phase is washed with water, dried over sodium sulfate and evaporated. After crystallization from methylene chloride/hexane, there is obtained 1-(3,4-dimethoxy-5-nitrobenzoyl)imidazole in the form of colorless crystals of m.p. 136°-137°.

b) 10.0 g of 1-(3,4-dimethoxy-5-nitrobenzoyl)imidazole in 50 ml of dimethylformamide are treated with 6.95 g of acetamidoxime, whereupon the mixture is stirred at 70° for 1 hour. After cooling, the mixture is poured into 500 ml of ice-water and stirred for 30 minutes. The separated crystals are filtered under suction and washed with water. After crystallization from ethyl acetate there is obtained N'-[(3,4-dimethoxy-5-nitrobenzoyl)oxy]acetamidine in the form of colorless crystals of m.p. 165°-166°.

c) 2.0 g of N'-[(3,4-dimethoxy-5-nitrobenzoyl)oxy]acetamidine are held at reflux temperature for 1 hour in 20 ml of glacial acetic acid. After distillation of the acetic acid, the crystalline residue is recrystallized from ether/hexane. There is obtained 5-(3,4-dimethoxy-5-nitrophenyl)-3-methyl-1,2,4-oxadiazole in the form of colorless crystals of m.p. 111°.

d) 2.5 g of 5-(3,4-dimethoxy-5-nitrophenyl)-3-methyl-1,2,4-oxadiazole are dissolved in 70 ml of methylene chloride. After cooling to −60° there is added dropwise thereto within 20 minutes while stirring a solution of 23.62 g of boron tribromide in 50 ml of methylene chloride, whereupon the mixture is held at the reflux temperature for 48 hours. After cooling to −60°, the mixture is treated with 60 ml of ethanol and subsequently stirred at room temperature for 30 minutes. The yellow solution is evaporated to dryness, whereupon the residue is treated three times with 100 ml of toluene/ethanol (1:1) each time and the solvent is distilled each time. After crystallization from ethanol, there is obtained 5-(3-methyl-1,2,4-oxadiazol-5-yl)-3-nitropyrocatechol in the form of yellow crystals of m.p. 201°-202°.

EXAMPLE 76 a) 143.8 ml of n-butyllithium solution (1.53M in hexane) are added dropwise at −70° within 30 minutes to 35.0 g of 1-bromo-2-fluorobenzene (dissolved in 600 ml of tetrahydrofuran). After stirring at −70° for 60 minutes 48.5 g of 3-methoxy-4-benzyloxybenzaldehyde (dissolved in 450 ml of tetrahydrofuran) are added dropwise thereto during 30 minutes. The reaction mixture is stirred at −70° for 2 hours and at 0° for 30 minutes, poured into a mixture of ice and 150 ml of 2N sulfuric acid and extracted three times with 500 ml of ether. The combined ether phases are washed with saturated sodium chloride solution, dried over sodium sulfate and evaporated. There is obtained 4-(benzyloxy)-2'-fluoro-3'-methoxybenzhydrol as a yellowish oil which can be used directly in the subsequent reaction step.

In an analogous manner:

a1) From 3-methoxy-4-benzyloxybenzaldehyde and 1-bromo-3-fluorobenzene there is obtained 4-(benzyloxy-3'-fluoro-3-methoxybenzhydrol as an oil;

a2) from 3-methoxy-4-benzyloxybenzaldehyde and 1-bromo-4-fluorobenzene there is obtained 4-(benzyloxy)-4'-fluoro-3-methoxybenzhydrol as an oil;

a3) from 3-methoxybenzhydrol as an oil;

a4) from 3-methoxy-4-benzyloxybenzaldehyde and 1-bromo-2-chlorobenzene there is obtained 4-(benzyloxy)-2'-chloro-3-methoxybenzhydrol as an oil;

a5) from 3-methoxy-4-benzyloxybenzaldehyde and 1-bromo-3-chlorobenzene there is obtained 4-(benzyloxy)-3'-chloro-3-methoxybenzhydrol as an oil;

a6) from 3-methoxy-4-benzyloxybenzaldehyde and 1-bromo-4-chlorobenzene there is obtained 4-(benzyloxy)-4'-chloro-3-methoxybenzhydrol as an oil;

a7) from 4-benzyloxy-3-methoxybenzaldehyde and 2-bromotoluene there is obtained 4-(benzyloxy)-3-methoxy-2'-methylbenzhydrol as an oil;

a8) from 3-methoxy-4-benzyloxybenzaldehyde and 4-bromotoluene there is obtained 4-(benzyloxy)-3-methoxy-4'-methylbenzhydrol as an oil;

a9) from 3-methoxy-4-benzyloxybenzaldehyde and 1-bromobenzonitrile there is obtained 4-(benzyloxy)-2'-cyano-3-methoxybenzhydrol as an oil and a10) from 3-methoxy-4-benzyloxybenzaldehyde and 1-bromo-2-trifluoromethylbenzene there is obtained 4-(benzlyoxy)-3-methoxy-2'-(trifluoromethyl)benzhydrol as an oil.

b) 69.8 g of 4-(benzyloxy)-2'-fluoro-3-methoxybenzhydrol (dissolved in 600 ml of methylene chloride) are treated within 30 minutes at 20° with 45.3 g of pyridinium chlorochromate and stirred at 20° for 3 hours. The precipitate formed is subsequently filtered and washed with methylene chloride. The filtrate is evaporated and the residue is filtered on 100 g of silica gel with ether. After recrystallization from ether, there is obtained 4-(benzyloxy)-2'-fluoro-3-methoxybenzophenone of m.p. 118°-120°.

In an analogous manner:

b1) From 4-(benzyloxy)-3'-fluoro-3-methoxybenzhydrol there is obtained 4-(benzyloxy)-3'-fluoro-3-methoxybenzophenone as an amorphous solid;

b2) from 4-(benzyloxy)-4'-fluoro-3-methoxybenzhydrol there is obtained 4-(benzyloxy)-4'-fluoro-3-methoxybenzophenone of m.p. 99°-101° (from ether/hexane);

b3) from 4-(benzyloxy)-2',6'-difluoro-3-methoxybenzhydrol there is obtained 4-(benzyloxy)-2',6'- difluoro-3-methoxybenzophenone of m.p. 139°–141° (from methylene chloride/ether);

b4) from 4-(benzyloxy)-2'-chloro-3-methoxybenzhydrol there is obtained 4-(benzyloxy)-2'-chloro-3-methoxybenzophenone of m.p. 128°–130° (from ether);

b5) from 4-(benzyloxy)-3'-chloro-3-methoxybenzhydrol there is obtained 4-(benzyloxy)-3'-chloro-3-methoxybenzophenone as an amorphous solid;

b6) from 4-(benzyloxy)-4'-chloro-3-methoxybenzhydrol there is obtained 4-(benzyloxy)-4'-chloro-3-methoxybenzophenone of m.p. 106°–108° (from methylene chloride/hexane);

b7) from 4-(benzyloxy)-3-methoxy-2'-methylbenzhydrol there is obtained 4-(benzyloxy)-3-methoxy-2'-methylbenzophenone of m.p. 86°–88° (from isopropyl ether);

b8) from 4-(benzyloxy)-3-methoxy-4'-methylbenzhydrol there is obtained 4-(benzyloxy)-3-methoxy-4'-methylbenzophenone of m.p. 79°–81° (from ether/hexane);

b9) from 4-(benzyloxy)-2'-cyano-3-methoxybenzhydrol there is obtained 4-(benzyloxy)-2'-cyano-3-methoxybenzophenone as an amorphous solid and b10) from 4-(benzyloxy)-3-methoxy-2'-(trifluoromethyl)benzyhydrol there is obtained 4-(benzyloxy)-3-methoxy-2'-(trifluoromethyl)benzophenone of m.p. 103°–105° (from ether).

c) 170 ml of 33 percent hydrobromic acid in glacial acetic acid are added at 20°–25° within 20 minutes to 42.4 g of 4-(benzyloxy)-2'-fluoro-3-methoxybenzophenone (dissolved in 450 ml of methylene chloride). After stirring at 20° for 1.5 hours, the reaction mixture is poured into 750 ml of ice-water; the methylene chloride phase is separated and the aqueous phase is extracted twice more with 200 ml of methylene chloride. The combined methylene chloride phases are washed with 1200 ml of water, dried over sodium sulfate and evaporated. In order to remove the resulting benzyl bromide, the oily residue is treated with hexane and decanted off. There is obtained 2'-fluoro-4-hydroxy-3-methoxybenzophenone as a yellowish oil which can be used directly in the subsequent reaction step.

In an analogous manner:

c1) From 4-(benzyloxy)-3'-fluoro-3-methoxybenzophenone there is obtained 3'-fluoro-4-hydroxy-3-methoxybenzophenone of m.p. 133°–135° (from methylene chloride/low-boiling petroleum ether);

c2) from 4-(benzyloxy)-4'-fluoro-3-methoxybenzophenone there is obtained 4'-fluoro-4-hydroxy-3-methoxybenzophenone of m.p. 139°–141° (from ether);

c3) from 4-(benzyloxy)-2',6'-difluoro-4-hydroxy-3-methoxybenzophenone of m.p. 130°–132° (from methylene chloride/low-boiling petroleum ether);

c4) from 4-(benzyloxy)-2'-chloro-3-methoxybenzophenone there is obtained 2'-chloro-4-hydroxy-3-methoxybenzophenone as an amorphous solid;

c5) from 4-(benzyloxy)-3'-chloro-3-methoxybenzophenone there is obtained 3'-chloro-4-hydroxy-3-methoxybenzophenone of m.p. 136°–138° (from methylene chloride);

c6) from 4-(benzyloxy)-4'-chloro-3-methoxybenzophenone there is obtained 4'-chloro-4-hydroxy-3-methoxybenzophenone of m.p. 114°–116° (from methylene chloride/low-boiling petroleum ether);

c7) from 4-(benzyloxy)-3-methoxy-2'-methylbenzophenone there is obtained 4-hydroxy-3-methoxy-2'-methylbenzophenone of m.p. 103°–105° (from isopropyl ether);

c8) from 4-(benzyloxy)-3-methoxy-4'-methylbenzophenone there is obtained 4-hydroxy-3-methoxy-4'-methylbenzophenone of m.p. 103°–105° (from ether/low boiling petroleum ether);

c9) from 4-(benzyloxy)-2'-cyano-3-methoxybenzophenone there is obtained 2'-cyano-4-hydroxy-3-methoxybenzophenone of m.p. 124°–126° from ether/n-hexane) and c10) from 4-(benzyloxy)-3-methoxy-2'-(trifluoromethyl)benzophenone there is obtained 4-hydroxy-3-methoxy-2'-(trifluoromethyl)benzophenone of m.p. 115°–117° (from ether).

d) 7.8 ml of 65 percent nitric acid are added dropwise at 20° within 20 minutes to 29.4 g of 2'-fluoro-4-hydroxy-3-methoxybenzophenone (dissolved in 450 ml of acetic acid). After stirring for 1.5 hours, the reaction mixture is poured into 2 l of ice-water and the precipitate formed is filtered off, washed with water and dissolved in methylene chloride. The methylene chloride solution is washed with water, dried over sodium sulfate and evaporated. The residue is recrystallized from methanol. There is obtained 2'-fluoro-4-hydroxy-3-methoxy-5-nitrobenzophenone of m.p. 127°–129°.

In an analogous manner:

d1) From 3'-fluoro-4-hydroxy-3-methoxybenzophenone there is obtained 3'-fluoro-4-hydroxy-3-methoxy-5-nitrobenzophenone of m.p. 168°–170° (from methanol);

d2) from 4'-fluoro-4-hydroxy-3-methoxybenzophenone there is obtained 4'-fluoro-4-hydroxy-3-methoxy-5-nitrobenzophenone of m.p. 126°–128° (from ether);

d3) from 2',6'-difluoro-4-hydroxy-3-methoxybenzophenone there is obtained 2',6'-difluoro-4-hydroxy-3-methoxy-5-nitrobenzophenone of m.p. 147°–149° (from methanol);

d4) from 2'-chloro-4-hydroxy-3-methoxybenzophenone there is obtained 2'-chloro-4-hydroxy-3-methoxy-5-nitrobenzophenone of m.p. 123°–125° (from ether);

d5) from 3'-chloro-4-hydroxy-3-methoxybenzophenone there is obtained 3'-chloro-4-hydroxy-3-methoxy-5-nitrobenzophenone of m.p. 152°–154° (from methanol);

d6) from 4'-chloro-4-hydroxy-3-methoxyphenone there is obtained 4'-chloro-4-hydroxy-3-methoxy-5-nitrobenzophenone of m.p. 128°–131° (from methylene chloride/low-boiling petroleum ether);

d7) from 4-hydroxy-3-methoxy-2'-methylbenzophenone there is obtained 4-hydroxy-3-methoxy-2'-methyl-5-nitrobenzophenone of m.p. 125°–127° (from ethanol);

d8) from 4-hydroxy-3-methoxy-4'-methoxybenzophenone there is obtained 4-hydroxy-3-methoxy-4'-methyl-5-nitrobenzophenone of m.p. 137°–139° (from methylene chloride/ether);

d9) from 2'-cyano-4-hydroxy-3-methoxybenzophenone there is obtained 2'-cyano-4-hydroxy-3-methoxy-5-nitrobenzophenone of m.p. 163°–164° (from methanol);

d10) from 4-hydroxy-3-methoxy-2'-(trifluoromethyl)-benzophenone there is obtained 4-hydroxy-3-methoxy-5-nitro-2'-(trifluoromethyl)benzophenone of m.p. 138°–140° (from methylene chloride/low-boiling petroleum ether);

d11) from 4-hydroxy-3,4'-dimethoxybenzophenone there is obtained 4-hydroxy-3',4'-dimethoxy-5-nitrobenzophenone of m.p. 134°–136° (from methanol) and d12) from 4-hydroxy-3,3',4'-trimethoxybenzophenone there is obtained 4-hydroxy-5-nitro-3,3',4'-trimethoxybenzophenone of m.p. 178°–180° (from methanol).

e) 24.8 g of 2'-fluoro-4-hydroxy-3-methoxy-5-nitrobenzophenone (dissolved in 120 ml of glacial acetic acid, 100 ml of 33 percent hydrobromic acid in glacial acetic acid and 68 ml of 48 percent aqueous hydrobromic acid) are boiled under reflux for 4 hours. The reaction mixture is subsequently evaporated under reduced pressure and the residue is distilled with toluene. The residue is dissolved in methylene chloride, washed with water, dried over sodium sulfate, filtered and evaporated. The product is crystallized from methylene chloride/low-boiling petroleum ether. There is obtained 2'-fluoro-3,4-dihydroxy-5-nitrobenzophenone of m.p. 169°-171°.

In an analogous manner:

e1) From 3'-fluoro-4-hydroxy-3-methoxy-5-nitrobenzophenone there is obtained 3'-fluoro-3,4-dihydroxy-5-nitrobenzophenone of m.p. 124°-126° (from methylene chloride);

e2) from 4'-fluoro-4-hydroxy-3-methoxy-5-nitrobenzophenone there is obtained 4'-fluoro-3,4-dihydroxy-5-nitrobenzophenone of m.p. 171°-173° (from methylene chloride);

e3) from 2',6'-difluoro-4-hydroxy-3-methoxy-5-nitrobenzophenone there is obtained 2',6'-difluoro-3,4-dihydroxy-5-nitrobenzophenone of m.p. 194°-196° (from methanol);

e4) from 2'-chloro-4-hydroxy-3-methoxy-5-nitrobenzophenone there is obtained 2'-chloro-3,4-dihydroxy-5-nitrobenzophenone of m.p. 129°-131° (from methylene chloride/low-boiling petroleum ether);

e5) from 3'-chloro-4-hydroxy-3-methoxy-5-nitrobenzophenone there is obtained 3'-chloro-3,4-dihydroxy-5-nitrobenzophenone of m.p. 143°-145° (from methylene chloride/low-boiling petroleum ether);

e6) from 4'-chloro-4-hydroxy-3-methoxybenzophenone there is obtained 4'-chloro-3,4-dihydroxybenzophenone of m.p. 174°-176° (from methylene chloride);

e7) from 4-hydroxy-3-methoxy-2'-methyl-5-nitrobenzophenone there is obtained 3,4-dihydroxy-2'-methyl-5-nitrobenzophenone of m.p. 164°-166° (from methylene chloride);

e8) from 4-hydroxy-3-methoxy-4'-methyl-5-nitrobenzophenone there is obtained 3,4-dihydroxy-4'-methyl-5-nitrobenzophenone of m.p. 146°-148° (from methylene chloride);

e9) 2'-cyano-4-hydroxy-3-methoxy-5-nitrobenzophenone there is obtained 2'-cyano-3,4-dihydroxy-5-nitrobenzophenone of m.p. 159°-161° (from methanol);

e10) from 4-hydroxy-3-methoxy-5-nitro-2'-(trifluoromethyl)benzophenone there is obtained 3,4-dihydroxy-5-nitro-2'-(trifluoromethyl)benzophenone of m.p. 146°-148° (from methanol);

e11) from 4-hydroxy-3,4'-dimethoxy-5-nitrobenzophenone there is obtained 5-nitro-3,4,4'-trihydroxybenzophenone of m.p. 212°-214° (from methanol/methylene chloride) and e12) from 4-hydroxy-5-nitro-3,3',4'-trimethoxybenzophenone there is obtained 5-nitro-3,3',4,4'-tetrahydroxybenzophenone of m.p. 222°-224° (from ether).

EXAMPLE 77

A suspension of 13.8 g of 2-bromo-3',4'-dihydroxy-5'-nitroacetophenone is treated with 9.0 g of 1-(phenethyl)-2-thiorea in 150 ml of n-butanol and the mixture is heated to boiling under reflux for 3 hours. After cooling to room temperature, the crystals are filtered under suction and crystallized from n-butanol. There is obtained 3-nitro-5-[2-(phenethylamino)-4-thiazolyl]-pyrocatechol hydrobromide of m.p. 249°-251°.

EXAMPLE 78

In analogy to Example 38, from 2-bromo-3',4'-dihydroxy-5'-nitroacteophenone and 2-aminobenzophenone there is obtained 2-(3,4-dihydroxy-5-nitrobenzoyl)-3-phenylindole of m.p. 196°-198° (from isopropanol).

EXAMPLE 79

A suspension of 8.3 g of 2-bromo-3',4'-dihydroxy-5'-nitroacetophenone is treated with 1-(1-adamantyl)-2-thiourea in 90 ml of n-butanol and the mixture is heated to boiling under reflux for 4 hours. After cooling to room temperature, the crystals are filtered under suction and recrystallized from n-butanol. There is obtained 5-[2-(1-adamantylamino)-5-thiazolyl]-3-nitropyrocatechol hydrobromide of m.p. 245°-247°.

EXAMPLE 80

A suspension of 2.6 g of (3,4-dihydroxy-5-nitrobenzoyl)methyl acetate in 20 ml of ethanol and 20 ml of 1N hydrochloric acid is heated to boiling under reflux for 5 hours. The reaction mixture is then evaporated, the residue is distilled with toluene and then recrystallized from ethanol. There is obtained 2,3',4'-trihydroxy-5'-nitroacetophenone of m.p. 208°-210°.

EXAMPLE 81

A solution of 4.0 g of n-hexyl 3,4-dihydroxy-5-nitrophenylglyoxylate and 1.5 g of diaminomaleonitrile in 35 ml of ethanol is heated to boiling under relfux for 24 hours. The alcohol is then distilled, the residue is dissolved in ether, washed with water, dried over sodium sulfate, filtered and evaporated. There is obtained 6-hydroxy-5-(3,4-dihydroxy-5-nitrophenyl)-2,3-pyrazinedicarbonitrile of m.p. >300° (from ether/methylene chloride).

EXAMPLE 82 a) 4.2 g of 5-(bromoacetyl)-2,3-dimethoxybenzonitrile dissolved in 150 ml of methylene chloride are treated with 8.9 ml of boron tribromide. The reaction mixture is stirred at 20° for 18 hours. It is subsequently poured into 220 ml of saturated sodium hydrogen carbonate solution and 100 g of ice, adjusted to pH 6 with glacial acetic acid and extracted with ethyl acetate. The organic phase is washed with water, dried over sodium sulfate and evaporated. There is obtained 5-(bromoacetyl)-2,3-dihydroxybenzonitrile as an amorphous solid.

b) 3.8 g of 5-(bromoacetyl)-2,3-dihydroxybenzonitrile dissolved in 25 ml of N,N-dimethylformamide are treated with N-phenylthiourea and stirred at 100° for 5 hours. Thereafter, the solvent is removed by evaporation. The residue is treated with 200 ml of 1N sodium carbonate solution and extracted three times with 100 ml of methylene chloride each time. The combined organic phases are washed with water, dried over sodium sulfate and evaporated. The residue is chromatographed on 30 g of silica gel with ethyl acetate. The thus-obtained crude product is treated with 40 ml of 1N hydrochloric acid, evaporated and crystallized from acetone. There is obtained 5-(2-anilino-4-thiazolyl)-2,3-dihydroxybenzonitrile hydrochloride of m.p. 245°-247°.

EXAMPLE 83 a) 25 ml of tert.-butyllithium solution (1.4M in hexane) are added dropwise at −70° within 10 minutes to 10 g of 4-benzyloxy)-3-methoxy-bromobenzene dissolved in 100 ml of tetrahydrofuran. After stirring at −70° for 1 hour, 5 g of quinoline-4-carbaldehyde dissolved in 50 ml of tetrahydrofuran are added dropwise within 30 minutes. The reaction mixture is stirred at −40° for 1 hour and at −5° for 1 hour, poured into 200 ml of water and adjusted to pH 4 with glacial acetic acid. The mixture is extracted three times with 50 ml of ether each time. The combined ether phases are washed with water, dried over sodium sulfate and evaporated. There is obtained α-[4(benzyloxy)-3-methoxyphenyl]-4-quinolinemethanol as an amorphous solid.

b) 9.4 g of α-[4-(benzyloxy)-3-methoxyphenyl]-4-quinolinemethanol dissolved in 200 ml of methylene chloride are treated with 6.5 g of pyridinium chlorochromate, whereupon the mixture is stirred at room temperature for 3 hours. The insoluble constituents are subsequently filtered off. The filtrate is evaporated and the residue is chromatographed on 150 g of silica gel with ethyl acetate. There is thus obtained 4-(benzyloxy)-3-methoxyphenyl 4-quinolyl ketone as an amorphous solid.

c) 15 ml of 33 percent hydrobromic acid in glacial acetic acid are added dropwise within 5 minutes at room temperature to 7.5 g of 4-(benzyloxy)-3-methoxyphenyl 4-quinolyl ketone dissolved in 150 ml of methylene chloride. After stirring at 20° for 4.5 hours, the reaction mixture is poured portionwise into 250 ml of saturated sodium bicarbonate solution. The methylene chloride phase is separated; the aqueous phase is extracted twice with 100 ml of methylene chloride each time. The combined methylene chloride phases are dried over sodium sulfate and evaporated. The residue is recrystallized from methylene chloride/hexane. There is obtained 4-hydroxy-3-methoxyphenyl 4-quinolyl ketone of m.p. 190°–192°.

d) 0.37 ml of 65 percent nitric acid is added dropwise at room temperature to 1.3 g of 4-hydroxy-3-methoxyphenyl 4-quinolyl ketone. After stirring for 3 hours the reaction mixture is poured into ice-water, adjusted to pH 6 with conc. ammonia and the precipitate formed is filtered. The thus-obtained residue is heated under reflux in 20 ml of acetonitrile, whereupon the crystals are filtered at 0°. There is obtained 4-hydroxy-3-methoxy-5-nitrophenyl 4-quinolyl ketone of m.p. 246°–248°.

e) 1g of 4-hydroxy-3-methoxy-5-nitrophenyl 4-quinilyl ketone dissolved in 30 ml of 48 percent aqueous hydrobromic acid is stirred at 100° for 18 hours. After cooling to room temperature, the reaction mixture is diluted with 30 ml of water and the precipitate is filtered under suction. There is obtained 3,4-dihydroxy-5-nitrophenyl 4-quinolyl ketone hydrobromide of m.p. 273°–275° (from acetonitrile).

EXAMPLE 84 a) 18.8 ml of n-butyllithium solution (1.6M in hexane) are added dropwise at −50° within 10 minutes to 4.03 g of thiophene dissolved in 40 ml of tetrahydrofuran. After stirring at −50° for 30 minutes 6.3 g of 3,4-dimethoxy-5-nitrobenzaldehyde dissolved in 100 ml of tetrahydrofuran are added dropwise within 30 minutes. The reaction mixture is stirred at −50° for 1 hour at 0° for 30 minutes and poured into 100 ml of 2N sulphuric acid. The mixture is extracted three times with 100 ml of ether each time; the combined ether phases are washed with sodium chloride solution, dried over sodium sulfate, filtered and evaporated. There is obtained α-(3,4-dimethoxy-5-nitrophenyl)-2-thiophenemethanol of m.p. 79°–81° (from methylene chloride/hexane).

b) 9.9 g of α-(3,4-dimethoxy-5-nitrophenyl)-2-thiophenemethanol dissolved in 300 ml of acetone are treated with 90 g of manganese dioxide and heated under reflux for 4 hours. The manganese dioxide is removed by suction filtration and the filtrate is evaporated. There is obtained 3,4-dimethoxy-5-nitrophenyl 2-thienyl ketone of m.p. 102°–104° (from methylene chloride/hexane).

c) 2 g of 3,4-dimethoxy-5-nitrophenyl 2-thienyl ketone are stirred at 100° for 8 hours in a mixture of 20 ml of 30–33 percent hydrobromic acid in glacial acetic acid and 20 ml of 48 percent aqueous hydrobromic acid. The reaction mixture is subsequently evaporated to dryness. The residue is taken up in ethyl acetate, washed with water, dried over sodium sulfate and filtered, and the filtrate is evaporated. After recrystallization from ethyl acetate/hexane there is obtained 3,4-dihydroxy-5-nitrophenyl 2-thienyl ketone of m.p. 155°–157°.

EXAMPLE A

The interlocking gelatine capsules of the following composition can be prepared in a known manner:

| Ingredients | Amount in mg/capsules |
| --- | --- |
| L-Dopa | 100 |
| Benserazide hydrochloride | 29.3 |
| 3,4-Dihydroxy-5-nitrophenyl 4-pyridyl ketone | 25 |
| Gelatine | 1 |
| Magnesium stearate | 1 |
| Avicel | 93.7 |
| Mannitol | 100 |
| Capsule fill weight | 350 mg |

We claim:

1. A compound of the formula

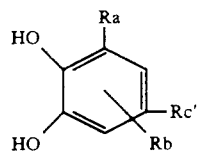

wherein Ra is nitro or cyano, Rb is hydrogen or halogen, Rc' is the group CO—$R^{11}$ wherein $R^{11}$ is a phenyl group optionally mono- or disubstituted by halogen, cyano, hydroxy or lower alkyl, or an ester or ether derivative thereof which is hydrolyzable under physiological conditions or a pharmaceutically acceptable salt thereof.

2. A compound, according to claim 1, wherein Rb is situated in the p-position to Ra.

3. A compound, according to claim 2, wherein Ra is nitro.

4. A compound, according to claim 3, wherein Rb is hydrogen, chlorine or fluorine.

5. A compound, according to claim 4, wherein Rb is hydrogen.

6. A compound, according to claim 1, 3,4-Dihydroxy-5-nitrobenzophenone.

7. A compound, according to claim 1, 2'-Fluoro-3,4-dihydroxy-5-nitrobenzophenone.

8. A pharmaceutical composition comprising a compound of the formula

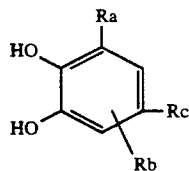

wherein Ra is nitro or cyano, Rb is hydrogen or halogen, Rc is CO—R¹ wherein R¹ is a phenyl group optionally mono- or disubstituted by halogen, cyano, hydroxy or lower alkyl or an ester or ether derivative thereof which if hydrolyzable under physiological conditions or a pharmaceutically acceptable salt thereof, and a therapeutically inert carrier material.

9. A pharmaceutical composition, according to claim 8, wherein the compound of formula Ia is 3,4-dihydroxy-5-nitrobenzophenone.

10. A pharmaceutical composition, according to claim 8, wherein the compound of formula Ia is 2'-fluoro-3,4-dihydroxy-5-nitrobenzophenone.

11. A pharmaceutical composition comprising L-dopa, peripheral decarboxylase inhibitor, a compound of the formula

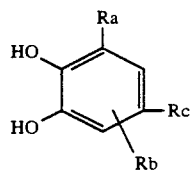

wherein Ra is nitro or cyano, Rb is hydrogen or halogen, Rc is the group CO—R¹ wherein R¹ is a phenyl group optionally mono- or disubstituted by halogen, cyano, hydroxy or lower alkyl or an ester or ether derivative thereof which is hydrolyzable under physiological conditions or a pharmaceutically acceptable salt thereof and a therapeutically inert carrier material.

12. A pharmaceutical composition, according to claim 11, wherein the compound of formula Ia is 3,4-dihydroxy-5-nitrobenzophenone.

13. A pharmaceutical composition, according to claim 11, wherein the compound of formula Ia is 2'-fluoro-3,4-dihydroxy-5-nitrobenzophenone.

14. A compound according to claim 1, wherein said compound is 4-dihydroxy-5'-methyl-5-nitrobenzophenone.

15. A pharmaceutical composition according to claim 8, wherein the compound of formula Ia is 3,4-dihydroxy-4'-methyl-5-nitrobenzophenone.

16. A pharmaceutical composition according to claim 11, wherein the compound of formula Ia is 3,4-dihydroxy-4'-methyl-5-nitrobenzophenone.

17. A pharmaceutical composition for treating depression comprising an effective amount of a compound of the formula

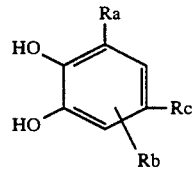

wherein Ra is nitro or cyano, Rb is hydrogen or halogen, Rc is CO—R¹ wherein R¹ is a phenyl group optionally mono- or disubstituted by halogen, cyano, hydroxy or lower alkyl or an ester or ether derivative thereof which if hydrolyzable under physiological conditions or a pharmaceutically acceptable salt thereof, and a therapeutically inert carrier material.

18. A pharmaceutical composition according to claim 17, wherein the compound of formula Ia is 3,4-dihydroxy-4'-methyl-5-nitrobenzophenone.

19. A pharmaceutical composition for treating Parkinson's disease comprising L-dopa, a peripheral decarboxylase inhibitor, a compound of the formula

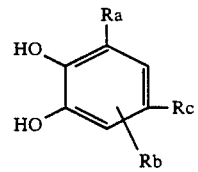

wherein Ra is nitro or cyano, Rb is hydrogen or halogen, Rc is CO—R¹ wherein R¹ is a phenyl group optionally mono- or disubstituted by halogen, cyano, hydroxy or lower alkyl or an ester or ether derivative thereof which if hydrolyzable under physiological conditions or a pharmaceutically acceptable salt thereof, and a therapeutically inert carrier material.

20. A pharmaceutical composition according to claim 19, wherein the compound of formula Ia is 3,4-dihydroxy-4'-methyl-5-nitrobenzophenone.

21. A pharmaceutical composition for inhibiting catechol-O-methyl-transferase, said composition comprising a catechol-O-methyl transferase inhibiting amount of a compound of the formula

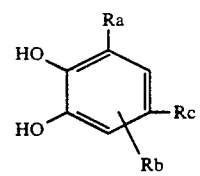

wherein Ra is nitro or cyano, Rb is hydrogen or halogen, Rc is CO—R¹ wherein R¹ is a phenyl group optionally mono- or disubstituted by halogen, cyano, hydroxy or lower alkyl or an ester or ether derivative thereof which if hydrolyzable under physiological conditions or a pharmaceutically acceptable salt thereof, and a therapeutically inert carrier material.

22. A pharmaceutical composition according to claim 8, wherein the compound of formula Ia is 3,4-dihydroxy-4'-methyl-5-nitrobenzophenone.

* * * * *

UNITED STATES PATENT AND TRADEMARK OFFICE
CERTIFICATE OF CORRECTION

PATENT NO. : 5,236,952
DATED : August 17, 1993
INVENTOR(S) : Karl Bernauer, Janos Borgulya, Hans Bruderer, Mose PaPrada, Gerhard Zurcher It is certified that error appears in the above-indentified patent and that said Letters Patent is hereby corrected as shown below:

- Claim 14, Column 61, lines 54-55: "4-dihydroxy-5'-methyl
  - 5-nitrobenzophenone should read --- 3,4-dihydroxy-4'-methyl-5-nitrobenzophenone --- .

Signed and Sealed this

Ninth Day of May, 1995

Attest:

BRUCE LEHMAN

*Attesting Officer*    *Commissioner of Patents and Trademarks*